(12) United States Patent
Mahajan et al.

(10) Patent No.: US 9,594,084 B2
(45) Date of Patent: Mar. 14, 2017

(54) PHOSPHORYLATION OF HISTONES AND USES THEREOF

(71) Applicant: H. LEE MOFFITT CANCER CENTER AND RESEARCH INSTITUTE, Tampa, FL (US)

(72) Inventors: Kiran Mahajan, Tampa, FL (US); Nupam P. Mahajan, Tampa, FL (US)

(73) Assignee: H. Lee Moffitt Cancer Center and Research Institute, Tampa, FL (US)

( * ) Notice: Subject to any disclaimer, the term of this patent is extended or adjusted under 35 U.S.C. 154(b) by 0 days.

(21) Appl. No.: 14/322,587

(22) Filed: Jul. 2, 2014

(65) Prior Publication Data
US 2015/0011567 A1 Jan. 8, 2015

Related U.S. Application Data

(63) Continuation-in-part of application No. PCT/US2013/020395, filed on Jan. 4, 2013.

(60) Provisional application No. 61/583,864, filed on Jan. 6, 2012.

(51) Int. Cl.
| | | |
|---|---|---|
| *G01N 33/53* | (2006.01) | |
| *G01N 33/574* | (2006.01) | |
| *C12Q 1/48* | (2006.01) | |
| *C07K 16/18* | (2006.01) | |
| *C07K 7/08* | (2006.01) | |
| *G01N 33/573* | (2006.01) | |
| *C12Q 1/68* | (2006.01) | |

(52) U.S. Cl.
CPC ......... *G01N 33/57496* (2013.01); *C07K 7/08* (2013.01); *C07K 16/18* (2013.01); *C12Q 1/485* (2013.01); *C12Q 1/6886* (2013.01); *G01N 33/573* (2013.01); *G01N 33/57407* (2013.01); *G01N 33/57484* (2013.01); *C07K 2317/34* (2013.01); *C12Q 2600/106* (2013.01); *C12Q 2600/118* (2013.01); *C12Q 2600/158* (2013.01); *G01N 2333/912* (2013.01); *G01N 2440/14* (2013.01)

(58) Field of Classification Search
None
See application file for complete search history.

(56) References Cited

FOREIGN PATENT DOCUMENTS

| EP | 2213673 A1 | 8/2010 |
|---|---|---|
| WO | 03014142 A2 | 2/2003 |
| WO | 2007030619 A2 | 3/2007 |
| WO | 2007132177 A1 | 11/2007 |

OTHER PUBLICATIONS

Gamper et al (BMC Genomics, 2009, 10(199): 1-17).*
International Search Report and Written Opinion, issued in International Application No. PCT/US2013/020395, mailed Jan. 14, 2014.
Preuss, U, et al., "Novel mitosis-specific phosphorylation of histone H3 at Thr11 mediated by Dlk/ZIP kinase", Nucleic Acids Research, Oxford University Press, Surrey, GB, vol. 31, No. 3, 2003, pp. 878-885.
Lin, T-S, et al., "An association of DNMT3b protein expression with P16INK4a promoter hypermethylation in non-smoking female lung cancer with human papillomavirus infection", Cancer Letters, vol. 226, No. 1, 2005, pp. 77-84.
Bungard, D, et al., "Signaling Kinase AMPK Activates Stress-Promoted Transcription via Histone H2B Phosphorylation", Science, vol. 329, No. 5996, 2010, pp. 1201-1205.
Cheung, W, et al., "Apoptotic phosphorylation of histone H2B is mediated by mammalian sterile twenty kinase", Cell, vol. 113, No. 4, 2003, pp. 507-517.
Mahajan, K, et al., "H2B Tyr37 phosphorylation suppresses expression of replication-dependent core histone genes", Nature Structural & Molecular Biology, vol. 19, No. 9, 2012, pp. 930-939.
Osley, M. A. The regulation of histone synthesis in the cell cycle. Annual review of biochemistry 60, 827-861 (1991).
Borun, T. W., Gabrielli, F., Ajiro, K., Zweidler, A. & Baglioni, C. Further evidence of transcriptional and translational control of histone messenger RNA during the HeLa S3 cycle. Cell 4, 59-67 (1975).
Hereford, L., Bromley, S. & Osley, M. A. Periodic transcription of yeast histone genes. Cell 30, 305-310 (1982).
Hereford, L. M., Osley, M. A., Ludwig, T. R., 2nd & McLaughlin, C. S. Cell-cycle regulation of yeast histone mRNA. Cell 24, 367-375 (1981).
Osley, M. A. & Hereford, L. Identification of a sequence responsible for periodic synthesis of yeast histone 2A mRNA. Proceedings of the National Academy of Sciences of the United States of America 79, 7689-7693 (1982).
Osley, M. A. & Lycan, D. Trans-acting regulatory mutations that alter transcription of *Saccharomyces cerevisiae* histone genes. Molecular and cellular biology 7, 4204-4210 (1987).
Marzluff, W. F., Wagner, E. J. & Duronio, R. J. Metabolism and regulation of canonical histone mRNAs: life without a poly(A) tail. Nature reviews 9, 843-854 (2008).
Takayama, Y. et al. Hsk1- and SCF(Pof3)-dependent proteolysis of S. pombe Ams2 ensures histone homeostasis and centromere function. Developmental cell 18, 385-396 (2010).
Berger, S. L. The complex language of chromatin regulation during transcription. Nature 447, 407-412 (2007).

(Continued)

*Primary Examiner* — Sean Aeder
(74) *Attorney, Agent, or Firm* — Meunier Carlin & Curfman LLC

(57) ABSTRACT

Phosphorylation of histones was observed at certain tyrosine residues which have not been associated with epigenetic modification. These sites include H2B Tyr37, H4 Tyr88 and Tyr 51 and H3 Tyr99. Kinases responsible for the phosphorylation as well as downstream genes regulated by such phosphorylation were also identified. Antibodies that are specific to such phosphorylated histones have been generated, which are useful for detecting the phosphorylation and related events. With such findings, the present disclosure provides compositions and methods for disease diagnosis, prognosis and therapy selection, in particular for cancer, obesity and diabetes.

8 Claims, 56 Drawing Sheets

(56) References Cited

OTHER PUBLICATIONS

Russell, P. & Nurse, P. Negative regulation of mitosis by wee1+, a gene encoding a protein kinase homolog. Cell 49, 559-567 (1987).
Heald, R., McLoughlin, M. & McKeon, F. Human wee1 maintains mitotic timing by protecting the nucleus from cytoplasmically activated Cdc2 kinase. Cell 74, 463-474 (1993).
Lundgren, K. et al. mik1 and wee1 cooperate in the inhibitory tyrosine phosphorylation of cdc2. Cell 64, 1111-1122 (1991).
McGowan, C. H. & Russell, P. Cell cycle regulation of human WEE1. The EMBO journal 14, 2166-2175 (1995).
Mahajan, K. et al. Ack1 mediated AKT/PKB tyrosine 176 phosphorylation regulates its activation. PLoS One 5, e9646 (2010).
Kim, T. H. et al. A high-resolution map of active promoters in the human genome. Nature 436, 876-880 (2005).
Albig, W. & Doenecke, D. The human histone gene cluster at the D6S105 locus. Human genetics 101, 284-294 (1997).
Albig, W., Kioschis, P., Poustka, A., Meergans, K. & Doenecke, D. Human histone gene organization: nonregular arrangement within a large cluster. Genomics 40, 314-322 (1997).
Wang, Z. F. et al. Characterization of the mouse histone gene cluster on chromosome 13: 45 histone genes in three patches spread over 1Mb. Genome research 6, 688-701 (1996).
Marzluff, W. F., Gongidi, P., Woods, K. R., Jin, J. & Maltais, L. J. The human and mouse replication-dependent histone genes. Genomics 80, 487-498 (2002).
Mahajan, K. et al. Effect of Ack1 tyrosine kinase inhibitor on ligand-independent androgen receptor activity. Prostate 70, 1274-1285 (2010).
Laribee, R. N., Fuchs, S. M. & Strahl, B. D. H2B ubiquitylation in transcriptional control: a FACT-finding mission. Genes & development 21, 737-743 (2007).
Sutton, A., Bucaria, J., Osley, M. A. & Sternglanz, R. Yeast ASF1 protein is required for cell cycle regulation of histone gene transcription. Genetics 158, 587-596 (2001).
Cross, S. L. & Smith, M. M. Comparison of the structure and cell cycle expression of mRNAs encoded by two histone H3-H4 loci in Saccharomyces cerevisiae. Molecular and cellular biology 8, 945-954 (1988).
Nakanishi, S. et al. A comprehensive library of histone mutants identifies nucleosomal residues required for H3K4 methylation. Nature structural & molecular biology 15, 881-888 (2008).
Booher, R. N., Deshaies, R. J. & Kirschner, M. W. Properties of Saccharomyces cerevisiae wee1 and its differential regulation of p34CDC28 in response to G1 and G2 cyclins. Embo J 12, 3417-3426 (1993).
Miele, A. et al. HiNF-P directly links the cyclin E/CDK2/p220NPAT pathway to histone H4 gene regulation at the G1/S phase cell cycle transition. Molecular and cellular biology 25, 6140-6153 (2005).
Wei, Y., Jin, J. & Harper, J. W. The cyclin E/Cdk2 substrate and Cajal body component p220(NPAT) activates histone transcription through a novel LisH-like domain. Molecular and cellular biology 23, 3669-3680 (2003).
Zhao J., Dynlacht, B., Imai, T., Hori, T. & Harlow, E. Expression of NPAT, a novel substrate of cyclin E-CDK2, promotes S-phase entry. Genes & development 12, 456-461 (1998).
Zhao, J. et al. NPAT links cyclin E-Cdk2 to the regulation of replication-dependent histone gene transcription. Genes & development 14, 2283-2297 (2000).
Yates, J. R., 3rd, Eng, J. K., McCormack, A. L. & Schieltz, D. Method to correlate tandem mass spectra of modified peptides to amino acid sequences in the protein database. Anal Chem 67, 1426-1436 (1995).
Yates, J. R., 3rd, Eng, J. K. & McCormack, A. L. Mining genomes: correlating tandem mass spectra of modified and unmodified peptides to sequences in nucleotide databases. Anal Chem 67, 3202-3210 (1995).
Perkins, D. N., Pappin, D. J., Creasy, D. M. & Cottrell, J. S. Probability-based protein identification by searching sequence databases using mass spectrometry data. Electrophoresis 20, 3551-3567 (1999).
Salic, A. & Mitchison, T. J. A chemical method for fast and sensitive detection of DNA synthesis in vivo. Proceedings of the National Academy of Sciences of the United States of America 105, 2415-2420 (2008).
Mendez, J. & Stillman, B. Chromatin association of human origin recognition complex, cdc6, and minichromosome maintenance proteins during the cell cycle: assembly of prereplication complexes in late mitosis. Molecular and cellular biology 20, 8602-8612 (2000).
Mahajan, N. P. et al. Activated Cdc42-associated kinase Ack1 promotes prostate cancer progression via androgen receptor tyrosine phosphorylation. Proceedings of the National Academy of Sciences of the United States of America 104, 8438-8443 (2007).
Zhang, Y. et al. Model-based analysis of ChIP-Seq (MACS). Genome Biol 9, R137, doi:10.1186/gb-2008-9-9-r137 (2008).
Mollapour, M. et al. Swe1Wee1-dependent tyrosine phosphorylation of Hsp90 regulates distinct facets of chaperone function. Mol Cell 37, 333-343, (2010).

\* cited by examiner

FIG. 2G

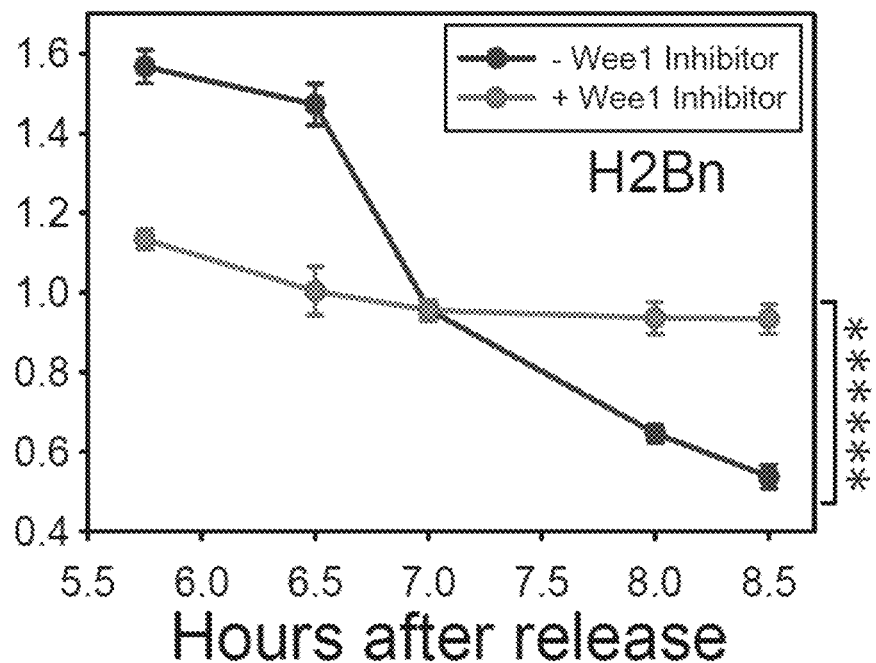

FIG. 3A

| | | | | |
|---|---|---|---|---|
| *Homo sapiens* | 30 | KRSRKES*H*SVYVYKVL | 45 | SEQ ID NO:2 |
| *Bos taurus* | 27 | KRSRKES*H*SIYVYKVL | 42 | |
| *Mus musculus* | 30 | KRSRKES*H*SIYVYKVL | 45 | SEQ ID NO:3 |
| *Rattus norvegicus* | 30 | KRSRKES*H*SVYVYKVL | 45 | |
| *Xenopus laevis* | 30 | RKSRKES*H*AIYVYKVL | 45 | SEQ ID NO:70 |
| *Danio rerio* | 28 | KRTRKES*H*AIYVYKVL | 43 | SEQ ID NO:71 |
| *Aedes aegypti* | 28 | KQRKES*H*AIYIYKVL | 43 | |
| *D. melanogaster* | 27 | KRKRKES*H*AIYIYKVL | 42 | SEQ ID NO:4 |
| *Bombyx mori* | 28 | KHKRKES*H*AIYIYKVL | 43 | |
| *Caenorhabditis elegans* | 27 | KHARKES*H*SVYIYRVL | 42 | SEQ ID NO:5 |
| *S. cerevisiae* | 33 | SKVRKET*H*SSYIYKVL | 48 | SEQ ID NO:6 |

FIG. 11

| | | | |
|---|---|---|---|
| *Homo sapiens* | 44 | KRISGLIYEETRGVLK 59 | SEQ ID NO:57 |
| *Bos taurus* | 45 | KRISGLIYEETRGVLK 60 | SEQ ID NO:72 |
| *Mus musculus* | 46 | KRISGLIYEETRGVLK 61 | SEQ ID NO:73 |
| *Rattus norvegicus* | 45 | KRISGLIYEETRGVLK 60 | SEQ ID NO:74 |
| *Xenopus laevis* | 45 | KRISGLIYEETRGVLK 60 | SEQ ID NO:75 |
| *Danio rerio* | 45 | KRISGLIYEETRGVLK 60 | SEQ ID NO:76 |
| *Aedes aegypti* | 45 | KRISGLIYEETRGVLK 60 | SEQ ID NO:77 |
| *D. melanogaster* | 45 | KRISGLIYEETRGVLK 60 | SEQ ID NO:78 |
| *Bombyx mori* | 45 | KRISGLIYEETRGVLK 60 | SEQ ID NO:79 |
| *Caenorhabditis elegans* | 43 | KRISGLIYEETRGVLK 58 | SEQ ID NO:80 |
| *S. cerevisiae* | 44 | KRISGLIYEEVRAVLK 59 | SEQ ID NO:58 |

FIG. 12

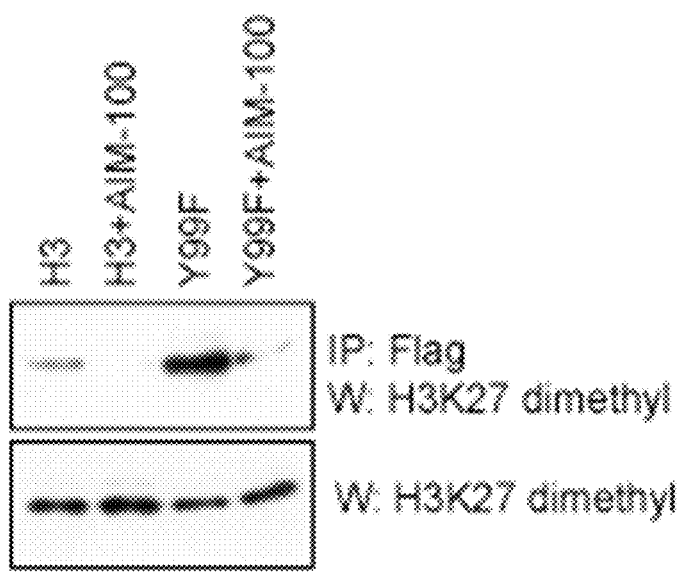

MODified histone peptide array pTyr37-H2B

H3K9me3

| + | - | - | + | + | GST-Wee1 kinase |
| - | - | + | + | - | H2B peptide |
| + | + | - | - | - | Y37F mutant peptide |

PHOSPHORYLATION OF HISTONES AND USES THEREOF

CROSS REFERENCE TO RELATED APPLICATIONS

This application is a continuation-in-part of International Application No. PCT/US2013/020395, filed Jan. 4, 2013, which in turn claims the benefit under 35 U.S.C. §119(e) of U.S. Provisional Application No. 61/583,864, filed Jan. 6, 2012, which is incorporated by reference in its entirety.

FIELD OF THE DISCLOSURE

The disclosure is generally related to compositions and methods for detecting phosphorylated histones and determining activities of kinases regulating such phosphorylation. Also disclosed are methods of disease diagnosis, prognosis and therapy selection based on such detection and determination.

BACKGROUND

Histones are abundant and highly essential eukaryotic proteins that are basic in nature. Two molecules of each of the four core histones, H2A, H2B, H3 and H4, constitute the histone octamer, around which 147 base pairs of DNA are wrapped to form the nucleosome core particle. The core particle is the fundamental repeating unit of eukaryotic chromatin. A linker histone, also known as histone H1, is present in higher eukaryotes and seals two full turns of the DNA to form the complete nucleosome. The major function of nucleosome was appreciated early—this nucleosomal structure is repeated until the entire genomic DNA is packaged into chromatin fibers. The chromatin fibers undergo further compaction to form chromosomes, the basic units of genetic information in all living eukaryotes. In last decade or so it became apparent that histones and chromatin structure regulate access to the information contained within the DNA. And this information plays a crucial role in majority of cellular and metabolic processes e.g. transcription, replication, recombination and DNA damage and repair. This truly has opened the door for the deeper understanding of how histone modification and subsequent changes in chromatin regulates normal human physiology. But the most critical issue is how this process is involved in various diseases e.g. cancer, diabetes and aging.

It is becoming clear that post-translational modifications of histones are important. So far, the core histones have been shown to be phosphorylated, acetylated, methylated, sumoylated, ribosylated and ubiquitylated at various amino acid residues, forming a 'histone code' or 'epigenetic code'. The histone code suggests that histone modifications not only alter the affinity of histones for DNA but importantly act as recognition or binding sites for various factors or proteins to assemble at the site of modification. This results in relay of information that leads to initiation or suppression of specific cellular event or process. Interestingly, the epigenetic code also results in crosstalk between the different modifications, e.g. phosphorylation, methylation, acetylation and ubiquitination.

Histone modifications are the epigenetic changes. It is now known that in addition to genetic defects, epigenetic defects can also result in disease. Epigenetics is also thought to play a major role in the pathogenesis of common, multifactorial disorders. For example, there is evidence suggesting that the primary (idiopathic) disorders like schizophrenia and bipolar disorder are epigenetic defects rather than genetic defects. Epigenetic factors have also been shown to be involved in aging, in rare monogenic disorders like fragile-X mental retardation, and in lymphomas.

SUMMARY

In one embodiment, the present disclosure provides a method for detecting the activity of a WEE1 protein in a sample, comprising contacting the sample with a polypeptide comprising an amino acid sequence of SEQ ID NO: 62 (KRSRKESYSVYVYKVL) or an amino acid sequence having at least about 95% sequence identity to SEQ ID NO: 62, wherein the Y(Tyr)8 residue is unphosphorylated, under conditions allowing the WEE1 protein to phosphorylate the Tyr8 residue; and detecting phosphorylation at the Tyr8 residue, wherein detected phosphorylation indicates WEE1 protein activity in the sample.

In some aspects, the phosphorylation is detected with a probe that specifically recognizes the polypeptide with the phosphorylated Tyr8 residue. In some aspects, the probe comprises an antibody. In some aspects, the antibody is a phosphospecific antibody having specificity to the polypeptide with the phosphorylated Tyr8 residue.

In some aspects, the sample comprises a cancer cell or a cancer stem cell isolated from a subject suspected of having cancer.

Also provided, in one embodiment, is an isolated polypeptide comprising an amino acid sequence of SEQ ID NO: 63 (KRSRKESpYSVYVYKVL) or an amino acid sequence having at least about 95% sequence identity to SEQ ID NO: 63, wherein the Y(Tyr)8 residue is phosphorylated.

Also provided, in one embodiment, is an isolated antibody that specifically recognizes SEQ ID NO: 63 (KRSRKESpYSVYVYKVL), wherein the Y(Tyr)8 residue is phosphorylated. Also provided, in another embodiment, is an isolated antibody that specifically recognizes a histone H2B protein comprising a phosphorylated Tyr37 residue.

Another embodiment provides a method for identifying a cell with an activated WEE1 protein, comprising detecting phosphorylation of a histone H2B protein at the Tyr37 residue in the cell, wherein phosphorylation of the Tyr37 residue indicates presence of an activated WEE1 protein in the cell.

A method is provided, in one embodiment, for identifying a subject as having cancer or at risk of developing cancer, comprising detecting one or more of (a) phosphorylation of a histone H2B protein at the Tyr37 residue in a cell isolated from a subject; (b) expression of one or more genes in the Hist1 gene cluster of cell; or (c) expression of one or more microRNA selected from the group consisting of Mir26b, Mir149, Mir346, Mir350, Mir491, Mir599, Mir670, Mir708, Mir760, Mir879, Mir1192, Mir1965, Mir3058 and Mir5098; or (d) expression of one or more genes selected from the group consisting of IDH2, DNMT3B, JARID2, EYA3, JMJD2c, JMJD1C, CREBBP, SOX4 and SOX18, and identifying that the subject has cancer or is at risk of developing cancer if: (e) the phosphorylation is detected in the cell; (f) the expression of the genes in the Hist1 gene cluster is decreased as compared to a suitable control sample; (g) the expression of the microRNA is different as compared to a suitable control sample; or (h) the expression of the genes of (d) is different as compared to a suitable control sample.

In one embodiment, provided is a method for selecting a cancer patient for a therapy comprising a WEE1 kinase inhibitor, comprising: detecting one or more of: (a) phosphorylation of a histone H2B protein at the Tyr37 residue in a cell isolated from a cancer patient; (b) expression of one or more genes in the Hist1 gene cluster of cell; or (c) expression of one or more microRNA selected from the group consisting of Mir26b, Mir149, Mir346, Mir350, Mir491, Mir599, Mir670, Mir708, Mir760, Mir879, Mir1192, Mir1965, Mir3058 and Mir5098; or (d) expression of one or more genes selected from the group consisting of IDH2, DNMT3B, JARID2, EYA3, JMJD2c, JMJDIC, CREBBP, SOX4 and SOX18, and selecting the cancer patient for the therapy if: (e) the phosphorylation is detected in the cell; (f) the expression of the genes in the Hist1 gene cluster is decreased as compared to a suitable control sample; (g) the expression of the microRNA is different as compared to a suitable control sample; or (h) the expression of the genes of (d) is different as compared to a suitable control sample.

In some aspect, the method further comprises administering the therapy to the cancer patient. In some aspects, the cancer patient suffers from brain cancer, glioblastomas, breast cancer, melanoma, lung cancer, prostate cancer, pancreatic cancer, ovarian cancer, lymphoma, or leukemia.

Another embodiment provides an isolated polypeptide comprising an amino acid sequence of SEQ ID NO: 65 (TVTAMDVVpYALKRQGRT) or an amino acid sequence having at least about 95% sequence identity to SEQ ID NO: 65, wherein the Y(Tyr)9 residue is phosphorylated.

Provided also is an isolated antibody that specifically recognizes SEQ ID NO: 65 (TVTAMDVVpYALKRQGRT), wherein the Y(Tyr)9 residue is phosphorylated. Provided also is an isolated antibody that specifically recognizes a histone H4 protein comprising a phosphorylated Tyr88 residue.

In one embodiment, provided is a method for detecting the activity of a WEE1 protein or an Ack1 protein in a sample, comprising: contacting the sample with a polypeptide comprising an amino acid sequence of SEQ ID NO: 64 (TVTAMDVVYALKRQGRT) or an amino acid sequence having at least about 95% sequence identity to SEQ ID NO: 64, wherein the Y(Tyr)9 residue is unphosphorylated, under conditions allowing the WEE1 protein or the Ack1 protein to phosphorylate the Tyr9 residue; and then detecting phosphorylation at the Tyr9 residue, wherein detected phosphorylation indicates that WEE1 protein activity and/or Ack1 protein activity is likely present in the sample.

Yet another embodiment provides a method for identifying a cell with an activated WEE1 protein or an activated Ack1 protein, comprising detecting phosphorylation of a histone H4 protein at the Tyr88 residue in the cell, wherein phosphorylation of the Tyr88 residue indicates likely presence of an activated WEE1 protein and/or an activated Ack1 protein in the cell.

Also provided is a method for identifying a subject as having cancer or at risk of developing cancer, comprising detecting phosphorylation of a histone H4 protein at the Tyr88 residue in a cell isolated from the subject, and identifying that the subject has cancer or is at risk of developing cancer if phosphorylation of the Tyr88 residue is detected.

One embodiment of the disclosure provides a method for selecting a cancer patient for a therapy comprising a WEE1 kinase inhibitor, an Ack1 inhibitor and/or an EGFR inhibitor, comprising detecting phosphorylation of a histone H4 protein at the Tyr88 residue in a cell isolated from the subject, and selecting the cancer patient for the therapy if phosphorylation of the Tyr88 residue is detected. In some aspects, the method further comprises administering the therapy to the cancer patient. In some aspects, the cancer patient suffers from brain cancer, breast cancer, prostate cancer, pancreatic cancer, melanoma or lung cancer.

Provided, in one embodiement, is an isolated polypeptide comprising an amino acid sequence of SEQ ID NO: 67 (KRISGLIpYEETRGVL) or an amino acid sequence having at least about 95% sequence identity to SEQ ID NO: 67, wherein the Y(Tyr)8 residue is phosphorylated and wherein the polypeptide does not include a histone H4 protein.

Also provided is an isolated antibody that specifically recognizes SEQ ID NO: 67 (KRISGLIpYEETRGVL), wherein the Y(Tyr)8 residue is phosphorylated. Also proided is an antibody that specifically recognizes a histone H4 protein comprising a phosphorylated Tyr51 residue.

A method is provided for detecting the activity of an Ack1 protein, an EGFR protein or an insulin receptor in a sample, comprising: contacting the sample with a polypeptide comprising an amino acid sequence of SEQ ID NO: 66 (KRISGLIYEETRGVL) or an amino acid sequence having at least about 95% sequence identity to SEQ ID NO: 66, wherein the Y(Tyr)8 residue is unphosphorylated, under conditions allowing the Ack1 protein, the EGFR protein or the insulin receptor to activates phosphorylation of the Tyr8 residue; and then detecting phosphorylation at the Tyr8 residue, wherein detected phosphorylation indicates that Ack1 protein activity, EGFR protein activity or insulin receptor activity is likely present in the sample.

Yet provided, in one embodiment, is a method for identifying a cell with an activated Ack1 protein, EGFR protein or insulin receptor, comprising detecting phosphorylation of a histone H4 protein at the Tyr51 residue in the cell, wherein phosphorylation of the Tyr51 residue indicates likely presence of an activated Ack1 protein, EGFR protein and/or insulin receptor protein in the cell.

Provided also is a method for identifying a subject as having cancer or at risk of developing cancer, comprising detecting phosphorylation of a histone H4 protein at the Tyr51 residue in a cell isolated from the subject, and identifying that the subject has cancer or is at risk of developing cancer if phosphorylation of the Tyr51 residue is detected.

One embodiment provides a method for selecting a cancer patient for a therapy comprising an Ack1 inhibitor, an EGFR inhibitor and/or an insulin receptor inhibitor, comprising detecting phosphorylation of a histone H4 protein at the Tyr51 residue in a cell isolated from the subject, and selecting the cancer patient for the therapy if phosphorylation of the Tyr51 residue is detected. In some aspects, the method further comprises administering the therapy to the cancer patient. In some aspects, the cancer patient suffers from brain cancer, breast cancer, melanoma, prostate cancer, pancreatic cancer or lung cancer.

One embodiment provides an isolated polypeptide comprising an amino acid sequence of SEQ ID NO: 69 (ALQEACEApYLVGLFED) or an amino acid sequence having at least about 95% sequence identity to SEQ ID NO: 69, wherein the Y(Tyr)9 residue is phosphorylated and wherein the polypeptide does not include a histone H3 protein.

One embodiment provides an isolated antibody that specifically recognizes SEQ ID NO: 69 (ALQEACEApYLVGLFED), wherein the Y(Tyr)9 residue is phosphorylated. Another embodiment provides an isolated antibody that specifically recognizes a histone H3 protein comprising a phosphorylated Tyr99 residue.

Another embodiment provides a method for detecting the activity of an Ack1 protein, an EGFR protein, an FGFR protein or an insulin receptor in a sample, comprising:

contacting the sample with a polypeptide comprising an amino acid sequence of SEQ ID NO: 68 (ALQEACEAYL-VGLFED) or an amino acid sequence having at least about 95% sequence identity to SEQ ID NO: 68, wherein the Y(Tyr)9 residue is unphosphorylated, under conditions allowing the Ack1 protein, the EGFR protein, the FGFR protein or the insulin receptor to activate phosphorylation of the Tyr9 residue; and then detecting phosphorylation at the Tyr9 residue, wherein detected phosphorylation indicates that Ack1 protein activity, EGFR protein activity, FGFR activity or insulin receptor activity is likely present in the sample.

In another embodiment, provided is a method for identifying a cell with an activated Ack1 protein, EGFR protein, FGFR protein or insulin receptor, comprising detecting phosphorylation of a histone H3 protein at the Tyr99 residue in the cell, wherein phosphorylation of the Tyr99 residue indicates likely presence of an activated Ack1 protein, EGFR protein, FGFR protein and/or insulin receptor protein in the cell.

Also provided is a method for identifying a subject as having cancer or at risk of developing cancer, comprising detecting phosphorylation of a histone H3 protein at the Tyr99 residue in a cell isolated from the subject, and identifying that the subject has cancer or is at risk of developing cancer if phosphorylation of the Tyr99 residue is detected.

Also provided is a method for selecting a cancer patient for a therapy comprising an Ack1 inhibitor, an EGFR inhibitor, an FGFR inhibitor and/or an insulin receptor inhibitor, comprising detecting phosphorylation of a histone H3 protein at the Tyr99 residue in a cell isolated from the subject, and selecting the cancer patient for the therapy if phosphorylation of the Tyr99 residue is detected. In some aspects, the method further comprises administering the therapy to the cancer patient. In some aspects, the cancer patient suffers from prostate cancer, pancreatic cancer, breast cancer, melanoma or lung cancer.

Provided is a method for reducing the body weight or treating obesity or diabetes in a subject, comprising administering to the subject an Ack1 inhibitor or an agent that decrease the expression or activity of Ack1. In one aspect, the Ack1 inhibitor is a small molecule inhibitor or siRNA. In one aspect, the Ack1 inhibitor comprises AIM-100 or an isolated Ack1 antibody.

Applicants provide methods for selecting a cancer patient for a therapy comprising a WEE1 inhibitor, by determing the expression level of the WEE1 protein and IDH2 protein in a sample isolated from the patient, wherein a) overexpression of WEE1 protein and b) underexpression of IDH2 protein in the sample as compared to a control for the WEE1 protein expression level and a control for the IDH2 protein, respectively, selects the cancer patient for the therapy and neither a) nor b) does not select the patient for the therapy. The method can, in one aspect, further comprise, or alternatively consist essentially of, or yet further consist of, administering an effective amount of the WEE1 inhibitor to the cancer patient. Such therapies are known in the art and are described herein.

Suitable cancer patients for this method include for example, a cancer patient suffers from brain cancer, glioblastoma, GBM, melanoma and prostate cancer.

Samples for use in the method comprise, or alternatively consist essentially of, or yet further consist of, one or more of a cancer or tumor cell isolated from the patient.

Any appropriate method for determining the expression level of the WEE1 protein can be used. Non-limiting examples of such include a method comprising determining the amount of mRNA encoding the WEE1 protein in the sample or a method comprising immunohistochemistry, e.g., using an antibody that specifically recognizes the WEE1 protein. These antibodies are known in the art and described herein. In one aspect, the antibody is not a polyclonal or naturally-occurring antibody.

Yet further, the expression level of the IDH2 protein is determined by a method comprising determining the amount of mRNA encoding the IDH2 protein in the sample or by a method comprising immunohistochemistry. In one aspect the immunohistochemical method comprises the use of an anti-IDH2 specific antibody. These antibodies are known in the art. In one aspect, the antibody is not a polyclonal or naturally-occurring antibody.

The method may be repeated after the anti-WEE1 therapy is initiated and based on the second or subsequent measurement, the therapy can be adjusted as needed and as determined by the treating physician or veternarian.

Kits are also provided. In one aspect, the kit comprises (a) one or more proteins selected from: (i) a polypeptide comprising an amino acid sequence of SEQ ID NO: 62 (KRSRKESYSVYVYKVL) or an amino acid sequence having at least about 95% sequence identity to SEQ ID NO: 62, wherein the Y(Tyr)8 residue is unphosphorylated; (ii) a polypeptide comprising an amino acid sequence of SEQ ID NO: 64 (TVTAMDVVYALKRQGRT) or an amino acid sequence having at least about 95% sequence identity to SEQ ID NO: 64, wherein the Y(Tyr)9 residue is unphosphorylated; (iii) a polypeptide comprising an amino acid sequence of SEQ ID NO: 66 (KRISGLIYEETRGVL) or an amino acid sequence having at least about 95% sequence identity to SEQ ID NO: 66, wherein the Y(Tyr)8 residue is unphosphorylated; or (iv) a polypeptide comprising an amino acid sequence of SEQ ID NO: 68 (ALQEACEAYL-VGLFED) or an amino acid sequence having at least about 95% sequence identity to SEQ ID NO: 68, wherein the Y(Tyr)9 residue is unphosphorylated, and (b) one or more antibodies that specifically recognize the one or more proteins of (a). In some aspects, the one or more proteins are affixed on a scaffold.

Hybridomas for producing the antibodies of the present disclosure are also provided, in some embodiments.

BRIEF DESCRIPTION OF THE DRAWINGS

Provided as embodiments of this disclosure are drawings which illustrate by exemplification only, and not limitation.

FIG. 2B-2G are graphs showing histone RNA levels (relative to actin) in synchronized MEFs treated with WEE1 inhibitor, MK1775 (0.625 µM, 14 hr) or untreated and harvested at indicated time points post-release. Total RNA was prepared followed by quantitative RT-PCR. Data are representative of three independent experiments. *p=0.027; p=0.031; *p=0.0059; **p=0.002; *p=0.017; ****p=0.0012.

FIG. 3A is an alignment of H2B protein sequences indicating that tyrosine residue at 37 is invariant from human to yeast.

FIG. 11 is an alignment of H4 protein sequences indicating that tyrosine residue at 51 is invariant from human to yeast.

FIG. 12 is an immunoblot of cell lysates from 293T cells transfected with FLAG-tagged H3 (columns 1 and 2) or Y99F mutant (columns 3 and 4) and treated with AIM-100 (columns 2 and 4) that were either immunoprecipitated with FLAG antibodies and immunoblotted with H3K27 pan-antibodies (top panel) or immunoblotting with H3K27 pan-antibodies without immunoprecipitation (bottom panel).

(FIG. 42a-42e) RNA was isolated from cells treated with WEE1 inhibitor (or siRNA) followed by qRT-PCR using IDH2 and actin primers. (FIG. 42f) MK-1775 treated cells were subjected to qRT-PCR using histone H2A and actin primers *p=0.005; p=0.001; *p=0.001; **p=0.04; ***p=0.03.

(FIG. 44e) In T98G cells treated with the WEE1 specific inhibitor MK-1775, pY88-H2B marks were erased. Low levels of pY37-H2B mark deposition was seen at control site. ****p=0.0001 (FIG. 44f) Melanoma cell lines, IPC298 and WM1366 were treated with the WEE1 specific inhibitor MK-1775 and cell proliferation was assessed.

FIG. 46A shows H1975 cells were either un-irradiated or exposed to 15GY IR and lysates were immunoblotted with indicated Abs. FIG. 46B shows H1975 were irradiated (15GY) in the presence and absence of ATM (Ku55393) and WEE1 inhibitor (MK-1775). Whole cell extracts were immunoblotted with indicated antibodies.

Figure 1A:
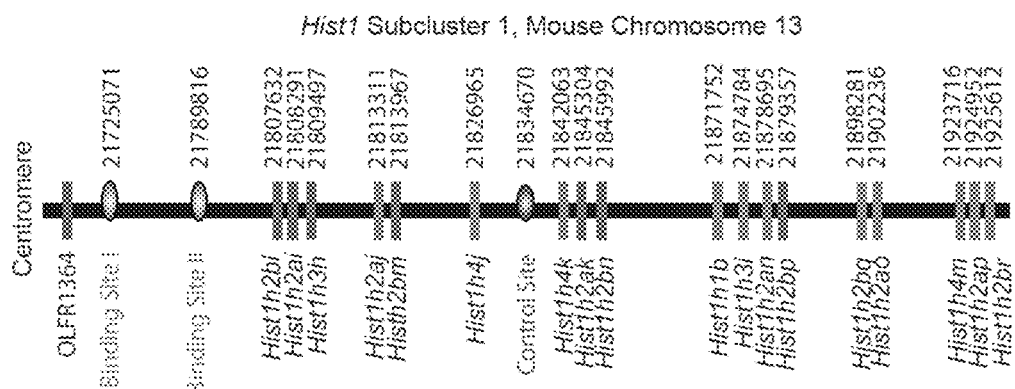
FIG. 1A is a diagram illustrating the position of histone genes in mouse Hist1 subcluster 1 showing two pTyr37-H2B binding sites. Starting nucleotide position is shown above. Subcluster1 is conserved between human and mouse.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION OF THE DISCLOSURE

I. Definitions

The term "phosphospecific probe" refers to a composition that specifically binds a target antigen in its phosphorylated state but does not specifically bind the antigen when it is not phosphorylated. The probe is preferably an antibody (i.e., a phosphospecific antibody).

The term "antibody" refers to a polyclonal, monoclonal, recombinant, or synthetic immunoglobulin molecule that specifically binds a target antigen. In one aspect, monoclonal antibodies are excluded. The term includes intact immunoglobulin molecules, fragments or polymers of those immunoglobulin molecules, chimeric antibodies containing sequences from more than one species, class, or subclass of immunoglobulin, and human or humanized versions of immunoglobulin molecules or fragments thereof containing a least the idiotype of an immunoglobulin that specifically binds the target antigen.

The term "idiotype" refers to the portion of an immunoglobulin molecule that confers the molecule's ability to bind an antigen. The idiotype of an antibody is determined by the complementarity determining regions (CDRs) of the immunoglobulin variable domains ($V_L$ and $V_H$).

The term "peptide" or "polypeptide" can be used to refer to a natural or synthetic molecule comprising two or more amino acids linked by the carboxyl group of one amino acid to the alpha amino group of another. The peptide is not limited by length; thus "peptide" can include polypeptides and proteins.

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc.

The term "aptamer" refers to an oligonucleic acid molecule that specifically binds to a target molecule.

As used herein, the term "small molecule" refers to a compound having a molecular weight of less than 1000 Daltons, and typically between 300 and 700 Daltons. The term may include monomers or primary metabolites, secondary metabolites, a biological amine, a steroid, or synthetic or natural, non-peptide biological molecule(s). In the context of targeted imaging probes that are small molecules, the small molecule can specifically bind the molecular or cellular target.

The term "specifically recognizes" or "specifically binds" refers to the recognition or binding of a molecule to a target molecule, such as an antibody to its cognate antigen, while not significantly binding to other molecules. Preferably, a molecule "specifically binds" to a target molecule with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with the target molecule.

The term "neoplasm" refers to a cell undergoing abnormal cell proliferation. The growth of neoplastic cells exceeds and is not coordinated with that of the normal tissues around it. The growth typically persists in the same excessive manner even after cessation of the growth or other stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasizes to other locations of the body.

The term "subject" or "patient" refers to any individual who is the target of administration. The subject can be a vertebrate, for example, a mammal. Thus, the subject can be a human. The subject can be domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. The term does not denote a particular age or sex.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "isolated" as used herein refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. The term "isolated" is also used herein to refer to cells or tissues that are isolated from other cells or tissues and is meant to encompass both cultured and engineered cells or tissues.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. In one aspect, a biological equivalent of an antibody means one having the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds.

1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

When a genetic marker, e.g., overexpression of WEE1, is used as a basis for selecting a patient for a treatment described herein, the genetic marker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker in a clinical setting is a clear indication that this parameter was used as a basis for initiating, continuing, adjusting and/or ceasing administration of the treatments described herein.

"Cancer" is a known medically as a malignant neoplasm, is a broad group of diseases involving unregulated cell growth. In cancer, cells divide and grow uncontrollably and in one aspect, forming malignant tumors, and invade nearby parts of the body. Non-limiting examples include colon cancer, colorectal cancer, gastric cancer, esophageal cancer, head and neck cancer, breast cancer, lung cancer, stomach cancer, liver cancer, gall bladder cancer, or pancreatic cancer or leukemia.

A "composition" as used herein, intends an active agent, such as a compound as disclosed herein and a carrier, inert or active. The carrier can be, without limitation, solid such as a biotin, a bead or a resin, or liquid, such as phosphate buffered saline.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response.

When a genetic marker, e.g., overexpression of WEE1, is used as a basis for selecting a patient for a treatment described herein, the genetic marker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker in a clinical setting is a clear indication that this parameter was used as a basis for initiating, continuing, adjusting and/or ceasing administration of the treatments described herein.

WEE1 gene or polynucleotide encodes a nuclear protein, which is a tyrosine kinase, belonging to the Ser/Thr family of protein kinases. The gene and the protein it encodes have been characterized. The amino add of the human sequence is deposited at NP_001137448, and the mouse amino add sequence NP_033542. The sequence of the mRNA encoding the human protein is available at GenBank NM_001143976 and the mouse mRNA is available at GenBank NM_009516. Monoclonal antibodies that specifically recognize and bind the proteins, for immunohistochemical analysis, can be purchased from Santa Cruze Biotechnology (sc-5285) or generated using methods known in the art.

Isocitrate dehydrogenase is an enzyme that is encoded in humans the IDH2 gene. The amino acid sequence for the human protein is available at GenBank NP_002159 and the mouse protein is available at NP_766599. The mRNA encoding the proteins are available at GenBank NM_002168 (human) and NM_173011 (mouse). Antibodies that specifically recognize and bind the protein can be made using well known methods or purchased from abcam (ab131263).

II. Detailed Description

It is discovered herein that certain tyrosine residues of various histone proteins, which are not known to be subject to epigenetic modifications, can be phosphorylated in cells. Such amino acid residues include H2B Tyr37, H4 Tyr88 and Tyr 51 and H3 Tyr99. The present disclosure further provides experimental data to reveal the kinases that can phosphorylate these residues, the impact of such phosphorylation to a cell including gene expression changes, and their clinical implications.

A. pY37-H2B

The present disclosure identified a new phosphorylation event, tyrosine 37 in histone H2B (pY37-H2B) mediated by WEE1 tyrosine kinase. The identification was facilitated and confirmed by newly generated pY37-H2B specific antibodies. Chromatin immunoprecipitation followed by sequencing (ChIP-sequencing) revealed that WEE1 mediated H2B Tyr37-phosphorylation occurred at multiple places in chromatin including upstream of histone cluster 1, Hist1 and negatively regulated global histone transcriptional output.

The genes for the five core histones H1/H2A/H2B/H3/H4 are clustered together in the genome of all metazoans. There are 10-20 functional copies of the genes for each of the histone proteins and each individual gene encodes a small fraction of the total histone protein. The Hist1 cluster contains majority of the histone coding genes. The data unveiled a previously unknown mechanism wherein marking major histone gene cluster with H2B Y37-phosphorylation by WEE1 suppressed transcription of histone genes by excluding binding of the transcriptional coactivator NPAT and RNA polymerase II and recruiting histone chaperone HIRA upstream of the Hist1 cluster.

Loss of WEE1 kinase expression by siRNA or inhibition by MK-1775 abrogated H2B Y37-phosphorylation with a concomitant increase in histone transcription in both mammalian and yeast cells. As all eukaryotic cells need to maintain histone levels precisely, any alterations in histone levels leads to genetic instability, loss of chromosome fidelity and increased sensitivity to DNA damaging agents. Thus, these studies have uncovered a new evolutionarily conserved function of WEE1 as an epigenetic modulator that is important for maintaining histone mRNA levels.

In accordance with such discovery, the present disclosure, in one embodiment, provides methods and compositions for detecting WEE1 activity in a cell by either determining the amount of pY37-H2B in the cell. Alternatively, the WEE1 activity can be detected by first incubating the WEE1 with an H2B protein or a fragment of the protein that contains an unphosphorylated Y37 residue, allowing the WEE1 to phosphorylate the protein, and then measuring the phosphorylation of the Y37 residue.

Determination of WEE1 activity has clinical applications. It has been observed that elevated levels of WEE1 significantly correlated with cancer progression (e.g., brain cancer such as GBM), breast cancer such as triple negative breast cancer, melanoma and lung cancer). Therefore, detection of the WEE1 activity can help detection of cancer and prognosis of cancer treatments. Further, cancer treatments that target WEE1 can be selected for those cancer patients that have aberrant WEE1 activities.

Further, the data shows that phosphorylated Y37-H2B modulates the expression of many downstream genes, and thus such downstream genes can also serve as biomarkers for the detection of WEE1 activity. Without limitation, these genes include all the 51 histone genes in the Hist1 gene cluster (e.g., H2Bl, H2Ai, H3 h, H2Aj, H2Bm, H4j, H4k, H2Ak, H2bn, H2Bl, H3 h, H4j, H2Ai, H2Ak and H2Bk H1b, H3i, H2Ah, H2Bp, H2Bq, H2Ao, H4m, H2Ap, H2Br, H2Ah, H4i, H2Ag, H2Bj, H4 h, H4 h, H2Af, H3 g, H2Bh, H3f, H4f, Hid, H3e, H2Ae, H2Bg, H2Bf, H2Ad, H4d, H2Be, H1e, H2Ac, H2Bc, H2t, H4c, H1c, H3c, H2Bb, H2Ab, H3b, H4b, H4a and HH3 g), microRNA including Mir26b, Mir149, Mir346, Mir350, Mir491, Mir599, Mir670, Mir708, Mir760, Mir879, Mir1192, Mir1965, Mir3058 and Mir5098, and IDH2, DNMT3B, JARID2, EYA3, JMJD2c, JMJD1C, CREBBP, SOX4 and SOX18.

B. pY88-H4

It is shown that the Tyr88 residue of H4 can be phosphorylated by the WEE1 or Ack1 kinase. Such phosphorylation can occur in certain cancer cells, including brain cancer cells (e.g., GBM), breast cancer cells (e.g., triple negative breast cancer), prostate cancer, pancreatic cancer, melanoma and lung cancer cells that display activation of WEE1 or Ack1. Therefore, by detecting the Y88-H4 phosphorylation, a cell can be assayed for its WEE1 or Ack1 kinase activity and assessed for its status in carcinogenesis, as well as its suitability for a treatment targeting these kinases.

C. pY51-H4

The histone H4 Tyr51 residue is yet another site newly discovered to undergo phosphorylation in certain cancer cells. The phosphorylation of Y51-H4, as the data shows, can be activated by WEE1, Ack1, EGFR and the insulin receptor, and modulates a number of downstream genes. Therefore, measurement of pY51-H4 can be used to determine the activity of WEE1, Ack1, EGFR or the insulin receptor.

Like Y88-H4, Y51-H4 can be phosphorylated by more than one factor, and thus the detection of phosphorylation of either of these sites suggests that one or more of these factors are active. When used together or alternatively in combination with other phosphorylation targets, these phosphorylation sites can help ascertain which of these factors are actually active. For instance, for a cell, if Y37-H2B is not phosphorylated but Y88-H4 and Y51-H4 are phosphorylated, one can conclude that WEE1 may not be active in the cell, but Ack1 is.

D. pY99-H3

The Tyr99 residue of histone H3 was shown to be phosphorylated by Ack1, EGFR, FGFR and the insulin receptor. Inhibition of this phosphorylation increases dimethylation and trimethylation of Lys 9 of histone H3 and mitigate cancer progression.

It is interesting to note that mice lacking Y99-H3 phosphorylation, through knock out of the Ack1 gene, were healthy but had significant less body weight as compared to the wild-type animals. These data indicate that, in addition to its role in cancer development, pY99-H3 also plays an important role in body weight control or metabolism. By modulating the activity of Ack1 or the phosphorylation of Y99-H3 and dimethylation and trimethylation of Lys 9 of histone H3, therefore, the present disclosure contemplates methods to treat obesity and related diseases, such as diabetes.

III. Compositions

Phosphospecific Probes

Phosphospecific probes that specifically bind tyrosine residues in Histone H2B, H3, or H4 when phosphorylated are provided. The phosphospecific probe preferably specifically binds histone H2B at phosphorylated tyrosine 37 residue (H2B-Tyr37), Histone H4 at phosphorylated tyrosine 51 residue (H4-Tyr51) or tyrosine 88 residue (H4-Tyr88), or Histone H3 at phosphorylated tyrosine 99 residue (H3-Tyr99).

1. Antibodies

In preferred embodiments, the phosphospecific probes are antibodies. Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Preferred CDRs are the CDRs in the example phosphospecific antibodies described in the Examples.

Antibodies for use in the disclosed compositions and methods can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. Fab is the fragment of an antibody that contains a monovalent antigen-binding fragment of an antibody molecule. A Fab fragment can be produced by digestion of whole antibody with the enzyme papain to yield an intact light chain and a portion of one heavy chain. Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region. $(Fab')_2$ is the fragment of an antibody that can be obtained by treating whole antibody with the enzyme pepsin without subsequent reduction. $F(ab')_2$ is a dimer of two Fab' fragments held together by two disulfide bonds. Fv is the minimum antibody fragment that contains a complete antigen recognition and binding site. This region consists of a dimer of one heavy and one light chain variable domain in a tight, non-covalent association ($V_H$—$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

Techniques can also be adapted for the production of single-chain antibodies specific for the cellular targets. Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies. Preferably, if the antibody is to be administered to humans, the antibody is a human antibody or is a "humanized" antibody derived from a non-human animal.

2. Peptides

In some embodiments, the phosphospecific probe can be a peptide. In some embodiments, the peptide can contain the idiotype of an antibody, such as those described above. In other embodiments, the peptide can be identified by screening a library of peptides against the phosphorylated histone.

3. Peptidomimetics

In some embodiments, the phosphospecific probe can be a peptidomimetic. In some embodiments, the peptidomimetic can mimic the idiotype of an antibody, such as those described above. In other embodiments, the peptidomimetic can be identified by screening a library of peptidomimetic against the phosphorylated histone.

A peptidomimetic is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of nonnatural amino acids).

Peptidomimetics can have a non-amino acid residue with non-amide linkages at a given position. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

4. Aptamers

In some embodiments, the phosphospecific probe is an aptamer. Aptamers are single-stranded RNA or DNA oligonucleotides 15 to 60 base in length that bind with high affinity to specific molecular targets. Most aptamers to proteins bind with Kds (equilibrium constant) in the range of 1 μM to 1 nM, similar to monoclonal antibodies. These nucleic acid ligands bind to nucleic acid, proteins, small organic compounds, and even entire organisms.

Aptamers can be selected by incubating the target molecule in a large (e.g., 1010 to 1020) pool of oligonucleotide (usually 40 to 60mers). The large pool size of the oligonucleotide ensures the selection and isolation of the specific aptamer. Aptamers can distinguish between closely related but non-identical members of a protein family, or between different functional or conformational states of the same protein. The protocol called systematic evolution of ligands by exponential enrichment (SELEX) is generally used with modification and variations for the selection of specific aptamers. Using this process, it is possible to develop new aptamers in as little as two weeks.

Phosphorylated Histone or Histone Fragments

The present disclosure provides new phosphorylation sites of histones H2B, H3 and H4. Accordingly, one embodiment provides isolated H2B, H3 or H4 proteins or protein fragments that contain one or more of these sites.

In one embodiment, provided is an isolated polypeptide that includes an amino acid sequence as shown below or one that has at least about 80%, 85%, 90%, 95%, 98% or 99% sequence identity to the sequence shown:

KRSRKESYSVYVYKVL (SEQ ID NO: 62)

KRSRKESpYSVYVYKVL (SEQ ID NO: 63)

TVTAMDVVYALKRQGRT (SEQ ID NO: 64)

TVTAMDVVpYALKRQGRT (SEQ ID NO: 65)

KRISGLIYEETRGVL (SEQ ID NO: 66)

KRISGLIpYEETRGVL (SEQ ID NO: 67)

ALQEACEAYLVGLFED (SEQ ID NO: 68)

ALQEACEApYLVGLFED, (SEQ ID NO: 69)

wherein a lowercase letter "p" indicates that the amino acid following it is phosphorylated.

The unphosphorylated peptides here can be used as substrate to measure the activities of kinases responsible for phosphorylation of one of these sites. The phosphorylated one, on the other hand, can be used to generate or verify antibodies or other types of probes that specifically recognize or bind them. In some aspects, the peptides do not include (e.g., are shorter than) the entire histone protein.

Kits

One or more of the compositions described herein can be assembled in kits. Printed instructions, either as inserts or as labels, indicating quantities of the components to be administered, guidelines for administration, and/or guidelines for mixing the components, can also be included in the kit. Kits of the disclosure can optionally include pharmaceutically acceptable carriers and/or diluents.

The disclosed kit can contain, for example, phosphospecific probes, such as antibodies, that specifically bind one, two, three, or more of H2B-Tyr37, H4-Tyr88, H4-Tyr51, and H3-Tyr99.

In some aspects, the probes are provided on a platform, such as a microarray, to form a panel. In some aspects, the panel further contains probes for other histones or proteins useful for disease detection or prognosis, as known in the art.

Actions Based on Identifications

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, detection of phosphorylation of H2B-Tyr37, H4-Tyr88, H4-Tyr51, or H3-Tyr99 in a sample from the subject is a type of identification. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitoring, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitoring, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitoring, follow-ups, advice, etc. can be based, for example, directly on identifications, a record of such identifications, or a combination. Such treatments, monitoring, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

The disclosed measurements, detections, comparisons, analyses, assays, screenings, etc. can be used in other ways and for other purposes than those disclosed. Thus, the disclosed measurements, detections, comparisons, analyses, assays, screenings, etc. do not encompass all uses of such measurements, detections, comparisons, analyses, assays, screenings, etc.

IV. Methods

Biomedical Research and Clinical Testing

Histone tyrosine phosphorylation antibodies raised against H2B-Tyr37, H4-Tyr88, H4-Tyr51 and/or H3-Tyr99 can be highly useful in biomedical research which involves sensitive techniques such as immunoassays (e.g., immunoblotting, immunoprecipitation, immunohistochemistry), Chip-on-CHIP and ChIP-sequencing.

For example, immunoblotting can be used in research and clinical setting to determine which biological samples contain the disclose phosphorylations that may correlate with disease occurrence, development or progression. Antibodies can also be used in immunoprecipitation experiments to identify interacting proteins or proteins that partner with them to regulate specific biological processes, such as proteins required for cell cycle.

Chromatin Immunoprecipitation followed by hybridization (Chip-on-CHIP) and Chip-sequencing can be used to determine the localization of this modification at specific genomic locations and to determine which genes are targeted and turned on and off in a variety of diseases and disorders such as cancer, diabetes, obesity and diet related disorders.

Histone H2B-Tyr37, H4-Tyr88, H4-Tyr51 and H3-Tyr99 antibodies can be used for analysis of cellular response to growth and proliferation signals of normal and cancer cell types, based on the phosphorylation patterns. The examples are: (a) Response to insulin and insulin like growth factors in cancer, obesity related disorders and in diabetes; and (b) Response to platelet derived growth factors in bone marrow transplants. Blood and tissue biopsies obtained from known cancer, diabetes or obese patients can be screened with the antibodies to detect differences in expression profiles. Significant alterations can be correlated with disease progression.

Stem cells offer great promise for new medical treatments and will highly benefit a number of people afflicted with a variety of disorders or diseases. However, at the present time very limited markers exist which can identify whether a cell in question is a stem cell. Stem cells have the ability to differentiate into any cell type and they have unlimited renewal capacity and can therefore be used in regenerative medicine. Histones are fundamental protein entities and the disclosed histone modifications are highly responsive to growth signals. In some embodiments, these modifications occur in undifferentiated or differentiated stem cells. The H2B-Tyr37, H4-Tyr88, H4-Tyr51 and H3-Tyr99 antibodies can be used to identify and categorize the different stem cell populations.

The histone antibodies can be used to determine if stem cells have changed into specific clonal lineages (lymphoid-immune system, erythroid-blood cell, neuronal cells-nerve, muscle, organ specific such as liver, pancreas, heart or kidney), cancer stem cells (these cells may have the capacity to grow in an uncontrolled fashion and demonstrate resistance to many drugs that kill differentiated cancer cells). H2B-Tyr37, H4-Tyr88, H4-Tyr51 and H3-Tyr99 antibodies can be used to define drug resistant cancer stem cells and cancer cell types and may be used to predict response to treatment.

H2B-Tyr37, H4-Tyr88, H4-Tyr51 and H3-Tyr99 antibodies can be used to analyze patient samples after radiotherapy and chemotherapy to determine the effect of the treatment on gene expression and cellular proliferations.

Tagged H2B-Tyr37, H4-Tyr88, H4-Tyr51 and H3-Tyr99 antibodies can be used to isolate protein complexes of interest that may be required for specific biological process such as embryo development or patterning in various organisms, such as yeasts, worms, flies, fishes, frogs, mice, and humans.

H2B-Tyr37, H4-Tyr88, H4-Tyr51 and H3-Tyr99 antibodies can be used in global genomic, metabolomic and proteomics studies to identify candidate genes that are regulated by the histone modification in various organisms, such as yeasts, worms, flies, fishes, frogs, mice, and humans.

H2B-Tyr37, H4-Tyr88, H4-Tyr51 and H3-Tyr99 antibodies can be used to study X chromosome imprinting. Mammals such as mice and humans achieve dosage compensation by inactivating one of the X chromosomes in females. Expression profiling with H2B-Tyr37, H4-Tyr88, H4-Tyr51 and H3-Tyr99 antibodies in blood or tissue samples can reveal whether any disease is a consequence of loss of X chromosome imprinting.

Genes associated with phosphorylated H2B-Tyr37, H4-Tyr88, H4-Tyr51 and/or H3-Tyr99 can be identified and assessed. For example, changes in expression of genes associated with phosphorylated H2B-Tyr37, H4-Tyr88, H4-Tyr51 and/or H3-Tyr99 can be used to detect, diagnose, prognose, etc. cancer and other diseases. Examples of genes and genomic sequences associated with phosphorylated H2B-Tyr37, H4-Tyr88, H4-Tyr51 and/or H3-Tyr99 are observed. As described herein, association of phosphorylated H2B-Tyr37, H4-Tyr88, H4-Tyr51 and/or H3-Tyr99 with genes affects expression of these genes and can thus affect disease. Thus, for example, detection of certain expression levels and/or changes in expression levels of genes associated with phosphorylated H2B-Tyr37, H4-Tyr88, H4-Tyr51 and/or H3-Tyr99 can be used in all of the ways and for all of the purposes disclosed herein for detection of associated with phosphorylated H2B-Tyr37, H4-Tyr88, H4-Tyr51 and/or H3-Tyr99.

All of the methods disclosed herein can be used in and with any relevant cells, tissues, organs, organisms, etc. to assess, for example, histone phosphorylation, gene and chromatin associations of phosphorylated histones, and the effect of histone phosphorylation and gene association on gene expression, epigenetic phenotypes, physiology, and disease conditions, progression, etc. The disclosed phosphospecific probes, such as the disclosed antibodies, are especially useful for studying epigenetic effects of histone phosphorylation at a basic level in experimental organisms.

Immunoassays

In some embodiments, the disclosed phosphospecific probes are antibodies, which are used in an immunoassay to detect a phosphorylated histone. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immuoprecipitation assay (IP), immunobead capture assays, Western blotting, dot blotting, gel-shift assays, ChIP, ChIP-on-CHIP, ChIP-sequencing, flow cytometry, protein arrays, antibody arrays, multiplexed bead arrays, magnetic capture, in vivo imaging, fluorescence resonance energy transfer (FRET), and fluorescence recovery/localization after photobleaching (FRAP/FLAP).

Immunoassays can include methods for detecting or quantifying the amount of a molecule of interest (such as phosphorylated histones) in a sample, which generally involves the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

B. Diagnosing, Prognosing, and Treating Disease

Methods for diagnosing a disease in a subject are provided that involve assaying a sample from the subject for phosphorylation of human Histone H2B tyrosine 37 residue, human Histone H4 tyrosine 51 residue, or human Histone H3 tyrosine 99 residue.

In some embodiments, the disclosed epigenetic changes can be reversed by drugs and therefore are good targets for the prevention and treatment of disease. The field of epigenetics is inspiring the discovery of new drugs, and is gaining importance as part of toxicology testing during drug development. Epigenetic therapy, the use of drugs to correct epigenetic defects, is relatively new and rapidly developing area of pharmacology. Epigenetic therapy is a potentially very useful form of therapy because epigenetic defects, when compared to genetic defects, are thought to be more easily reversible with pharmacological intervention. In addition to holding promise as therapeutic agents, epigenetic drugs may also be able to prevent disease.

To assess the effect of histone H2B-Tyr37, H4-Tyr88, H4-Tyr51 and H3-Tyr99 phosphorylations on health and disease, epigenetic variations were catalogued across the genome or epigenome in different tissues and at various stages of development. Epigenetic changes can be detected in several ways. One method uses chromatin immunoprecipitation, or ChIP. This involves crosslinking DNA with its associated proteins and then shearing the DNA. The fragments that contain H2B-Tyr37, H4-Tyr88, H4-Tyr51 and H3-Tyr99 phosphorylations are extracted by immunoprecipitation with antibodies specific for H2B-Tyr37, H4-Tyr88, H4-Tyr51 and H3-Tyr99 phosphorylations. The immunoprecipitated DNA is purified and labeled with a fluorescent tag. This is then applied to the surface of a DNA microarray containing a set of probes—a procedure commonly referred to as ChIP-on-chip. The purified ChIP-DNA can also be sequenced, called as ChIP-sequencing.

Using ChIP-on-CHIP and ChIP-sequencing approach, about 3500 distinct sites in genome which have histone H2B-Tyr37 phosphorylation were identified. Further, about 500 distinct sites in genome which have histone H4-Tyr51 phosphorylation were identified. The genes proximal to these sites (in some cases sites are located within genes) are likely to be modulated by H2B-Tyr37 or H4-Tyr51 phosphorylations, respectively.

Availability of highly specific antibodies and the knowledge of the sites at which histone are modified would allow us to identify inhibitors (drugs) that suppresses H2B-Tyr37, H4-Tyr88, H4-Tyr51 and H3-Tyr99 phosphorylations in epigenome.

The kinase WEE1 is primarily responsible for histone phosphorylations at H2B-Tyr37. The tyrosine kinases Ack1 and EGFR are primarily responsible for histone phosphorylations at H4-Tyr51 and H3-Tyr99. The specific inhibitors that suppress ability of WEE1 and Ack1 to phosphorylate H2B at Tyr37 and H3 atTyr99 would therefore be therapeutically useful, especially in those patients where phosphorylation of regulatory regions of genes is an established epigenetic change known to occur. This 'personalized therapy' would bring in high benefits and reduce tumor related deaths.

Therefore, also disclosed is a personalized method of treating a disease in a subject. The method involves first assaying a sample from the subject for phosphorylation of human Histone H2B tyrosine 37 residue, human Histone H4 tyrosine 88, human Histone H4 tyrosine 51 residue, or human Histone H3 tyrosine 99 residue.

In this method, detection of phosphorylation at human Histone H2B tyrosine 37 residue is an indication that the therapy selected should include an inhibitor of WEE1 kinase. Detection of phosphorylation at human Histone H3 tyrosine 99 residue is an indication that the therapy selected should include an inhibitor of Ack1 or EGFR or FGFR or insulin receptor kinase. Detection of phosphorylation human Histone H4 tyrosine 51 or tyrosine 88 residue is an indication that the therapy selected should include an inhibitor of WEE1 or EGFR kinase and/or Ack1 kinase.

The disclosed method system can further involve the use of a computer system to compare levels of the one or more of the disclosed biomarkers to control values. For example, the computer system can use an algorithm to compare levels of two or more biomarkers and provide a score representing the risk of disease onset based on detected differences. Therefore, also provided is an apparatus for use in diagnosing, prognosing, or selecting a therapy in a subject that includes an input means for entering phosphorylated histone level values from a sample of the subject, a processor means for comparing the values to control values, an algorithm for giving weight to specified parameters, and an output means for giving a score representing the risk of disease onset.

1. Cancer

Most cancers are a mixture of genetic and epigenetic changes. Although it is now well recognized that in most of cancers the epigenetics changes play a crucial role, the identities of precise histone phosphorylation events were not known, and the tools, e.g., phosphorylation-specific antibodies, were not available.

Four histone tyrosine phosphorylation events, H2B-Tyr37, H4-Tyr88, H4-Tyr51 and H3-Tyr99, are disclosed and characterized. These four epigenetic changes contribute to the development and progression of cancer. H2B-Tyr37, H4-Tyr88, H4-Tyr51 and H3-Tyr99 phosphorylations regulate gene expression without changing the DNA sequence. Further, these four epigenetic deregulations are involved in tumor cell biology, including cell growth, differentiation, and cell death, and therefore can be linked to patient prognosis.

Significant increase in H2B-Tyr37 phosphorylation was seen in prostate (LNCaP), ovarian (A2780-CP), lymphoma (Raji), leukemia (Jurkat) and melanoma (WM35) derived cell lines using immunoprecipitation with phosphospecific antibodies. Significant increase in H4-Tyr51 phosphorylation was seen in the breast cancer derived MCF-7 cells and prostate cancer derived LAPC4 cells using immunoprecipitation with phosphospecific antibodies.

Assessment of histone phosphorylation can be performed in any sample and can be performed on samples of or derived from any particular cells, tissues, and/or organs or combinations of particular cells, tissues and/or organs.

Activated Ack1 (e.g. pTyr284-Ack1) phosphorylates histone H3 at tyrosine 99. Ack1 phosphorylation of H3 at Tyr99 was significantly compromised upon Ack1-specific small molecule inhibitor, AIM-100. Notably, AIM-100 suppressed testosterone-independent expression of PSA, NKX3,1 and TMPRSS2 genes and mitigated the growth of prostate xenograft tumors. Thus, marking of chromatin within androgen receptor or AR-target gene promoters with H3-Tyr99-phosphorylation is required for its transcriptional activation in androgen-deprived environment of castration-resistant prostate tumors. The disclosed (actually, not yet published) study uncovered a previously unknown mechanism of regulation of Tyr-phosphorylated AR or pTyr-AR-target gene expression, which can be therapeutically reversed by suppression of Ack1/AR/H3-Tyr99 signaling by Ack1 inhibitor.

There was a positive relationship between tumor differentiation and H2B-Tyr37, H4-Tyr88, H4-Tyr51 and H3-Tyr99 phosphorylations. In some embodiments, expression of H2B-Tyr37, H4-Tyr88, H4-Tyr51 and/or H3-Tyr99 phosphorylations is a survival predictor for patients with certain cancers, such as brain, melanoma, CML, breast, prostate, and lung cancers.

Aberrations in post-translational modifications of histones e.g. H2B-Tyr37, H4-Tyr88, H4-Tyr51 and H3-Tyr99 phosphorylations, occur not only at individual promoters, but also occur over large regions of chromatin including small non-coding RNA coding regions, repetitive sequences and non-promoter sequences.

Changes in global levels of individual histone modifications are also associated with cancer and these changes are predictive of clinical outcome. Through immunohistochemical staining of primary prostatectomy tissue samples, the percentage of cells that stained for the histone H2B-Tyr37, H4-Tyr88, H4-Tyr51 and H3-Tyr99 phosphorylations was determined. Grouping of samples with similar patterns of modifications identified two disease subtypes with distinct risks of tumor recurrence in patients with low-grade prostate cancer. These histone modification patterns were predictors of outcome independently of tumor stage, preoperative prostate-specific antigen levels, and capsule invasion. Thus, widespread changes in specific histone modifications indicate previously undescribed molecular heterogeneity in prostate, breast, brain and lung cancer and underlie the broad range of clinical behavior in cancer patients.

Collectively, these data indicate that histone H2B-Tyr37, H4-Tyr88, H4-Tyr51 and H3-Tyr99 phosphorylations patterns serve as outcome predictors for patients undergoing resection for brain, lung, melanoma, breast and prostate cancers. Further, these results indicate that these three histone modifications are associated with increased gene activity and the aggressiveness of cancer phenotype.

Therefore, the disclosed methods can be used to diagnose, prognose, and/or treat cancer. In some embodiments, the cancer of the disclosed methods can be any cell in a subject undergoing unregulated growth. In preferred embodiments, the cancer is any cancer cell capable of metastasis. For example, the cancer can be a sarcoma, lymphoma, leukemia, carcinoma, blastoma, or germ cell tumor. A representative but non-limiting list of cancers that the disclosed compositions can be used to detect include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Disclosed are methods of treating cancer in a subject that involves first contacting a cancer sample from the subject with one of more of the disclosed phosphospecific probes or antibodies. In patients where phosphorylated H2B-Tyr37 is detected in the cancer sample, the method further involves administering to the subject a WEE1 inhibitor. In patients where phosphorylated H3-Tyr99 is detected in the cancer sample, the method further involves administering to the subject a Ack1 inhibitor. Also disclosed are methods of treating cancer in a subject that involves administering a WEE1 inhibitor to a subject in which phosphorylated H2B-Tyr37 was detected. Also disclosed are methods of treating cancer in a subject that involves administering an Ack1 inhibitor to a subject in which phosphorylated H3-Tyr99, H4-Tyr51 was detected.

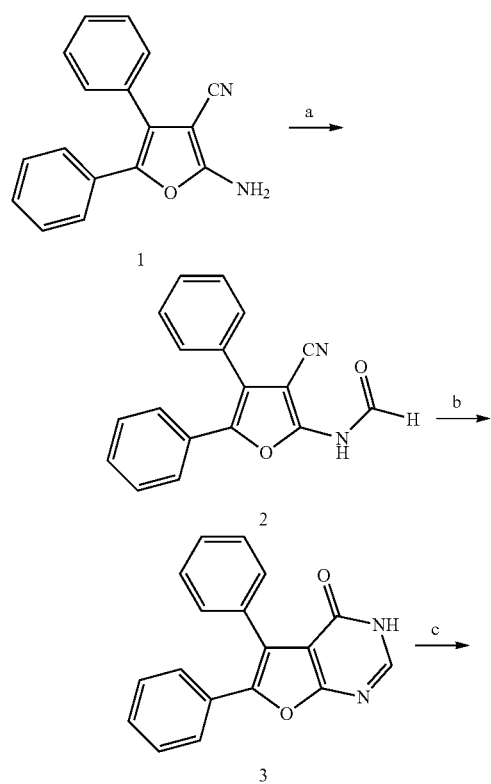

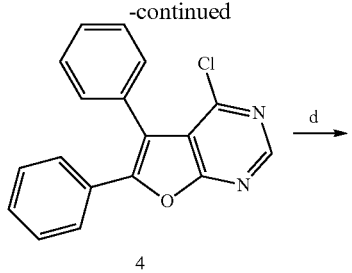

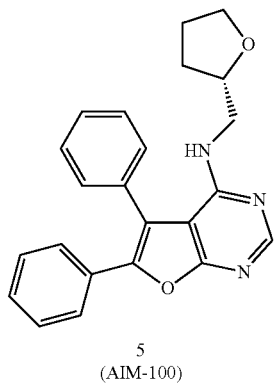

(AIM-100)

Inhibitors for WEE1 and Ack1 are known in the art; so are methods of preparing them. For instance, to prepare AIM-100, an Ack1 inhibitor, synthesis can start from commercially available compound 1 (shown above). (a) Ac2O, HCOOH, 60° C., 6 hr, followed by slow addition of 1 at 0° C. then rt 12 hr, 90%; (b) AcOH, microwave heating at 200° C., 60 min, 75%; (c) POCl3, 55° C., 2 hr, under argon, 100%; (d) (S)-(+)-Tetrahydrofurfurylamine, EtOH, reflux, 5 hr, 87%.

EXAMPLES

Example 1

Phosphorylation of Histone H2B at Tyrosine 37 Suppresses Expression of Core Histone Genes in Hist1 Cluster Core histone mRNA levels are exquisitely regulated within cells. Histone transcription is initiated at the G1/S phase and is actively downregulated in the G2 phase to avoid overproduction soon after completion of DNA synthesis in S phase (Osley, M. A. (1991) Annual Review of Biochem., 60:827-861; Borun, T. W. et al. (1975) Cell 4:59-67; Hereford, L. et al. (1982) Cell 30:305-310; Hereford, L. M. et al. (1981) Cell 24:367-375; Osley, M. A. et al. (1982) Proc. Nat. Acad. Sci. U.S.A., 79:7689-7693; Osley, M. A. et al. (1987) Mol. Cell. Biol., 7:4204-4210). While the rapid decrease in histone transcript levels are accomplished by increasing mRNA turnover of the replication-dependent histone mRNAs that encode the bulk of the histone proteins in metazoan (Marzluff, W. F. et al. (2008) Nature Reviews, 9:843-854), in *Schizosaccharomyces pombe*, degradation of a transcriptional activator for histone transcription maintains the histone pool (Takayama, Y. et al. (2010) Developmental Cell, 18:385-396). However, the precise mechanistic details of cessation of histone mRNA synthesis have not been clear.

This example demonstrates that histone H2B phosphorylation at tyrosine 37 (Tyr37) is critical for suppression of core histone mRNA synthesis. Native Chromatin immunoprecipitation (ChIP) followed by hybridization revealed that H2B Tyr37 phosphorylation occurs upstream of histone cluster 1, Hist1, in S phase which resulted in transcriptional suppression of multiple histone encoding genes. WEE1, a tyrosine kinase, was identified to be the kinase that phosphorylates H2B at Tyr37. Knockdown or inhibition of WEE1 resulted in significant decrease in H2B Tyr37 phosphorylation and concomitant increase in transcription of core histone genes. Consistently, *Saccharomyces cerevisiae* point mutant lacking this Tyr-phosphorylation site (H2B Y40A) also lost the ability to suppress histone transcription. Moreover, WEE1 mediated H2B Tyr37 phosphorylation excluded binding of the transcriptional coactivator NPAT and RNA polymerase II upstream of Hist1 cluster down-regulating histone mRNA synthesis. Taken together, these data unveil a previously unknown mechanism wherein marking chromatin with H2B-Tyr37-phosphorylation inhibits histone gene transcription thereby lowering the burden on histone mRNA turnover machinery to degrade these abundant mRNAs.

Materials and Methods

Cell Culture, Recombinant Histones, siRNAs and Antibodies

Mouse embryo fibroblasts (MEFs) and HEK293 cell lines were grown in DMEM supplemented with 10% FBS and antibiotics. H1975 human lung cancer cell line was grown in RPMI supplemented with 10% FBS and antibiotics. The following antibodies and inhibitor were used: WEE1 monoclonal antibody (Abnova), WEE1 polyclonal antibody (Biovision), WEE1 inhibitor MK1775 (Calbiochem), anti-NPAT (BD Biosciences), anti-RNA Pol II (Active Motif), anti-tubulin (Santacruz), anti-H2A, anti-H2B, anti-H3, anti-H4, anti-Cdc2Y15, anti-Cdc2 antibodies (Cell signaling), anti-yeast H2B (Active Motif) and anti-myc antibody (Invitrogen). Purified human H2A, H2B, H3 and H4 recombinant proteins were purchased from NEB and recombinant GST-WEE1 protein was purchased from Invitrogen. NPAT and WEE1 siRNAs were purchased from Santacruz. WEE1 KD and WEE1 WT constructs were obtained. WT and swe1Δ mutant yeast (*S. cerevisiae*), WT and H2B Y40A mutant yeast were obtained.

Mass Spectrometric Identification of H2B Tyr-Phosphorylation Sites

Total histones were purified from HEK293 cells using histone minipurification kit (Active motif) as per manufacturer's instructions. The purified histones were subjected to SDS-PAGE electrophoresis (18%) and the gel was stained Coomassie Brilliant Blue-R250 (BioRad). A prominent band of ~14 kDa was excised, and treated with Tris(2-carboxyethyl)phosphine hydrochloride (TCEP) and iodoacetamide. Trypsin in-gel digestion was carried on at 37° C. overnight. The extracted peptides were analyzed by LC-MS/MS. A nanoflow liquid chromatograph (U3000, Dionex, Sunnyvale, Calif.) coupled to an electrospray ion trap mass spectrometer (LTQ-Orbitrap, Thermo, San Jose, Calif.) was used for tandem mass spectrometry peptide sequencing experiments. The sample was first loaded onto a pre-column (5 mm×300 μm ID packed with C18 reversed-phase resin, 5 μm, 100 Å) and washed for 8 minutes with aqueous 2% acetonitrile and 0.04% trifluoroacetic acid. The trapped peptides were eluted onto the analytical column (C18, Pepmap 100, Dionex, Sunnyvale, Calif.).

The 120-minute gradient was programmed as: 95% solvent A (2% acetonitrile+0.1% formic acid) for 8 minutes, solvent B (90% acetonitrile+0.1% formic acid) from 5% to 50% in 35 minutes, then solvent B from 50% to 90% B in 2 minutes and held at 90% for 5 minutes, followed by solvent B from 90% to 5% in 1 minute and re-equilibrate for 10 minutes. The flow rate on analytical column was 300 nl/min. Five tandem mass spectra were collected in a data-dependent manner following each survey scan. The MS scans were performed in Orbitrap to obtain accurate peptide mass measurement and the MS/MS scans were performed in linear ion trap using 60 second exclusion for previously sampled peptide peaks. Sequest (Yates, J. R., 3rd et al. (1995) Anal. Chem., 67:1426-1436, 3202-3210) and Mascot (Perkins, D. N. et al. (1999) Electrophoresis, 20:3551-3567) searches were performed against the Swiss-Prot human database. Two trypsin missed cleavages were allowed, the precursor mass tolerance was 1.08 Da. MS/MS mass tolerance was 0.8 Da. Dynamic modifications included carbamidomethylation (Cys), oxidation (Met) and phosphorylation (Ser/Thr/Tyr). Both MASCOT and SEQUEST search results were summarized in Scaffold 2.0.

Generation and Affinity Purification of pTyr37-H2B Monoclonal and Polyclonal Antibody Two H2B peptides coupled to immunogenic carrier proteins were synthesized as shown below and pTyr37-H2B antibodies were custom synthesized by 21$^{st}$ century Biochemicals, MA.

```
The phosphopeptide:
                                  (SEQ ID NO: 11)
Ac-KRSRKES[pY]SVYVYKVL-Ahx-C-amide.

The non-phospho peptide:
                                  (SEQ ID NO: 12)
Ac-KRSRKESYSVYVYKVL-Ahx-C-amide.
```

In brief, two rabbits were immunized twice with the phosphopeptide, several weeks apart, and enzyme-linked immunosorbent assay was performed to determine the relative titer of sera against phosphorylated and nonphosphorylated peptides. The titer against phosphorylated peptides (~1:40,000) was much greater than nonphosphorylated peptide (1:2000). The sera were affinity purified. Two antigen-affinity columns were used to purify the phospho-specific antibodies. The first column was the non-phosphopeptide affinity column. Antibodies recognizing the unphosphorylated residues of the peptide bound to the column and were eluted as pan-specific antibodies. The flow-through fraction was collected and then applied to the second column, the phosphopeptide column. Antibodies recognizing the phospho-residue bound to the column and were eluted as phospho-specific antibodies. The antibodies were extensively validated for its specificity by immunoblottings as shown in manuscript.

Antibodies against H3 Tyr99 and H4 Tyr51 and Tyr88 were produced using the same techniques (but substituting appropriate H3 and H4 peptides, respectively, for immunization of rabbits).

Cell Synchronization Using a Double Thyimidine Block

MEFs or H1975 were grown to 60-70% confluency in serum rich media. Thymidine is added at a final concentration of 2 mM and incubated for 17 hours. Cells were washed three times with phosphate buffered saline (PBS) and fresh serum containing media was added. After 10 hours, thymidine was added again to 2 mM final concentration. The cells were incubated for 17 hours and washed three times with PBS, replaced with serum containing media and time points were collected.

EdU Staining

For rapid detection of DNA synthesis in proliferating cells we used the chemical method of Salic and Mitchison which is based on the incorporation of 5-ethynyl-2'-deoxyuridine (EdU) and its subsequent detection by a fluorescent azide through a Cu(I)-catalyzed [3+2] cycloaddition reaction ("click" chemistry) (Salic, A. et al. (2008) Proc. Nat. Acad. Sci. U.S.A., 105:2415-2420). Reagents are available as a kit from Invitrogen (Cat#350002). EdU was added at a final concentration of 10 μM and cells were harvested at the indicated timepoints. EdU-labeled cells were fixed with 4% paraformaldehyde and cells were processed for measuring DNA synthesis as described in the Click-it-EdU Alexa Flour 488 Flow Cytometry Assay protocol (Invitrogen). Samples were analyzed using the FACS Calibur flowcytometer, 20,000 events were collected and analysis was carried out using the FloJo software.

Cell Fractionation and Immunoprecipitations

Chromatin extraction was performed as described (Mendez, J. et al. (2000) Mol. Cell. Biol., 20:8602-8612). The cells were resuspended in Buffer A (10 mM HEPES pH7.9, 10 mM KCl, 1.5 mM $MgCl_2$, 0.34 M sucrose, 10% Glycerol, 1 mM DTT, protease and phosphatase inhibitor cocktail). Triton X-100 was added to a final concentration of 0.1% and the cells were incubated on ice for 5 minutes. The tubes were centrifuged at 1300 g, 4° C. Nuclei were collected in the pellet, and lysed in Buffer B (Buffer A plus 3 mM EDTA, 0.2 mM EGTA, 1 mM DTT, protease and phosphatase inhibitors including sodium fluoride and sodium vanadate). Insoluble chromatin was collected by centrifugation for 4 minutes at 1700 g, washed once in buffer B and centrifuged. The final chromatin pellet was resuspended in buffer, sonicated for subsequent steps. For immunoprecipitations, cells were lysed in receptor lysis buffer (RLB) containing 25 mmol/L HEPES (pH 7.5), 500 mmol/L NaCl, 1% Triton X-100, 10% glycerol, phosphatase inhibitors (10 mmol/L NaF, 1 mmol/L $Na_2VO_4$), and protease inhibitors) (Mahajan, K. et al. PLoS One 5, e9646 (2010)). For co-immunoprecipitation, cells were lysed in low salt RLB buffer containing 25 mmol/L HEPES (pH 7.5), 225 mmol/L NaCl, 1% Triton X-100, 10% glycerol, phosphatase inhibitors (10 mmol/L NaF, 1 mmol/L $Na_2VO_4$), and protease inhibitor mix (Roche).

In Vitro Kinase Assay

For the in vitro kinase assay, 340 ng of purified GST-WEE1 (Invitrogen) and 1 μg of H2A/H2B/H3/H4 (NEB) were incubated in the presence or absence of WEE1 inhibitor in WEE1 kinase assay buffer containing 50 mM HEPES (pH 7.5), 15 mM $MgCl_2$, 1 mM EGTA, 10% glycerol, 10 mM DTT and 0.1 mM ATP at 30° C. After 60 mins, the reaction separated on SDS-PAGE (18%) followed by immunoblottings with pTyr37-H2B, H2B, H2A, H3, H4 and WEE1 antibodies.

Quantitative RT-PCR

All RT reactions were done (Mahajan, K. et al. (2010) PLoS One, 5:e9646) at the same time so that the same reactions could be used for all gene studies. For the construction of standard curves, serial dilutions of pooled sample RNA were used (50, 10, 2, 0.4, 0.08, and 0.016 ng) per reverse transcriptase reaction. One "no RNA" control and one "no Reverse Transcriptase" (No RT) controls were included for the standard curve. Three reactions were performed for each sample: 10 ng, 0.8 ng, and a No RT (10 ng) control. Real-time quantitative PCR analyses were performed using the ABI PRISM 7900HT Sequence Detection System (Applied Biosystems). All standards, the no template control ($H_2O$), the No RNA control, the no Reverse Transcriptase control, and the no amplification control (Bluescript plasmid) were tested in six wells per gene (2 wells/plate×3 plates/gene). All samples were tested in triplicate wells each for the 10 ng and 0.8 ng concentrations. The no RT controls were tested in duplicate wells. PCR was carried out with SYBR Green PCR Master Mix (Applied Biosystems) using 2 μl of cDNA and the primers in a 20 μl final reaction mixture. After 2-min incubation at 50° C., AmpliTaq Gold was activated by 10-min incubation at 95° C., followed by 40 PCR cycles consisting of 15s of denaturation at 95° C. and hybridization of primers for 1 min at 55° C. Dissociation curves were generated for each plate to verify the integrity of the primers. Data were analyzed using SDS software version 2.2.2 and exported into an Excel spreadsheet. The actin data were used for normalizing the gene values; i.e., ng gene/ng actin per well. The primer sequences for qRT-PCRs are shown in Table 1.

TABLE 1

| The primer sequences for real-time PCRs | | |
|---|---|---|
| Site I F | ATCCCCTCTATTAATCACATGGAACCTGAT | SEQ ID NO: 13 |
| Site I R | CACTGGCAAAAGAGCTTCTTGTACATAAAG | SEQ ID NO: 14 |
| Site II F | CAAAGCCAGGACTTGACCCTATGGGACACA | SEQ ID NO: 15 |
| Site II R | TAGTGTTAGAAAGAGTTGAGC ATC CTA TCC | SEQ ID NO: 16 |
| Control Site F | CTGGGTGACTTTCTTTAAAAGAGCACTCTT | SEQ ID NO: 17 |
| Control Site R | GCAACGTAAAAACAGAATTCTAGGCCTTTA | SEQ ID NO: 18 |
| mActin F | CATTGCTGACAGGATGCAGAAGG | SEQ ID NO: 19 |
| mActin R | TGCTGGAAGGTGGACAGTGAGG | SEQ ID NO: 20 |
| Hist1 h2ai F | GCGACAACAAGAAGACGCGCAT | SEQ ID NO: 21 |
| Hist1 h2ai R | CTGGATGTTGGGCAGGACGCC | SEQ ID NO: 22 |
| Hist1 h2bl F | AAGAAGGACGGCAAGAAGCGCA | SEQ ID NO: 23 |
| Hist1 h2bl R | CGCTCGAAGATGTCGTTCACGA | SEQ ID NO: 24 |
| Hist1 h3h F | CTGATCCGCAAGCTGCCGTTC | SEQ ID NO: 25 |
| Hist1 h3h R | GTTGGTGTCCTCAAACAGACCC | SEQ ID NO: 26 |

TABLE 1-continued

The primer sequences for real-time PCRs

| | | |
|---|---|---|
| Hist1 h2bm F | GAAGGATGGCAAGAAGCGCAAG | SEQ ID NO: 27 |
| Hist1 h2bm R | CGCTCGAAGATGTCGTTCACGA | SEQ ID NO: 28 |
| Hist1 h4k F | AACATCCAGGGCATCACCAAGC | SEQ ID NO: 29 |
| Hist1 h4k R | GTTCTCCAGGAACACCTTCAGC | SEQ ID NO: 30 |
| Hist1 h2bn F | AAGAAGGACGGCAAGAAGCGCA | SEQ ID NO: 31 |
| Hist1 h2bn R | CGCTCGAAGATGTCGTTCACGA | SEQ ID NO: 32 |
| YACT1 F | GAAAAGATCTGGCATCATACCTTC | SEQ ID NO: 33 |
| YACT1 R | AAAACGGCTTGGATGGAAAC | SEQ ID NO: 34 |
| YHTB1 F | GGTAAGAAGAGAAGCAAGGCTAGAA | SEQ ID NO: 35 |
| YHTB1 R | GACTTCTTGTTATACGCAGCCA | SEQ ID NO: 36 |
| YHTA1 F | TGTCTTGGAATATTTGGCCG | SEQ ID NO: 37 |
| YHTA1 R | TGGATGTTTGGCAAAACACC | SEQ ID NO: 38 |
| YHTB2 F | GTCGATGGTAAGAAGAGATCTAAGG | SEQ ID NO: 39 |
| YHTB2 R | GTGGATTTCTTGTTATAAGCGGC | SEQ ID NO: 40 |
| YHTA2 F | GCTGTCTTAGAATATTTGGCTGC | SEQ ID NO: 41 |
| YHTA2 R | GGCAACAAGTTTTGGTGAATG | SEQ ID NO: 42 |
| YHHT1 F | GCTTTGAGAGAAATCAGAAGATTCC | SEQ ID NO: 43 |
| YHHT1 R | GCAGCCAAGTTGGTATCTTCAA | SEQ ID NO: 44 |
| YHHT2 F | CTGTTGCCTTGAGAGAAATTAGAAG | SEQ ID NO: 45 |
| YHHT2 R | GCAGCCAGATTAGTGTCTTCAAAC | SEQ ID NO: 46 |
| YHHF1 F | TAAAGGTCTAGGAAAAGGTGGTGC | SEQ ID NO: 47 |
| YHHF1 R | TAACAGAGTCCCTGATGACGGATT | SEQ ID NO: 48 |

Native Chromatin immunoprecipitation (ChIP)

As a first step, extensive standardization of pTyr37-H2B antibodies were performed for its usage in ChIP. CHIP was performed using the Active Motif kit as per manufacturer's instructions. For ChIP synchronized MEFs were harvested at 0 and 6.30 hour post thymidine release ($5 \times 10^7$ cells). Cells pellets were lysed in RLB buffer (Mahajan, N. P. et al. (2007) Proc. Nat. Acad. Sci. U.S.A., 104:8438-8443; Mahajan, K. et al. (2010) Prostate, 70:1274-1285) on ice for 10 minutes and sonicated for 25 seconds to shear DNA to an average length of 300-500 bp. The soluble chromatin was incubated overnight at 4° C. with pTyr37-H2B antibody. 20 µl of protein-A agarose was added and the beads were washed sequentially and DNA was eluted. Genomic DNA (Input) was prepared by treating aliquots of chromatin with RNase, proteinase-K followed by ethanol precipitation. Pellets were resuspended and the resulting DNA was quantified on a NanoDrop spectrophotometer. Extrapolation to the original chromatin volume allowed quantitation of the total chromatin yield. An aliquot of chromatin (20-30 µg) was pre-cleared with protein-A agarose beads (Invitrogen). Genomic DNA regions of interest were isolated using pTyr37-H2B antibody. After incubation at 4° C. overnight, protein-A agarose beads were used to isolate the immune complexes. Complexes were washed, eluted from the beads with SDS buffer, and subjected to RNase and proteinase-K treatment and ChIP DNA was purified by phenol-chloroform extraction and ethanol precipitation.

ChIP-on-chip

ChIP and Input DNAs were amplified by whole-genome amplification (WGA) using the GenomePlex WGA Kit (Sigma). The resulting amplified DNAs were purified, quantified, and tested by QPCR at the same specific genomic regions as the original ChIP DNA to assess quality of the amplification reactions. Amplified DNAs were fragmented and labeled using the DNA Terminal Labeling Kit from Affymetrix, and then hybridized to Affymetrix GeneChip Tiling or Promoter arrays at 45° C. overnight. Arrays were washed and scanned, and the resulting CEL files were analyzed using Affymetrix TAS software. Thresholds were selected, and the resulting BED files were analyzed (using Genpathway proprietary software) that provides comprehensive information on genomic annotation, peak metrics and sample comparisons for all peaks (intervals).

Native ChIP-Sequencing and Analysis

The native ChIP was performed as described above. The 0 and 6.30 hrs post thymidine release chromatin immunoprecipitated DNAs were subjected to sequencing. Sequencing yield was very good with almost 40 million reads in each sample, of which 27.7 and 23.6 million for samples 6.30 hr and 0 hr, respectively, mapped uniquely to the mouse mm9 genome.

a. Sequence Analysis:

The 36-nt sequence reads ("tags") identified by the Sequencing Service (using Illumina's Genome Analyzer 2) are mapped to the genome using the ELAND algorithm. Alignment information for each tag is stored in the output file *_export.txt. Only tags that map uniquely, have no more than 2 mismatches, and that pass quality control filtering are used in the subsequent analysis.

b. Determination of Fragment Density:

Since the 5'-ends of the sequence tags represent the end of ChIP/IP-fragments, the tags were extended in silico (using Active Motif software) at their 3'-ends to a length of 110-200 bp, depending on the average fragment length in the size selected library. To identify the density of fragments (extended tags) along the genome, the genome was divided into 32-nt bins and the number of fragments in each bin was determined. This information was stored in a BAR (Binary Analysis Results) file that can be viewed in a browser such as Affymetrix' Integrated Genome Browser (IGB).

c. Interval Analysis ("Peak Finding"):

An Interval is a discrete genomic region, defined by the chromosome number and a start and end coordinate. Intervals represent the locations of fragment density peaks. For each BAR file, Intervals are calculated and compiled into BED files (Browser Extensible Data). A typical threshold setting is in the range of 10-20, but may be adjusted depending on the number of tags sequenced or based on information on positive and negative test sites, independent estimates for the false discovery rate (FDR), and/or the intent to generate a stringent or relaxed analysis. The applied threshold can be found in the Assay Results Report. For an Interval to be called, it must contain 3 consecutive bins with fragment densities greater than the threshold.

d. Alternative and/or Optional Analysis Steps:

1. Tag Normalization: When samples had uneven tag counts, the tag numbers of all the samples were truncated to the number of tags present in the smallest sample.

2. False Peak Filtering: Input or IgG control sample (which represent false peaks) were used to remove corresponding Intervals in ChIP samples, or to mark them as likely false positives.

3. MACS: This alternative, model-based peak finding algorithm (Zhang, Y. et al. (2008) Genome Biol., 9:R137) was used if an Input or IgG control sample was available.

e. Active Region Analysis:

To compare peak metrics between 2 or more samples, overlapping Intervals were grouped into "Active Regions", which were defined by the start coordinate of the most upstream Interval and the end coordinate of the most downstream Interval (=union of overlapping Intervals). In locations where only one sample had an Interval, this Interval defined the Active Region. Active Regions were useful to consider because the locations and lengths of Intervals were rarely exactly the same when comparing different samples.

f. Annotations:

After defining the Intervals and Active Regions, their exact locations along with their proximities to gene annotations and other genomic features were determined and presented in Excel spreadsheets. In addition, average and peak fragment densities within Intervals and Active Regions were compiled.

Pull Down and Filter Binding Assay

Two human histone H2B peptides spanning amino acids 25-49 were synthesized with Tyr37 at middle of the peptide. The sequences are as follows:

H2B(25-49):
(SEQ ID NO: 49)
DGKKRKRSRKESYSVYVYKVLKQVH pY37-H2B(25-49):
(SEQ ID NO: 50)
DGKKRKRSRKESpYSVYVYKVLKQVH

Both the peptides were biotinylated at C-terminus and immobilized on streptavidin-sepharose beads. The beads were incubated with HEK293 cell lysates made in TGN buffer containing 50 mmol/L Tris (pH 7.5), 50 mmol/L Glycine, 150 mmol/L NaCl, 1% Triton X-100, 10% glycerol, phosphatase inhibitors (10 mmol/L NaF, 1 mmol/L $Na_2VO_4$), and protease inhibitor mix (Roche). The beads were extensively washed with TGN buffer and bound NPAT was resolved by SDS-PAGE followed by immunoblotting with NPAT antibodies. Equal loading of peptide was determined by Coomassie blue staining.

NPAT binding to unphosphorylated H2B was confirmed by filter binding assay. Two concentrations of H2B(25-49) or pY37-H2B(25-49) peptides were spotted on nitrocellulose membrane which was incubated with HEK293 cell lysates prepared in TGN buffer. Blot was washed extensively followed by immunoblotting with NPAT antibodies.

Yeast Strains, Culture Conditions and Cell Synchronization

The yeast strains used in this study are pp30-Swe1HA (SWE1HA6-HIS3MX6) and pp30-swe1Δ (SWE1HIS3MX6) (Mollapour, M. et al. (2010) Mol. Cell 37:333-343). WT (MATa (hta1-htb1)Δ:LEU2, (hta2-htb2)Δ: TRP1, his3Δ200 leu2Δ1 ura3-52 trp1Δ63 lys2-128Δ<pZS145-HTA1-Flag-HTB1-HIS3>) and H2B-Y40A mutant of Saccharomyces cerevisiae were obtained (Nakanishi, S. et al. (2008) Nature Struct. & Mol. Biol., 15:881-888). Yeast cells were grown in YPD media at 30° C. for 24 hours. The culture was diluted 1:20 and grown for 1 hour followed by addition of a-factor for 3 hours. Cells were harvested by centrifugation (5000 rpm for 5 min), washed with sterile water and resuspended in fresh media. Cells were harvested at different time points.

Yeast Protein Isolation

S. cerevisiae cells were grown as described above and spheroplasts were obtained as per manufacturer's protocol (Zymo Research). In brief, cells were centrifuged and resuspended in 130 µl digestion buffer containing 5 µl of Zymolyase (5 units/µl). Cells were incubated at 37° C. for 1 hour, spheroplasts were resuspended in RLB buffer (Mahajan, K. et al. (2010) PLoS One, 5:e9646) and sonicated for 10 sec. Lysates were centrifuged (12,000 rpm for 10 min) and supernatants were quantitated followed by immunoblotting or immunoprecipitation.

Yeast RNA Isolation

S. cerevisiae cells were grown and spheroplasts were obtained as described above. The RNAs were isolated using YeaStar RNA kit as per manufacturer's protocol (Zymo Research). To obtain ultra clean RNA that is DNA free, RNAs were passed through Fast-spin columns (DNA-Free RNA kit) as per manufacturer's protocol (Zymo Research). RNAs were quantitated and used for qRT-PCRs.

Yeast FACS Analysis 10 ml of WT and Y40A mutant yeast cells ($1\times10^7$) were harvested at different time points after release from a-factor and washed with water. Collected cells were fixed with 70% ice cold ethanol overnight at −20° C. Next day the tubes were centrifuged, fixative was removed and the cells were resuspended in 1 ml water and centrifuged at 14,000 rpm for 1 min. The cell pellet was resuspended in 0.5 ml 1 mg/ml RNase solution and incubated for 3 hours at 37° C. The cells were collected by centrifugation and resuspended in 0.2 ml protease solution (0.5 mg/ml pepsin) and incubated for 30 minutes at 37° C. The treated cells were collected by centrifugation at 14,000 rpm for 1 minute, the supernatant was discarded and the cell pellet was resuspended in 0.5 ml 50 mM Tris-HCl pH 8.0. 0.1 ml of the cell suspension was transferred to a FACS tube containing 1 ml of 1 µM SYTOX Green staining solution. The cell clumps were dispersed by brief sonication on low power. The cells were analyzed by FLOW cytometry with 488 nm excitation and 523 nm emission. 20,000 events were collected and analysis was carried out using the Modfit software for DNA analysis.

Yeast Histone purification

*S. cerevisiae* cells were grown and spheroplasts were obtained as described earlier. The spheroplasts were resuspended in extraction buffer (Active Motif) and chromatin bound core histones were purified as per manufacturer's instructions. Purified core histones were electrophoresed on 18% SDS-PAGE followed by Coomassie blue staining or immunoblotting with yeast H2B antibodies.

Results

Figure 4A:
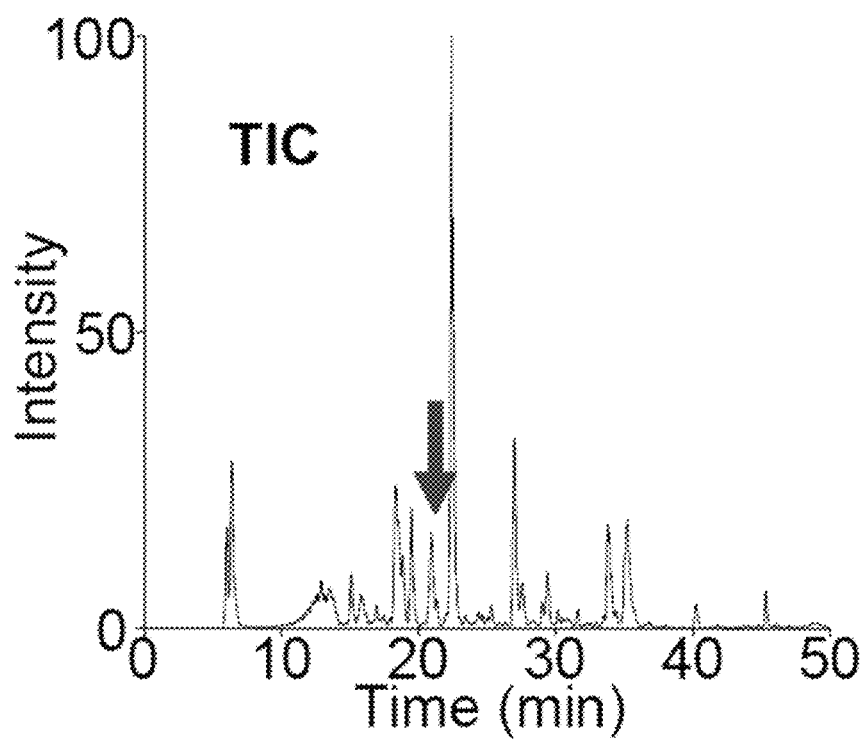
FIG. 4A-4C are histograms identifying the histone H2B Tyr37-phosphorylation site. Histones were purified from HEK293 cells, followed by trypsin/chymotrypsin digestion. The peptide was detected at 21.7 mins in the total ion chromatogram (FIG. 4A) with mass-to-charge ratio 609.2303 (FIG. 4C). The tandem mass spectrum matched the sequence, ESpYSVYVYK (SEQ ID NO:1) indicating that the tyrosine 37 was phosphorylated; the detection of the y6 and y7 is consistent with this localization (FIG. 4C). The assignment was made with Sequest with XCorr 2.34 and ΔCN: 0.27.
Figure 4B:
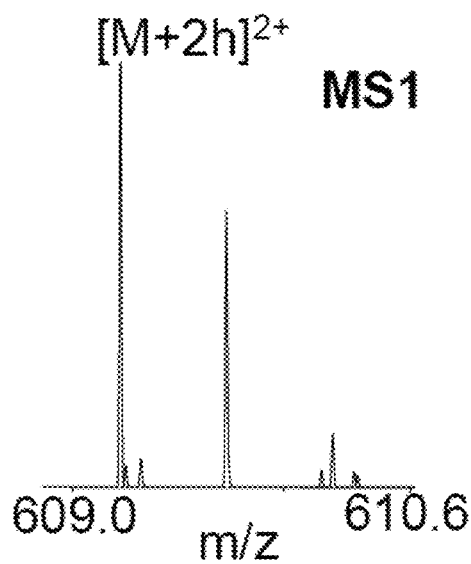
Figure 4C:
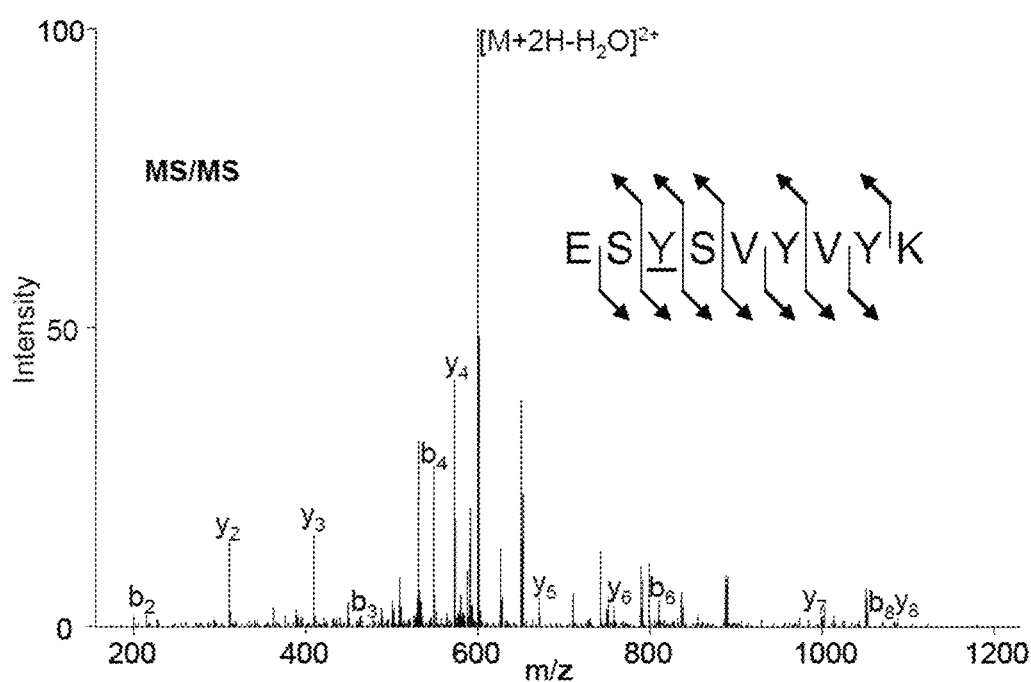
Figure 5A:
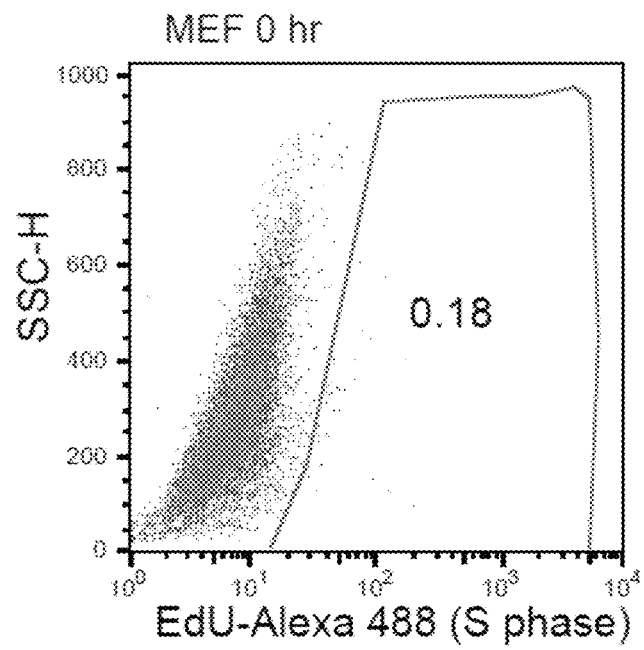
FIG. 5A-5D are flow cytometry plots showing percentage of synchronized MEFs cells in S phase (EdU-Alexa 488 uptake) untreated or after treatment with WEE1 inhibitor harvested at 0 hours or 6.30 hours post-release into the media. EdU was added and cells were harvested 6.30 hours post-release. Cells were fixed and 'Click-it' reaction (Invitrogen) was performed followed by flow cytometry.
Figure 5B:
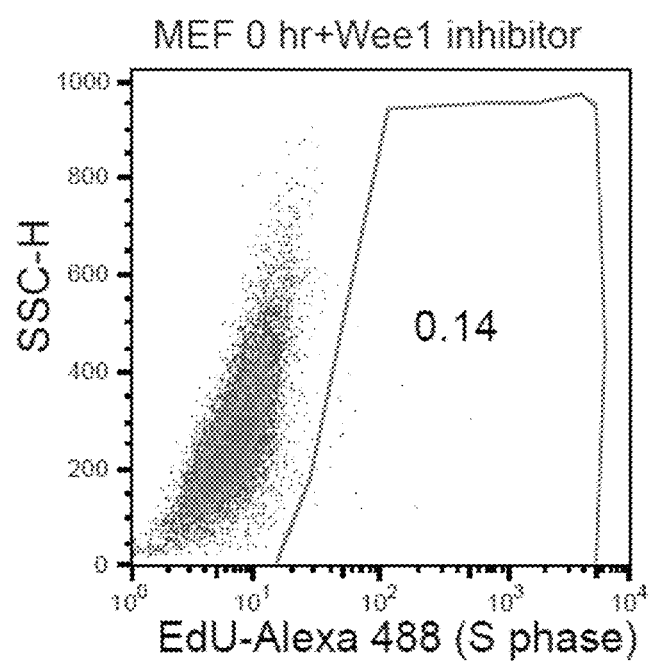
Figure 5C:
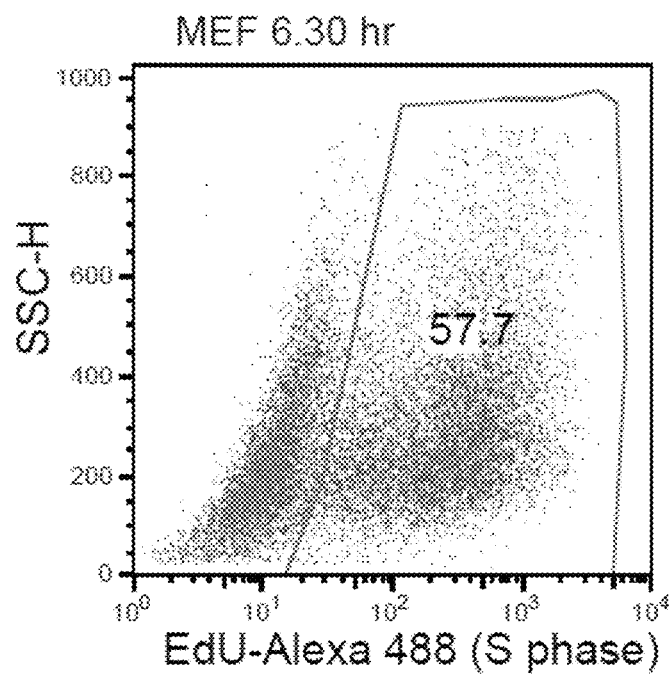
Figure 5D:
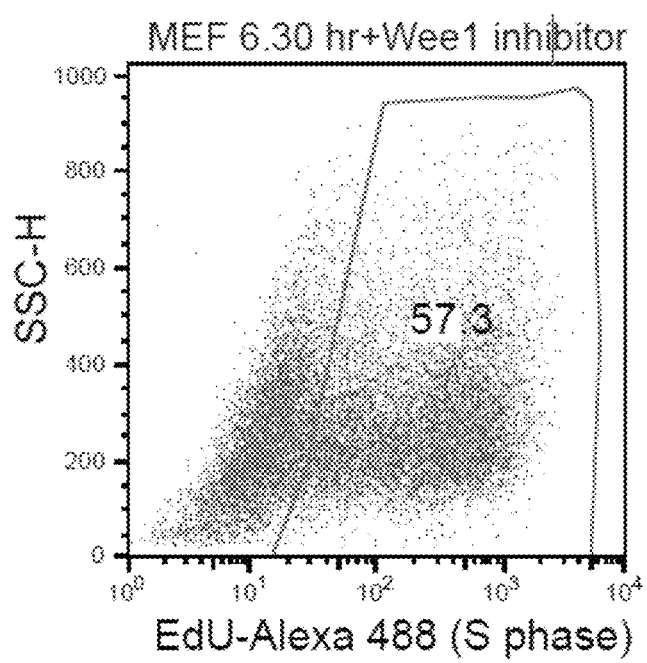
Figure 5E:
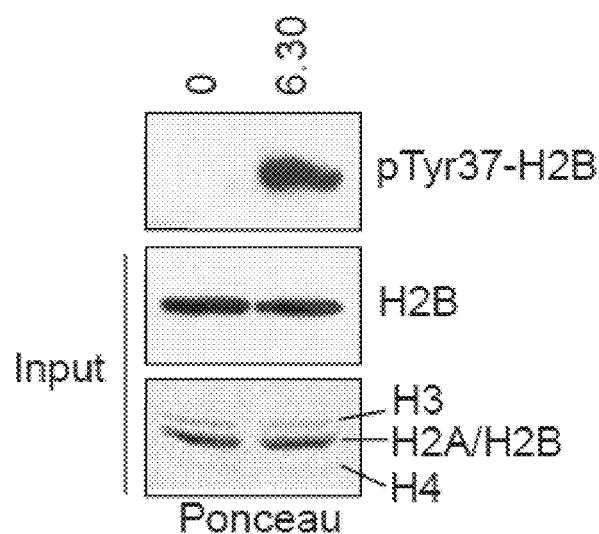
FIG. 5E is an immunoblot showing histones harvested 0 and 6.30 hours post-release from synchronized MEFs and immunoblotted with pTyr37-H2B antibodies (top panel), immunoblotted with H2B antibodies (middle panel), or stained with Ponceau (bottom panel).
Figure 13A:
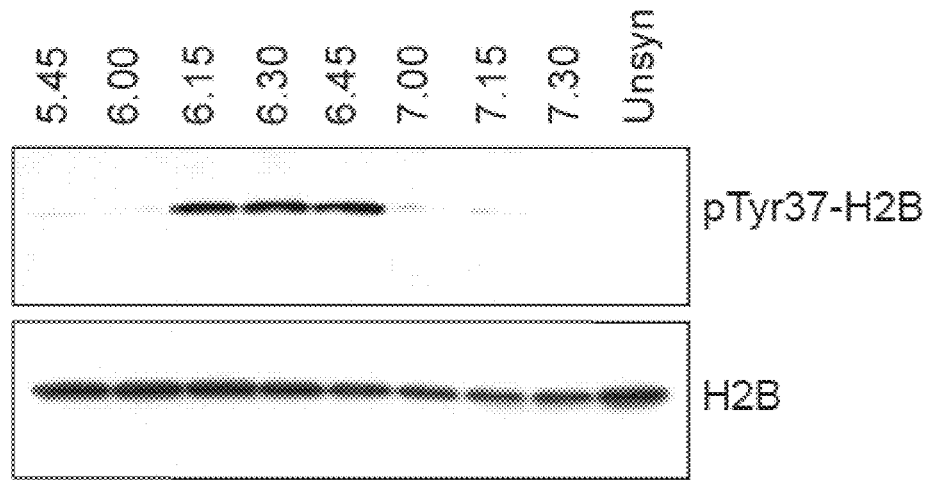
FIG. 13A is an immunoblot showing lysates from synchronized MEFs immunoprecipitated with pTyr37-H2B antibodies followed by immunoblotting with pTyr37-H2B antibody (top panel) or H2B antibody (bottom panel).
Figure 13B:
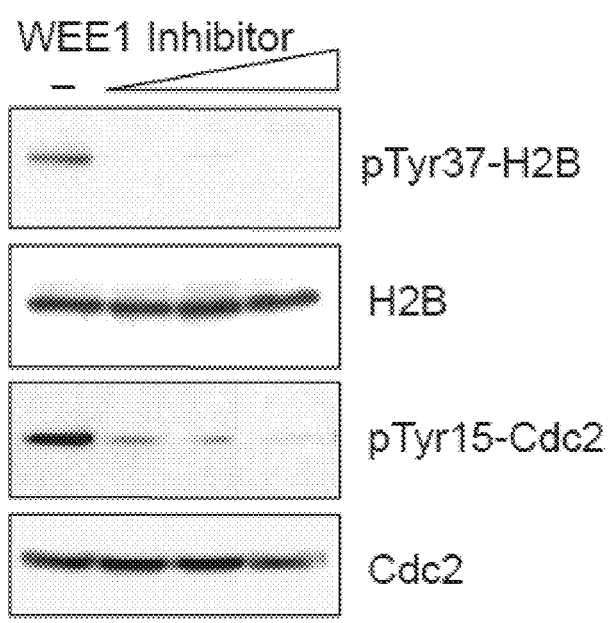
FIG. 13B is an immunoblot showing cell lysates 6.30 hours post-release from H1975 cells synchronized by double thymidine alone (first column) or with 0.31 µM (second column), 0.62 µM (third column) and 1.25 µM (fourth column) MK1775 WEE1 inhibitor that were immunoprecipitated with pTyr37-H2B antibodies followed by immunoblotting with pTyr37-H2B, H2B, pTyr15-Cdc2, or Cdc2 antibodies.
Figure 13C:
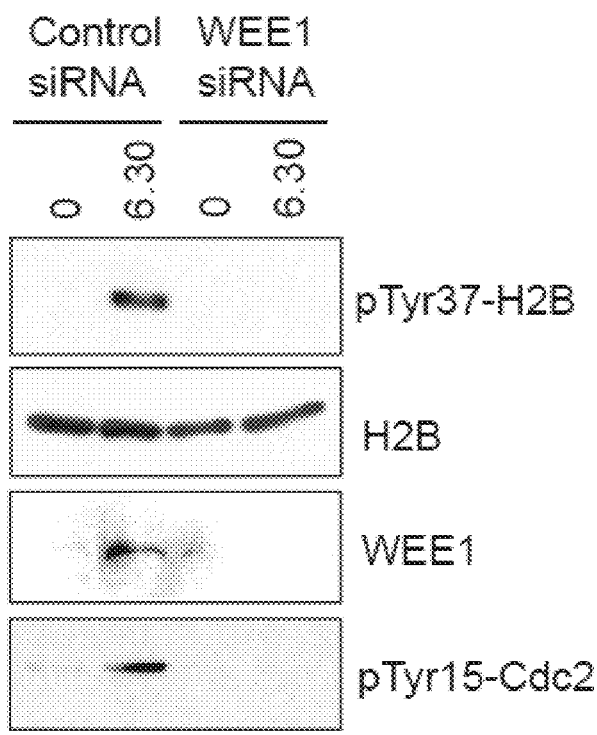
FIG. 13C is an immunoblot showing lysates collected at 0 and 6.30 hours post-release from synchronized MEFs transfected with control (first two columns) or WEE1 (last two columns) siRNAs that were immunoprecipitated with pTyr37-H2B antibodies followed by immunoblotting with pTyr37-H2B (top panel), H2B (second panel), WEE1 (third panel), or PTyr15-Cdc2 (bottom panel) antibodies.
Figure 13D:
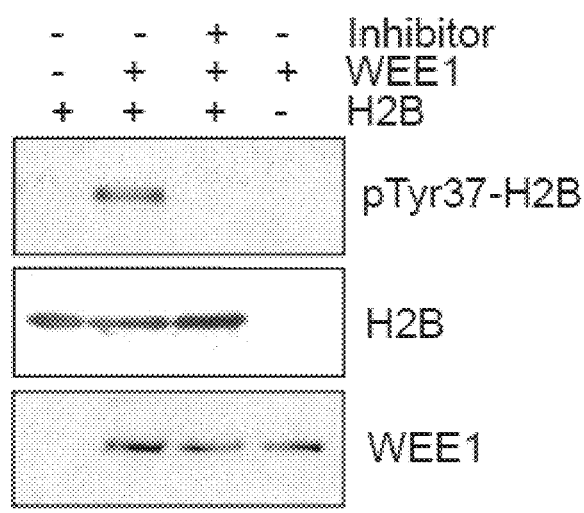
FIG. 13D is an immunoblot showing equimolar amounts of purified WEE1 (last three columns) and H2B (first three columns) proteins incubated in the presence (third column) or absence of WEE1 inhibitor (MK1775, 0.625 µM) for 1 hour at 30° C. and immunoblotted with pTyr37-H2B (top panel), H2B (middle panel), and WEE1 (bottom panel) antibodies.
Figure 13E:
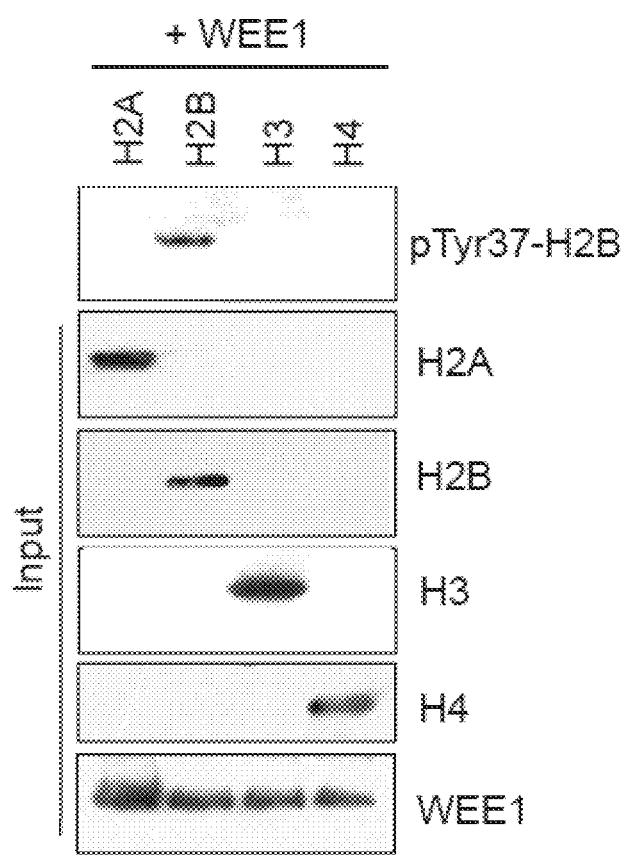
FIG. 13E is an immunoblot showing equimolar amounts of purified WEE1 and H2A (first column), H2B (second column), H3 (third column) or H4 (fourth column) proteins that were either incubated for 1 hour at 30° C. and immunoblotted with pTyr37-H2B (top panel) or immunoblotted with H2A (second panel), H2B (third panel), H3 (fourth panel), H4 (fifth panel), or WEE1 (sixth panel) antibodies.
Figure 13F:
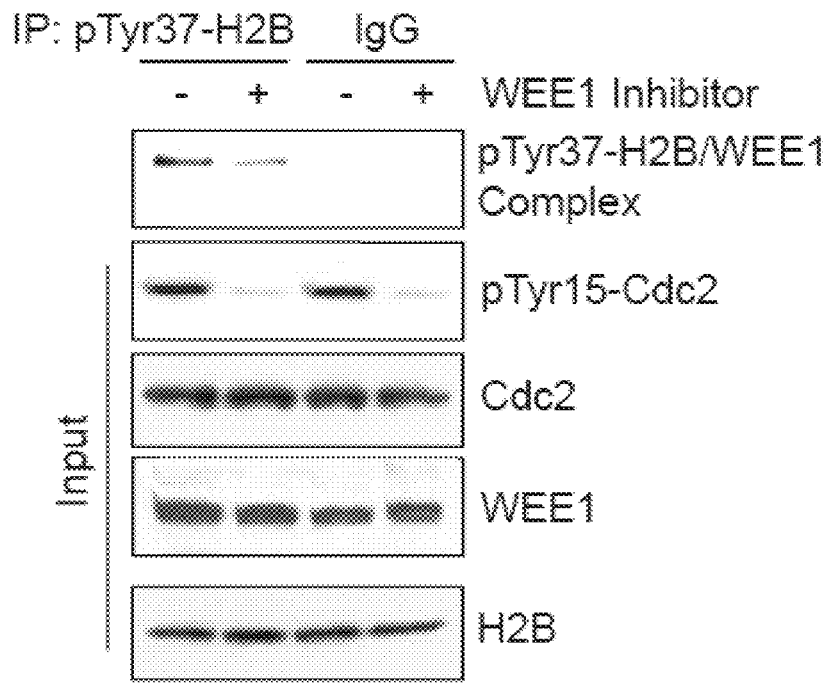
FIG. 13F is an immunoblot showing lysates from MEFs untreated (first and third columns) or treated (second and fourth columns) with WEE1 inhibitor (0.625 µM, 14 hour) that were either immunoprecipitated with pTyr37-H2B antibodies and immunoblotted with WEE1 antibodies (top panel) or immunoblotted with pTyr37-Cdc2 (second panel), Cdc2 (third panel), WEE1 (fourth panel), or H2B (fifth panel) without immunoprecipitation.
Figure 13G:
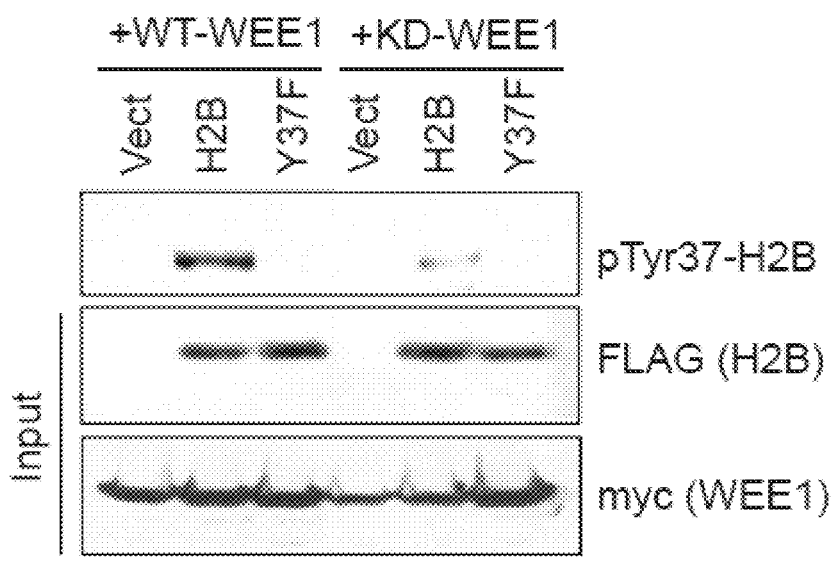
FIG. 13G is an immunoblot showing lysates from MEFs co-expressing Myc-tagged WEE1 (WT, first three columns) or KD mutant WEE1 (last three columns) and either vector (first and third columns), FLAG-tagged H2B (second and fifth columns) or Y37F mutant H2B (third and sixth columns) that were serum-starved 24 hrs and either immunoprecipitated with pTyr37-H2B antibodies and immunoblotted with FLAG antibody (top panel) or immunoblotted with anti-FLAG antibodies (middle panel) or anti-myc antibodies (bottom panel) without immunoprecipitation.
Figure 14:
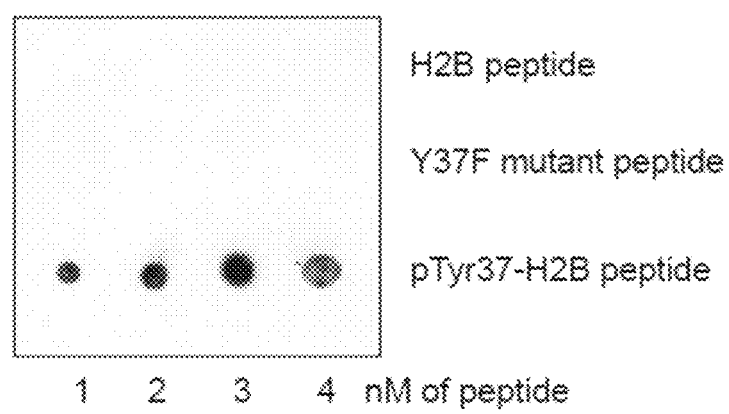
FIG. 14 is an immunoblot of 1 nM (column 1), 2 nM (column 2), 3 nM (column 3), or 4 nM (column 4) H2B peptide spanning Tyr37 (Tyr37-H2B; SRKESYSVYVYK, SEQ ID NO:59; top row), the same peptide phosphorylated at Tyr37 (pTyr37-H2B; SRKESpYSVYVYK, SEQ ID NO:60; bottom row), or the same peptide with a Tyr37-to-Phe mutation (SRKESFSVYVYK, SEQ ID NO:61; middle row) immunoblotted with pTyr37-H2B antibody.
Figure 15A:
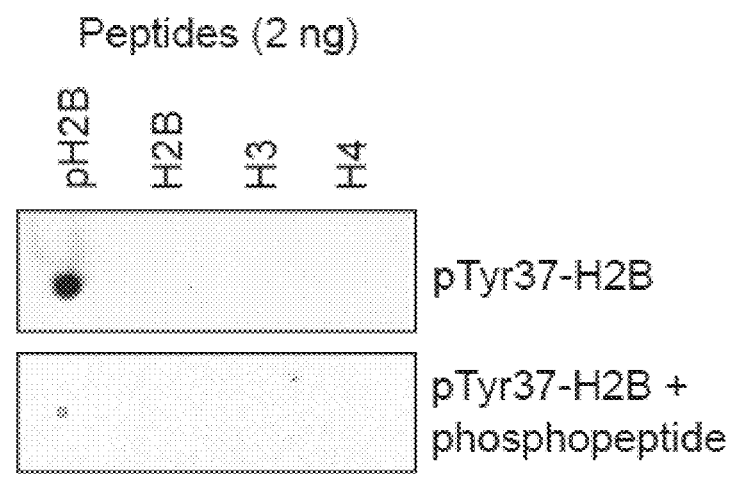
FIG. 15A is an immunoblot of pTyr37-H2B phosphopeptide (column 1), Tyr37-H2B peptide (column 2), non-specific H3 derived peptide (column 3), and H4 derived peptide (column 4) immunoblotted with pTyr37-H2B antibody (top panel) or pTyr37-H2B antibody pre-incubated with the Tyr37-H2B phosphopeptide (bottom panel).
Figure 15B:
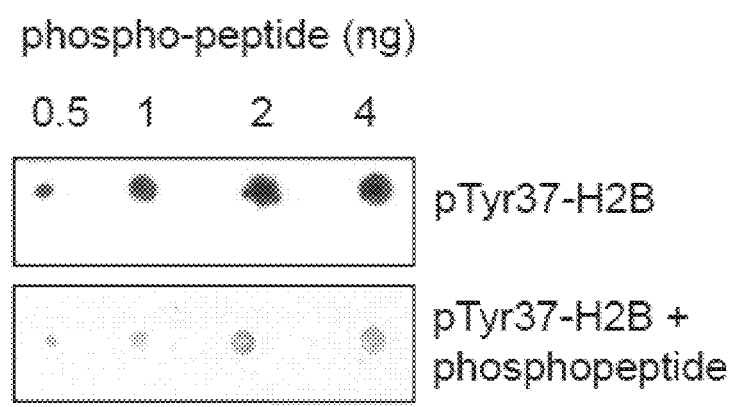
FIG. 15B is an immunoblot of 0.5 ng (column 1), 1 ng (column 2), 2 ng (column 3), and 4 ng (column 4) pTyr37-H2B phosphopeptide immunoblotted with pTyr37-H2B antibody (top panel) or pTyr37-H2B antibody pre-incubated with the Tyr37-H2B phosphopeptide (bottom panel).
Figure 16:
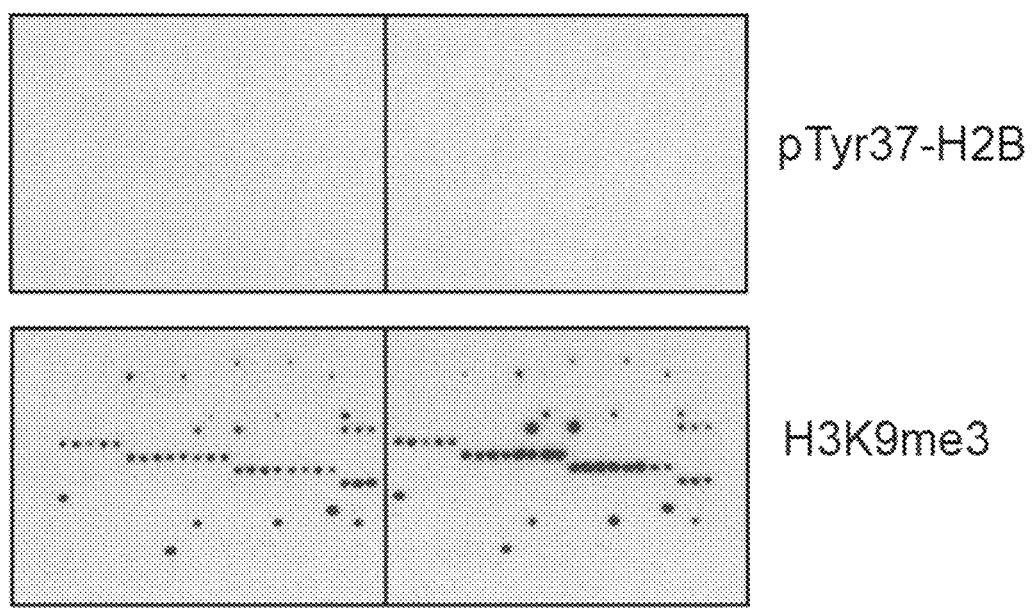
FIG. 16 is an immunoblot of 384 unique histone modification combinations (MODified™ Histone Peptide Array, Active Motif, Inc.) immunoblotted with pTyr37-H2B (top panel) or H3K9me3 antibodies (bottom panel).

The decoration of histones by post-translational modifications (PTM), including acetylation, phosphorylation, methylation, ubiquitylation and SUMOylation has emerged as a major regulatory mechanism of temporal gene expression (Berger, S. L. (2007) Nature, 447:407-412). To delineate functional consequences of histone tyrosine phosphorylation, purified histones were subjected to mass spectrometry based PTM identification. Phosphorylation at tyrosine 37 in histone H2B was identified (FIGS. 4A-4C). Since the functional role of Tyr37-phosphorylated H2B (pTyr37-H2B) was unknown, phospho-antibodies were raised against pTyr37-H2B and extensively validated (FIGS. 13C-13E, 13G, 14-16, 18). Recognition of peptides by pTyr37-H2B antibodies were compared and it was observed that only the H2B phosphopeptide that was phosphorylated at Tyr37 was recognized whereas the non-phosphorylated H2B peptide or H2B harboring a Tyr37 to Phe (Y37F) substitution was not reactive (FIG. 14). Further, competition of pTyr37-H2B antibodies with phosphopeptide resulted in almost complete loss of recognition of pTyr37-H2B phosphopeptides (FIG. 15). Moreover, pTyr37-H2B antibodies were screened for cross-reactivity against 59 distinct acetylation, methylation, phosphorylation, and citrullination modifications on core histones using Histone Peptide Arrays. The pTyr37-H2B antibody did not cross-react with any of these PTMs, however when the same blots were hybridized with H3K9me3 antibodies, it revealed expected pattern of hybridization (FIG. 16). Collectively, these data indicate that the antibodies are selective for pTyr37-phosphorylation on histone H2B.

Mass spectrometry based analysis revealed that in asynchronously growing cultures, pTyr37-H2B levels are 0.21% of total H2B protein (Table 2), which indicated that H2B is Tyr-phosphorylated transiently during cell cycle followed by rapid dephosphorylation. NMC refers to a trypsin missed cleavage at the N-terminus of the peptide. 1+ and 2+ refer to the charge of the peptide. Sequest database search scores e.g. XCorr and delta CN score are shown.

TABLE 2

Mass spectrometry based analysis in asynchronously growing cultures

|  | Sequence | XCore score | Delta CN score | m/z | Peptide precursor mass |
| --- | --- | --- | --- | --- | --- |
| H2B-Y37 | (K)ESYSVYVYK(V) (SEQ ID NO: 51) | 1.81 | 0.4506 | 569.276 | 1,136.54 |
| H2B-Y37-NMC_1+ | (R)KESYSVYVYK(V) (SEQ ID NO: 52) | 2.05 | 0.2016 | 1,265.64 | 1,264.64 |
| H2B-Y37-NMC_2+ | (R)KESYSVYVYK(V) (SEQ ID NO: 53) | 3.37 | 0.4804 | 633.3239 | 1,264.63 |
| H2B-pY37 | (K)ESySVYVYK(V) (SEQ ID NO: 54) | 2.34 | 0.2713 | 609.2303 | 1,216.44 |

|  | Charge | delta mass | delta ppm | peptide start position | peptide stop position | Peak Area |
| --- | --- | --- | --- | --- | --- | --- |
| H2B-Y37 | 2 | -0.00248 | -2.18 | 36 | 44 | 451415266 |
| H2B-Y37-NMC_1+ | 1 | 0.001518 | 1.199 | 35 | 44 | 9699792 |
| H2B-Y37-NMC_2+ | 2 | -0.00166 | -1.309 | 35 | 44 | 217955845 |
| H2B-pY37 | 2 | -0.06024 | -49.48 | 36 | 44 | 1490065 |
| % of pY37 |  |  |  |  |  | 0.218946585 |

Figure 17:
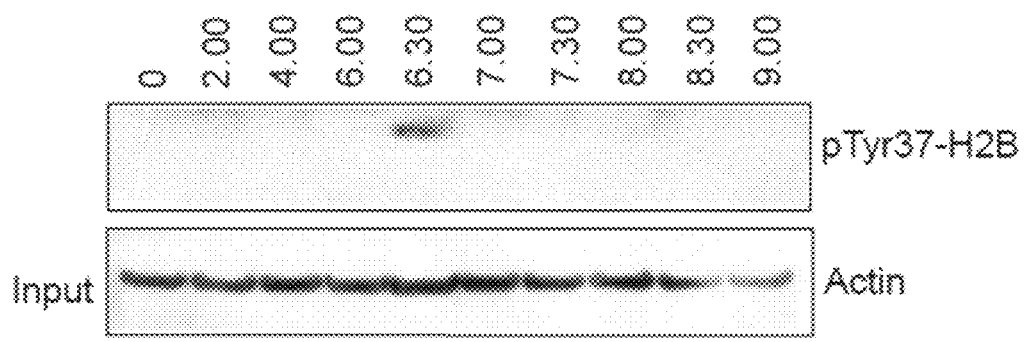
FIG. 17 is an immunoblot of lysates from synchronized MEFs immunoprecipitated with pTyr37-H2B antibodies and immunoblotted with pTyr37-H2B (top panel) or actin (bottom panel) antibodies.
Figure 18:
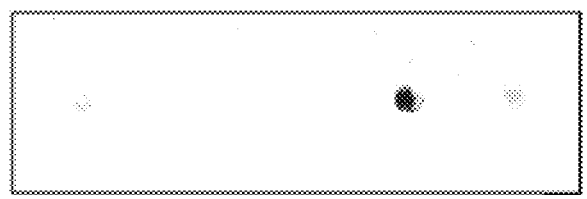
FIG. 18 is an immunoblot of equimolar amounts of purified WEE1 (first, fourth, and fifth columns), Tyr37-H2B peptide (third and fourth columns), and/or Tyr37-to-Phe mutant peptide (first and second columns) that were incubated for 30 min at 30° C., spotted on nitrocellulose membrane, and immunoblotted with pTyr37-H2B antibody.
Figure 19:
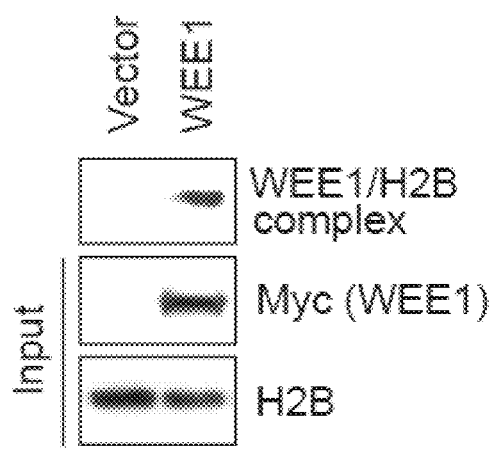
FIG. 19 is an immunoblot of lysates from HEK293T cells transfected with myc-tagged WEE1 expressing construct (column 2) or empty vector (column 1) and either immunoprecipitated with anti-myc antibodies and then immunoblotted with H2B antibodies (top panel) or immunoblotted with anti-myc antibodies (middle panel) or H2B antibodies (bottom panel) without immunoprecipitation.

To assess cell cycle specific pTyr37-phosphorylation of H2B, mouse embryo fibroblasts (MEFs) were synchronized by double thymidine, released in fresh media and aliquots were collected at different time intervals. The pTyr37-H2B was detected at 6.15-6.45 hours post-release, peaking at 6.30 hours post-release (FIGS. 13A, 17). Synchronized H1975, a human lung cancer cell line also showed H2B pTyr37-phosphorylation 6.30 hours post thymidine release. EdU-incorporation assay of 6.30 hours post-release cells revealed that significant proportion of these cells were in S phase (FIG. 5). During S phase, temporal regulation of WEE1 kinase expression and tyr-phosphorylation of its substrate, Cdc2 is well established (Russell, P. et al. (1987) Cell, 49:559-567; Heald, R. et al. (1993) Cell, 74:463-474; Lundgren, K. et al. (1991) Cell, 64:1111-1122; McGowan, C. H. et al. (1995) The EMBO Journal, 14:2166-2175). To examine whether H2B is a WEE1 kinase substrate, cells were treated with increasing concentrations of WEE1 inhibitor, MK-1775 (Hirai, H. et al. (2009) Mol. Cancer Ther., 8:2992-3000). Even a 0.3 µM concentration of WEE1 inhibitor treatment resulted in complete loss of pTyr37-phosphorylation of H2B (FIG. 13B). Similarly, transfection of cells with WEE1 siRNA resulted in complete loss of H2B pTyr37-phosphorylation (FIG. 13C). To test whether WEE1 directly phosphorylates H2B, in vitro kinase assay (Mahajan, K. et al. (2010) PLoS One, 5:e9646) was performed. When purified WEE1 and H2B were incubated, H2B was Tyr37-phosphorylated, however, WEE1 inhibitor abrogated H2B pTyr37-phosphorylation (FIG. 13D). Further, WEE1 phosphorylated H2B peptide, however, Y37F mutant peptide was not phosphorylated (FIG. 18). Moreover, WEE1 specifically phosphorylated H2B and failed to phosphorylate other three core histones, H2A, H3 and H4 (FIG. 13E). Co-immunoprecipitation experiment revealed that WEE1 binds to endogenous H2B (FIG. 19) and phosphorylates it as seen by WEE1/pTyr37-H2B complex formation (FIG. 13F). To further validate H2B as a substrate for WEE1 kinase in vivo, FLAG-tagged H2B and Y37F mutant-H2B expressing constructs were generated. Coexpression with wild-type (WT) WEE1 or kinase dead (KD)-WEE1 kinase revealed that the WT-WEE1 specifically phosphorylated H2B but failed to phosphorylate Y37F mutant (FIG. 13G). Collectively, these data indicate that WEE1 kinase specifically phosphorylates H2B at Tyr37.

To identify regions in chromatin where H2B Tyr37-phosphorylation occurs, this study performed native ChIP-coupled DNA microarray analysis (ChIP-on-chip) (Kim, T. H. et al. (2005) Nature, 436:876-880) and native ChIP-sequencing. The sheared chromatin from synchronized MEFs (0 and 6.30 hours post-release) was immunoprecipitated using a pTyr37-H2B antibody followed by sequencing. It lead to the identification of 3524 potential sites/regions where pTyr37-H2B is present in mouse genome; 1240 of which were present within genes while 351 sites were present upstream and 326 sites were downstream of genes. ChIP-on-chip revealed two pTyr37-H2B-containing sites, named here as Site I and II, upstream of histone encoding genes, the histone cluster 1 or Hist1, opening an intriguing possibility of histone expression regulation by modified histone itself.

The genes for the five histones H1/H2A/H2B/H3/H4 are clustered together in the genome in all metazoans. There are 10-20 functional copies of the genes for each of the histone proteins and each individual gene encodes a small fraction of the total histone protein. In mammals there are two loci, each containing multiple histone genes. The largest cluster, HIST1, is located on chromosome 6 in humans and chromosome 13 in mice (Albig, W. et al. (1997) Human Genetics, 101:284-294; Albig, W. et al. (1997) Genomics, 40:314-322; Wang, Z. F. et al. (1996) Genome Research, 6:688-701). The mouse and human histone gene clusters have strikingly similar gene numbers and organization. The mouse Hist1 cluster contains majority of histone coding genes, i.e., 45 core histone genes and 6 histone H1 genes (Marzluff, W. F. et al. (2002) Genomics, 80:487-498). The histone genes in the Hist1 cluster are arranged in three subclusters. About a third of histone genes, closest to site I and II are located in Subcluster 1 (FIG. 1A), some of these genes have been analyzed in this study.

Figure 1B:
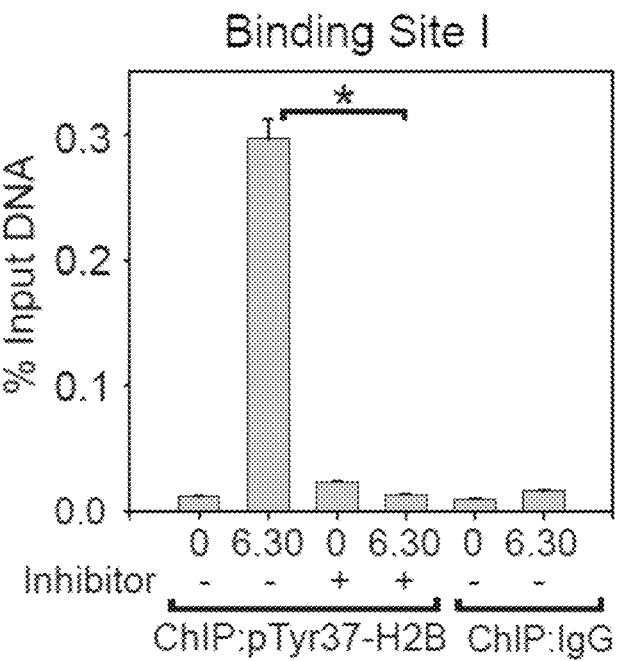
FIG. 1B-1D are bar graphs showing Native Chromatin immunoprecipitation (ChIP) (% input DNA) in synchronized MEFs treated with WEE1 inhibitor or untreated and harvested at 0 and 6.30 hours post-release. Native ChIP was performed using pTyr37-H2B or IgG antibodies followed by quantitative PCR using primers corresponding to Site I (FIG. 1B), Site II (FIG. 1C) and control site (FIG. 1D). Data shown are representative of three independent experiments. *p=0.001; p=0.006.
Figure 1C:
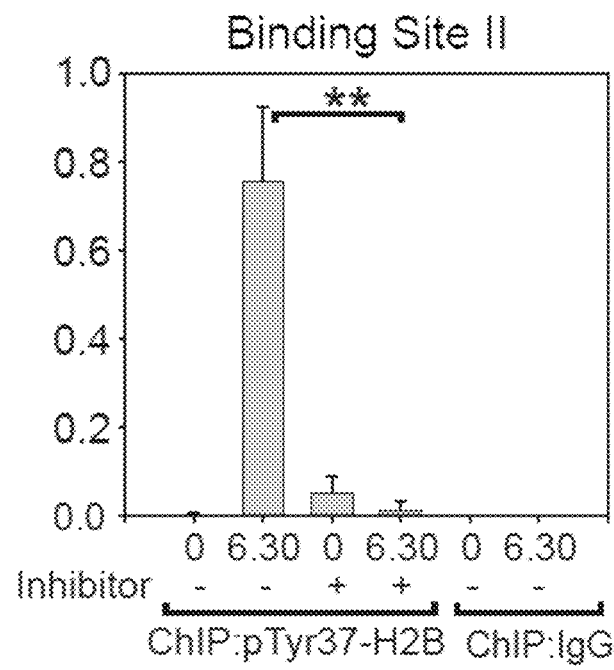
Figure 1D:
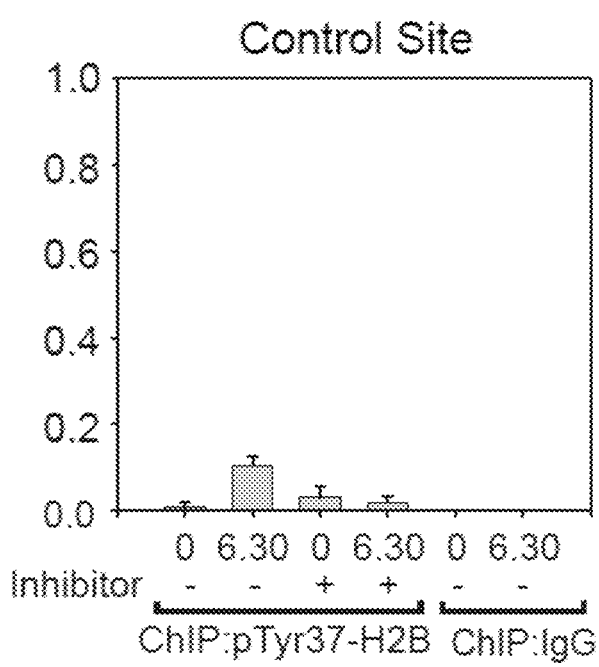
Figure 1E:
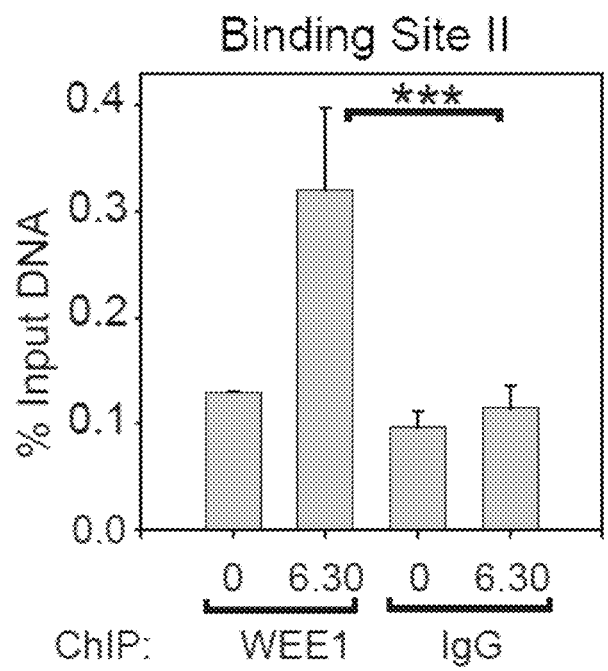
FIG. 1E is bar graph showing ChIP in synchronized MEFs harvested at 0 and 6.30 hours post-release using WEE1 or IgG antibodies followed by quantitative PCR using primers corresponding to Site II. Data shown are representative of three independent experiments. *p=0.02.
Figure 1F:
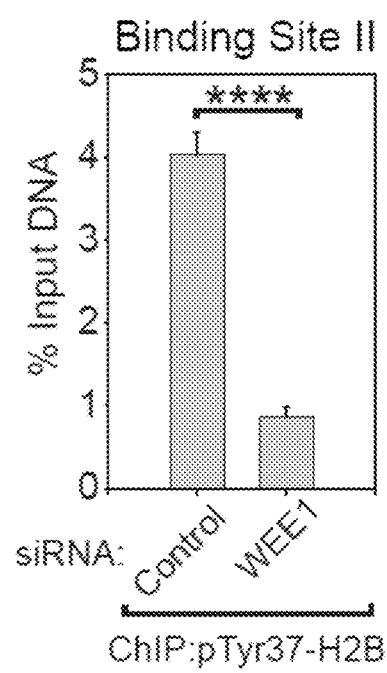
FIG. 1F is bar graph showing ChIP in cells transfected with control or WEE1 siRNAs performed using pTyr37-H2B antibodies followed by quantitative PCR using primers corresponding to Site II. Data shown are representative of three independent experiments. ****p=0.001.

To validate the presence of pTyr37-H2B upstream of the Hist1 cluster, sheared chromatin from synchronized MEFs (0 and 6.30 hours post-release) was immunoprecipitated using the pTyr37-H2B antibody followed by quantitative polymerase chain reaction or ChIP-qPCR (Mahajan, K. et al. (2010) Prostate, 70:1274-1285). It revealed that pTyr37-H2B is present at both the sites, site I and II, however, upon WEE1 inhibitor treatment, occurrence of pTyr37-H2B at these sites was significantly reduced (FIGS. 1B and 1C). Presence of pTyr37-H2B appears to be specific for site I and II, because pTyr37-H2B was not detected within the Hist1 gene cluster (control site, FIG. 1D). To assess whether WEE1 regulates H2B Tyr37-phosphorylation upstream of the Hist1 cluster, ChIP-qPCR was performed using WEE1 antibodies. The amount of WEE1 at site II was significantly increased in 6.30 hours post-release MEFs (FIGS. 1E and 13A). To further validate the role of WEE1, cells were transfected with WEE1 or control siRNAs and ChIP-qPCR was performed using pTyr37-H2B antibodies. Significant decrease in site II specific ChIP-DNA was observed in WEE1 siRNA transfected sample as compared to the control siRNA transfected sample (FIG. 1F), indicating a functional, WEE1 kinase-dependent pTyr37-H2B association with the Hist1 gene cluster.

Figure 2A:
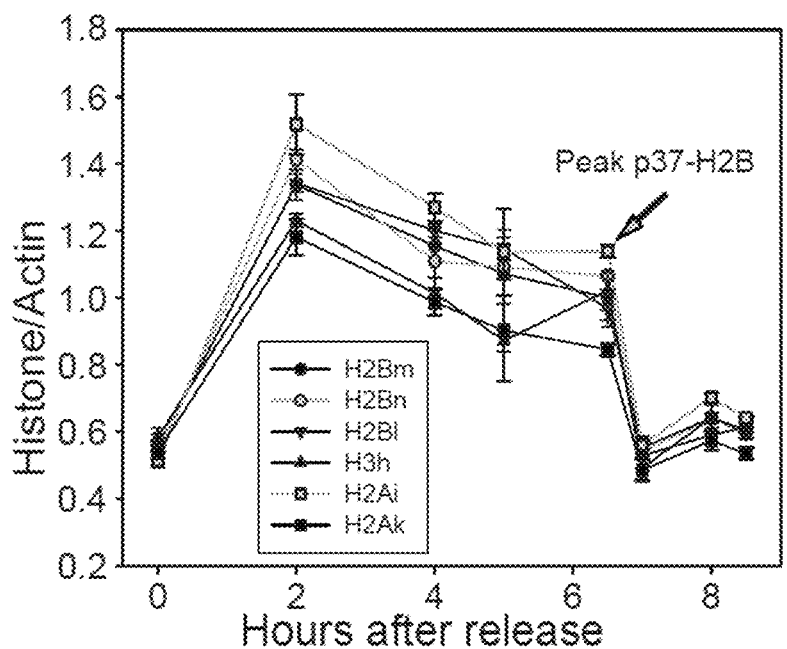
FIG. 2A is a graph showing synchronized histone RNA levels (relative to actin) in MEFs harvested at 0, 2, 4, 5, 6.30, 7, 8, and 8.30 hours post-release. Total RNA was prepared followed by quantitative RT-PCR for H2Bl, H2Ai, H3 h, H2Bm, H2Ak and H2Bn transcripts. Data are representative of three independent experiments.
Figure 2B:
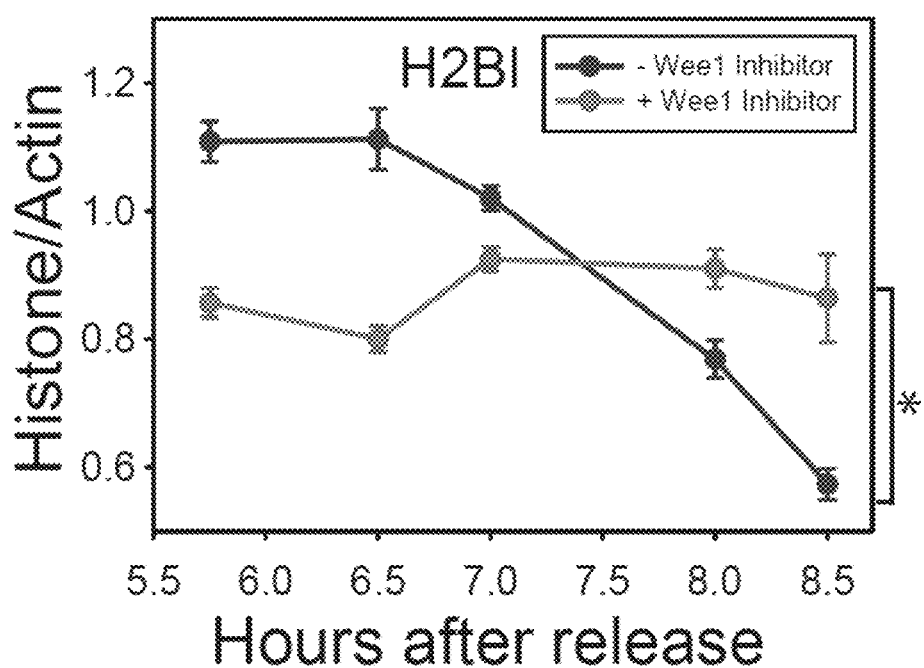
Figure 2C:
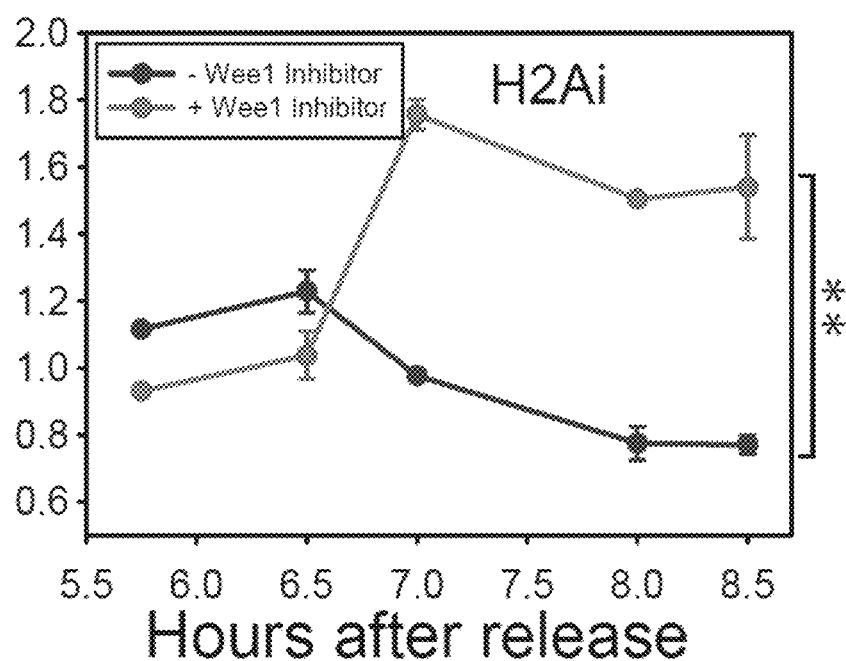
Figure 2D:
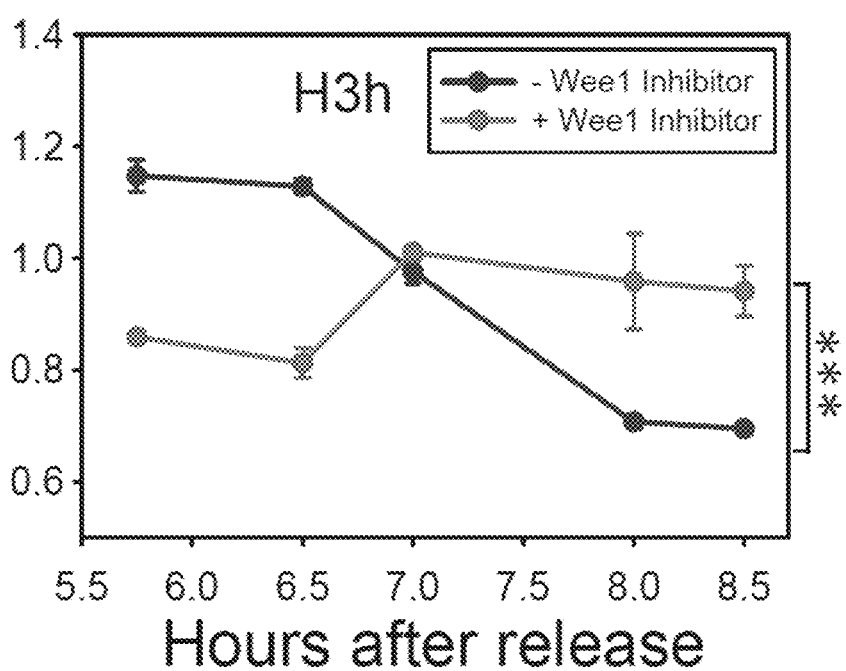
Figure 2E:
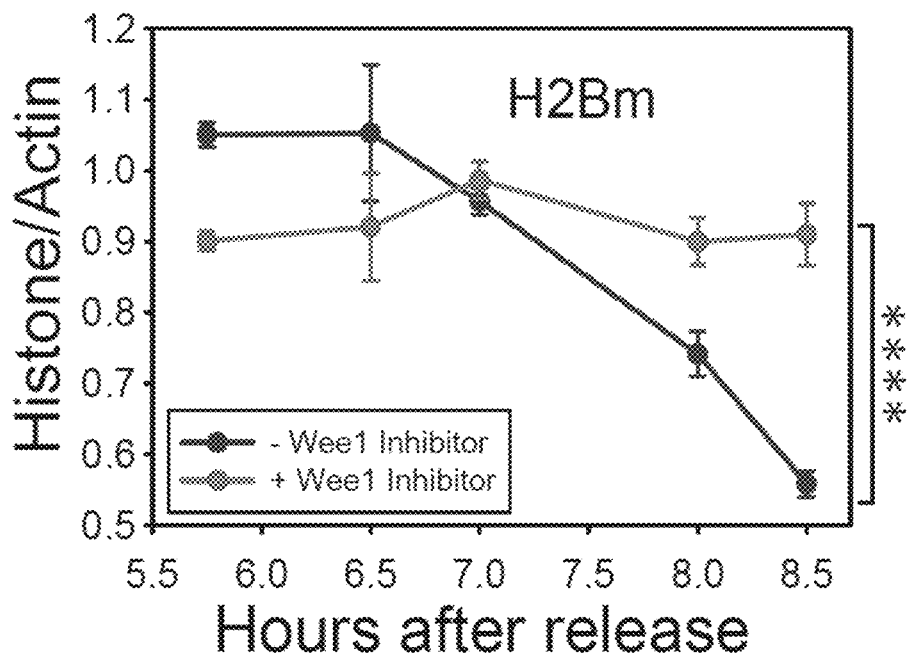
Figure 2F:
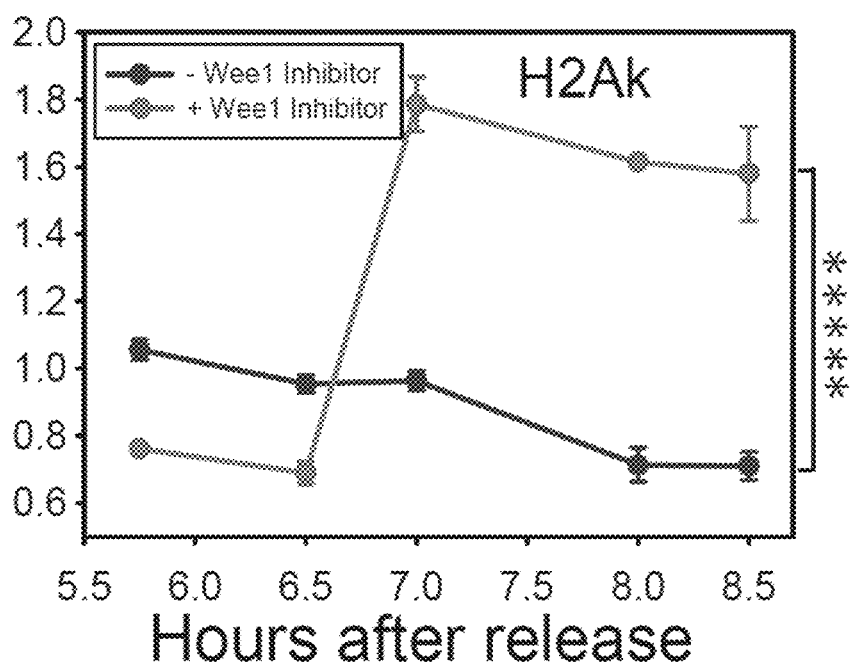

Modification of core histones has been demonstrated to regulate transcription (Berger, S. L. (2007) Nature, 447:407-412; Laribee, R. N. et al. (2007) Genes & Development, 21:737-743), however, transcription of histone themselves were not known to be regulated by histone phosphorylation. Expression of histone RNA was assessed in synchronized MEFs demonstrating that core histone RNA levels peaked within 2 hours post-release. However, at 6.30 hours post-release, when H2B is Tyr37-phosphorylated, a sharp decline was observed (FIG. 2A). To investigate whether pTyr37-H2B plays a direct role in regulating histone gene transcription, synchronized MEFs were treated (or untreated) with WEE-1 specific inhibitor. Total RNA was isolated and qRT-PCR was performed. In untreated cells, rapid decrease in transcripts of multiple core histone genes was observed after 6.30 hours post-release (FIGS. 2B-2G). However, upon WEE1 inhibitor treatment, histone mRNA levels did not decrease after 6.30 hours post-release; instead, a significant increase was observed (FIGS. 2B-2G, compare 8.30 hours post-release). These data indicate that pTyr37-H2B phosphorylation may have repressive effect on transcription of core histone genes located in Hist1 cluster.

Figure 3B:
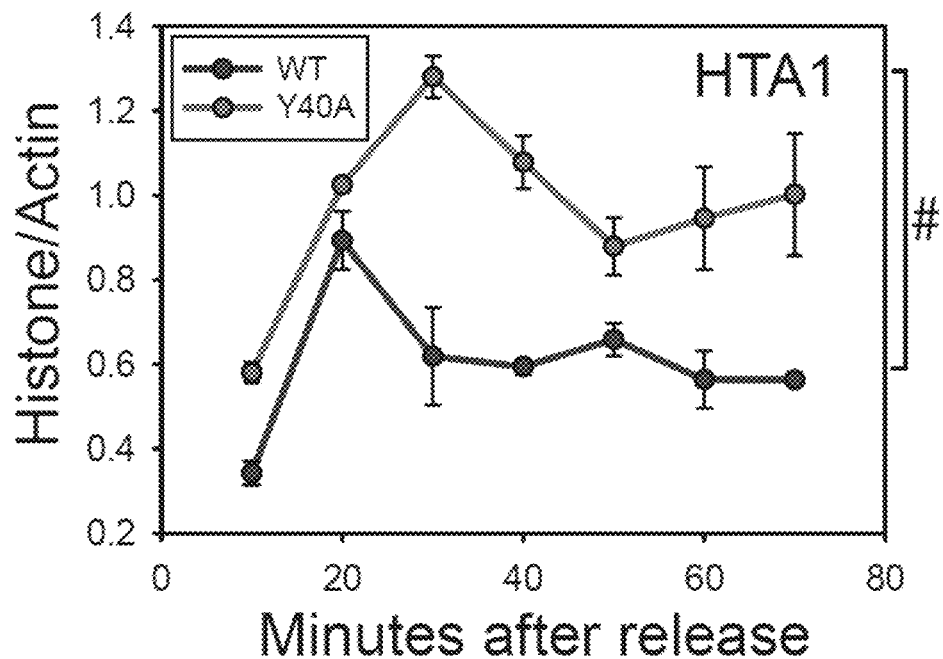
FIG. 3B-3F are graphs showing histone RNA (relative to actin) in wildtype (WT) and Y40A mutant yeast cells treated with α-factor for 3 hours, washed and harvested at indicated time points post-release. Total RNA was prepared followed by qRT-PCR for histones transcripts. FACS analysis of yeast cells was performed to determine exit of cells from G0 stage (0 minutes) and entry into cell cycle. Data are representative of three independent experiments. The p values for 30 minutes are as follows: #p=0.024; ##p=0.008; ###p=0.0083; ####p=0.037.
Figure 3C:
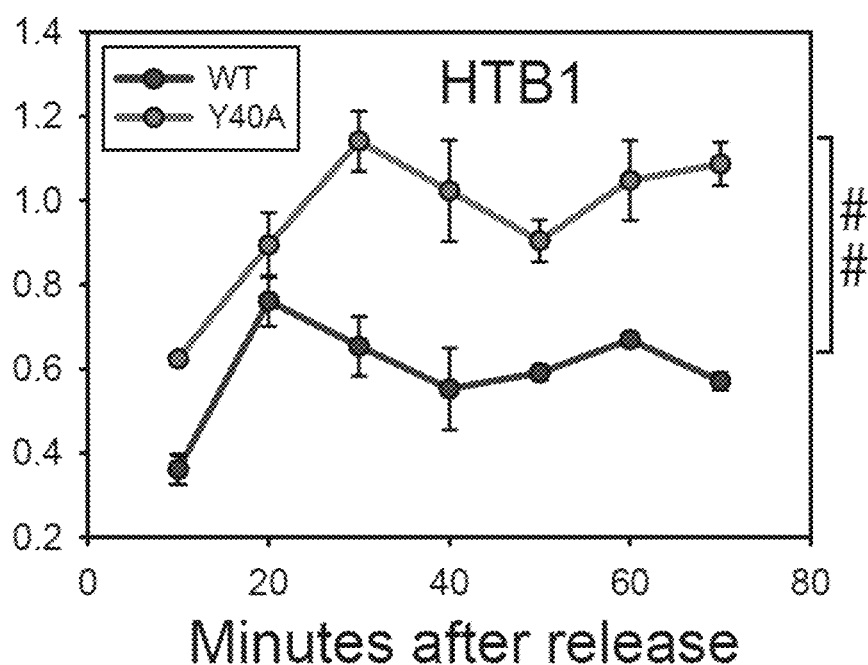
Figure 3D:
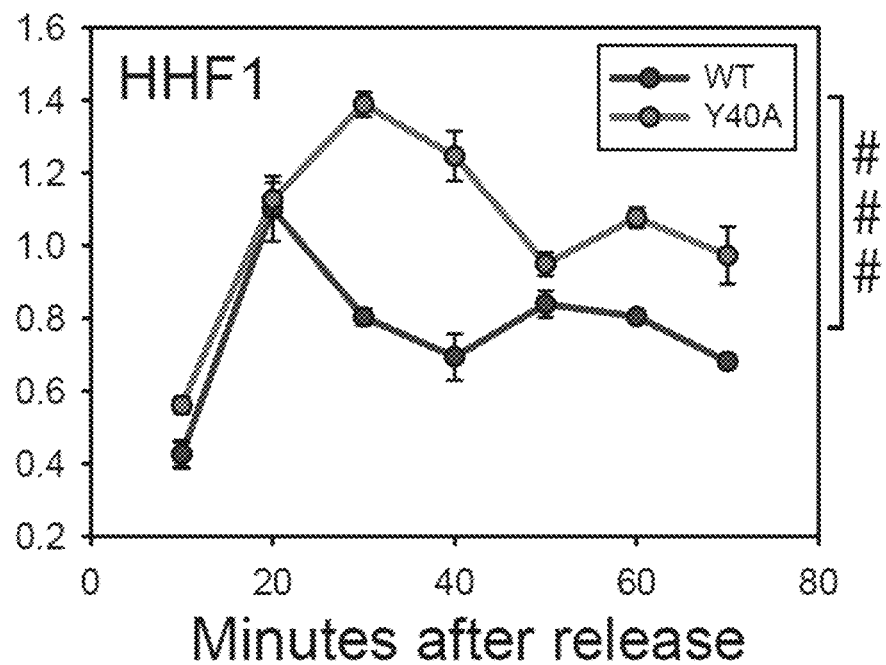
Figure 3E:
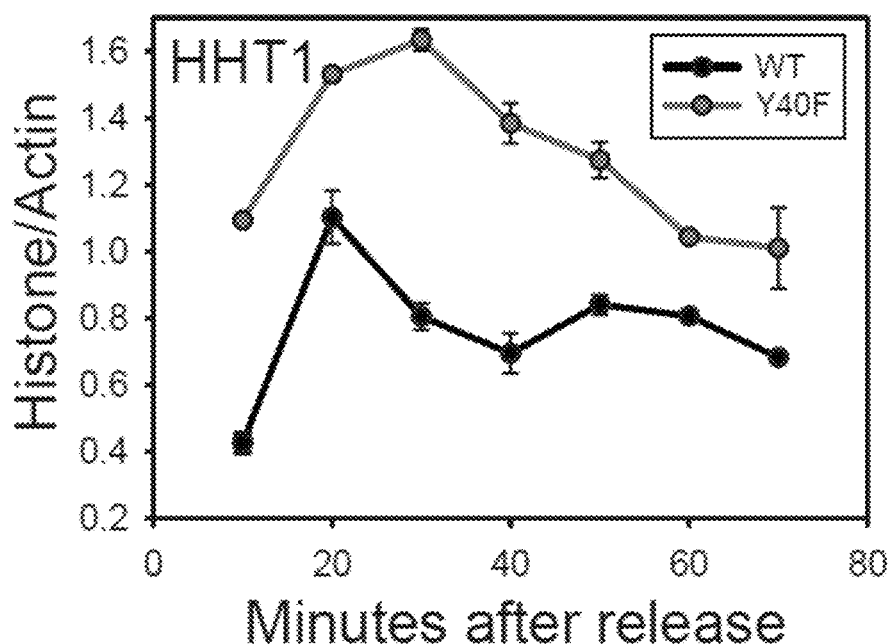
Figure 3F:
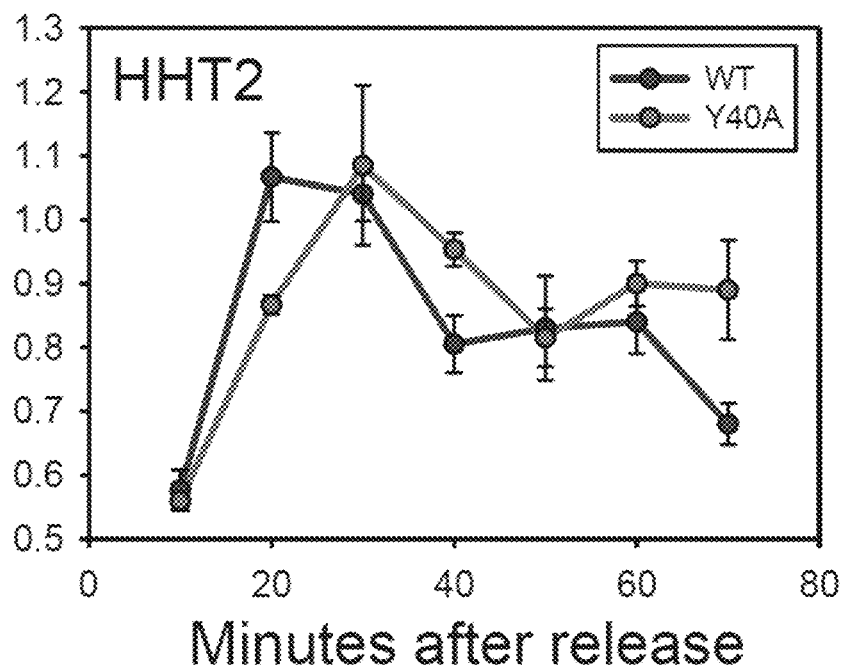
Figure 3G:
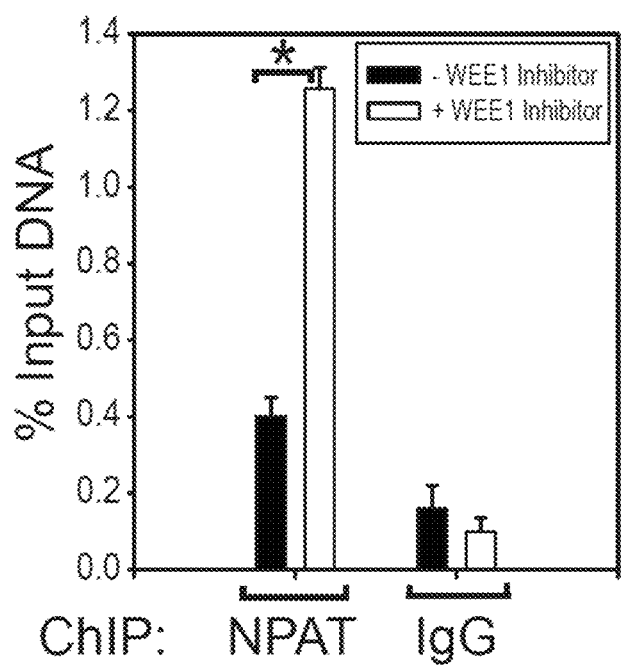
FIG. 3G to 3H are graphs showing ChIP (% input DNA) in synchronized MEFs treated with WEE1 inhibitor or untreated and harvested 6.30 hours post-release. ChIP was performed using NPAT and IgG antibodies (FIG. 3G) or RNA Pol II and IgG (FIG. 3H) followed by qPCR using primers corresponding to Site II. *p=0.0018, **p=0.01.
Figure 3H:
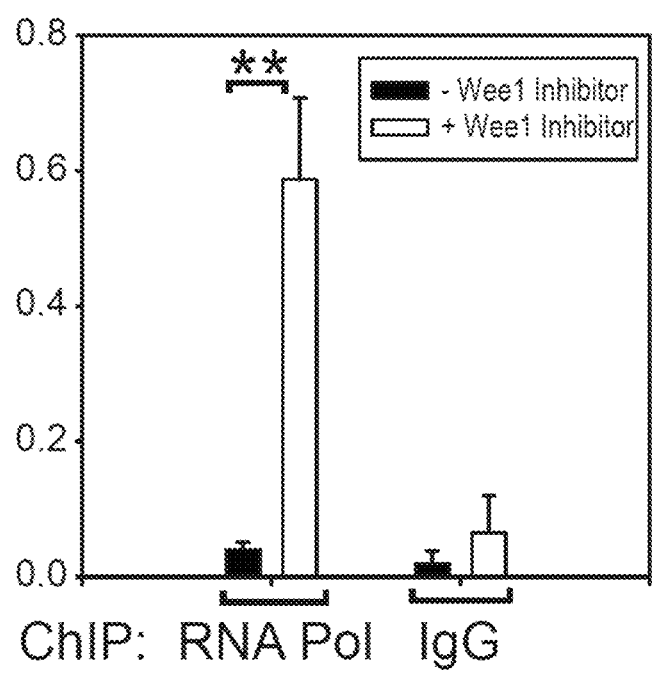
Figure 3I:
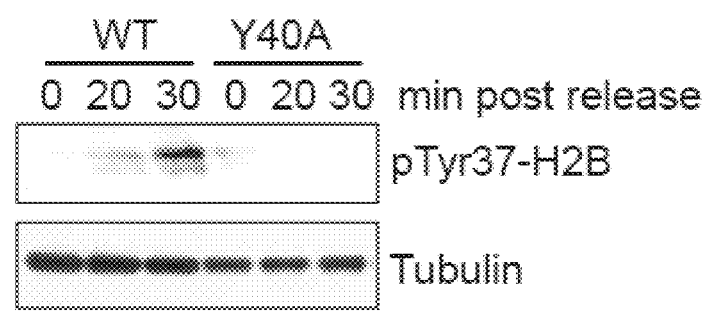
FIG. 3I is an immunoblot showing total histones prepared from synchronized WT (first three columns) and Y40A mutant yeast cells (last three columns) 0, 20, and 30 minutes post release that were immunoprecipitated with pTyr37-H2B antibodies and immunoblotted with yeast H2B antibodies (upper panel) or yeast tubulin antibodies (bottom panel).
Figure 3J:
FIG. 3J is an immunoblot showing total histones prepared from WT and swe1Δ mutant yeast cells subjected to SDS-PAGE followed by immunoblotting with pTyr37-H2B (top panel) and H2B (bottom panel) antibodies.
Figure 3K:
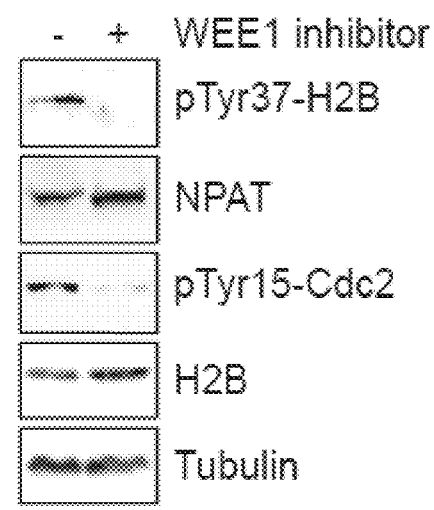
FIG. 3K is an immunoblot showing synchronized MEFs untreated (left column) or treated with WEE1 inhibitor (right column) that were harvested 6.30 hours post-release and immunoblotted with antibodies to pTyr37-H2B (first row), NPAT (second row), pTyr15-Cdc2 (third row), H2B (fourth row), or Tubulin (bottom row).

To validate the role of H2B Tyr37-phosphorylation in histone transcriptional suppression, budding yeast S. cerevisiae was utilized. Tyr37 is evolutionarily conserved from humans to unicellular eukaryotes e.g. Tyr40 in S. cerevisiae (FIG. 3A). In S. cerevisiae, histones are transcribed from four sets of gene pairs, HTA1-HTB1 and HTA2-HTB2 for H2A and H2B, and HHT1-HHF1 and HHT2-HHF2 for H3 and H4 (Hereford, L. et al. (1982) Cell, 30:305-310; Hereford, L. M. et al. (1981) Cell, 24:367-375; Osley, M. A. et al. (1982) Proc. Nat. Acad. Sci. U.S.A., 79:7689-7693). Similar to metazoan, the transcription is activated at the G1/S transition and repressed in G1 and G2/M phases of the cell cycle (Osley, M. A. et al. (1982) Proc. Nat. Acad. Sci. U.S.A., 79:7689-7693; Osley, M. A. et al. (1987) Mol. Cell. Biol., 7:4204-4210; Sutton, A. et al. (2001) Genetics, 158: 587-596; Cross, S. L. et al. (1988) Mol. and Cell. Biol., 8:945-954). To assess whether H2B Tyr40-phosphorylation regulates histone gene transcription, WT and H2B-Y40A mutant cells (Nakanishi, S. et al. (2008) Nature Struct. & Mol. Biol., 15:881-888) of S. cerevisiae were synchronized by adding a-factor, resuspended in fresh media and harvested at different time-points. H2B Tyr40-phosphorylation was observed 20-30 min post a-factor release, in contrast, H2B Tyr40-phosphorylation was abrogated in Y40A mutant yeast (FIG. 3I). To examine histone RNA levels, total RNA was isolated from WT and H2BY40A mutant yeast followed by qRT-PCR. The WT cells exhibited peak histone RNA synthesis at 20 minutes post a-factor release followed by rapid decrease (FIGS. 3B-3F, 3J). In contrast, HTA1, HTB1, HHF1 and HHT1 mRNA levels continue to increase peaking at 30 minutes in the Y40A mutant (FIGS. 3B-3F, 3J, compare 30 minutes). Overall mRNA levels of HHT2 did not increase significantly in Y40A mutant, however, they did peak at 30 minutes as seen in case of HTA1, HTB1, HHF1, and HHT1 (FIGS. 3E and 3F).

Figure 6A:
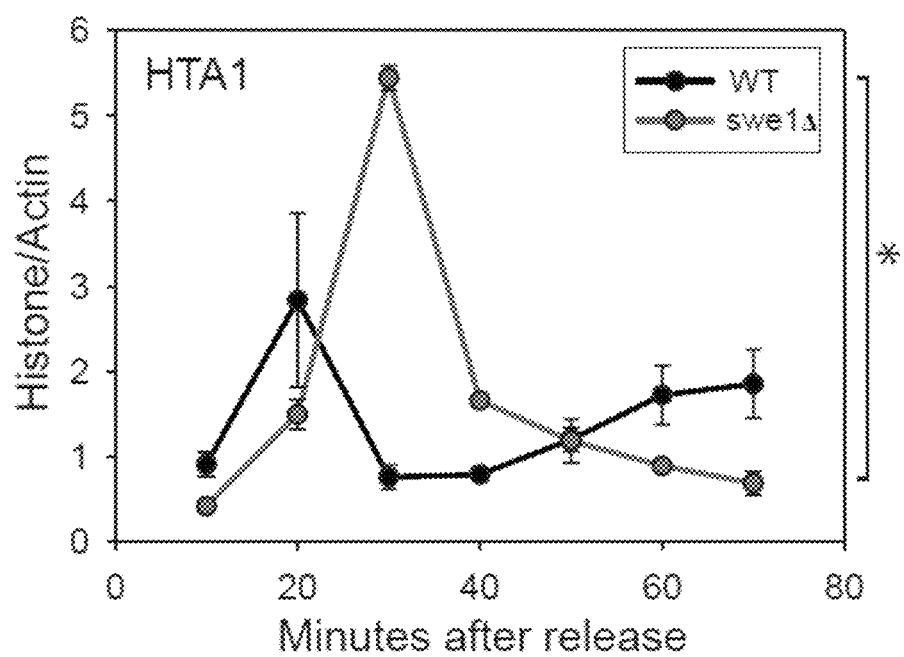
FIGS. 6A and 6B are line graphs showing yeast Swe1 mutant (swe1Δ) exhibits increased transcription of histones HTA1 (FIG. 6A) and HTB1 (FIG. 6B). The WT and swe1Δ mutant yeast cells were treated with α-factor for 3 hours, washed and cells were released in YPD media and harvested at indicated time points post-release. Total RNA was prepared followed by qRT-PCR for histones transcripts. Data are representative of three independent experiments. The p values are as follows: *p=0.00001; **p=0.037.
Figure 6B:
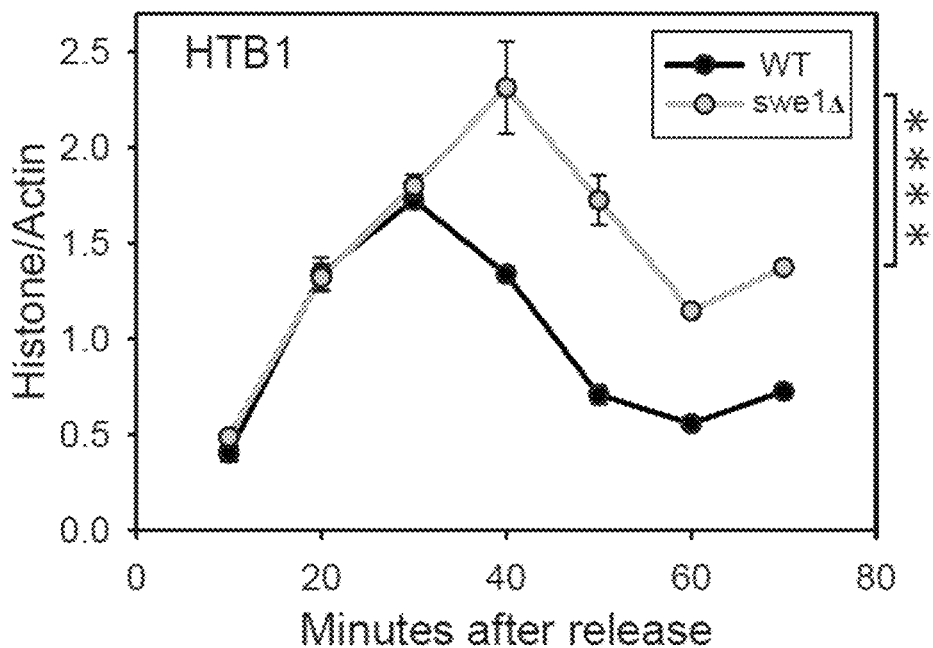

A homolog of WEE1 in *S. cerevisiae* is SWE1, which is the only tyrosine kinase in budding yeast (Booher, R. N. et al. (1993) Embo. J., 12:3417-3426). SWE1 mutant (swe1Δ) failed to phosphorylate H2B at Tyr40, indicating that SWE1 mediated Tyr37-phosphorylation of H2B is conserved in yeast. To determine whether loss of SWE1 kinase activity and thus loss of Tyr40 phosphorylation of H2B would also lead to loss of transcriptional suppression of yeast histones, total RNA isolated from WT and swe1Δ mutant were subjected to qRT-PCR. As seen in mammalian cells (in FIGS. 2B-2G), loss of SWE1 activity in yeast too resulted in significant increase in HTA1 and HTB1 levels (FIG. 6). Taken together, these data indicate that histone transcription suppression caused by SWE1 mediated by H2B Tyr40-phosphorylation is conserved in *S. cerevisiae*.

FACS analysis was performed to determine whether the increase in histone gene expression is due to an altered cell cycle profile of the Y40A mutant cells. Synchronized WT and Y40A mutant *S. cerevisiae* were released into YPD media, harvested at the indicated time intervals, stained with Sytox green followed by flow cytometry. WT and Y40A mutant cells exhibited similar cell cycle kinetics (FIGS. 7A and 7B), indicating that increased histone RNA levels observed in H2B Y40A mutant is not due to altered cell cycle profile.

Figure 7A:
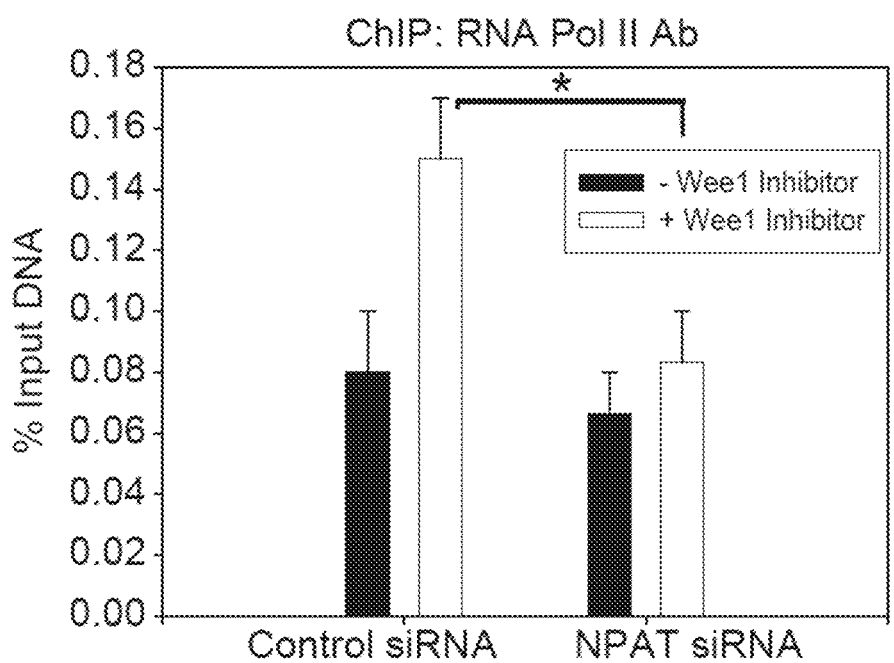
FIGS. 7A and 7B are bar graphs showing RNA Pol II is not present at site II in NPAT depleted cells. a and b. The synchronized MEFs were a. treated with WEE1 inhibitor or untreated, b. transfected with control or NPAT siRNAs, were harvested 6.30 hours post-release. ChIP was performed using RNA Pol II (FIG. 7A) or NPAT (FIG. 7B) followed by qPCR using primers corresponding to Site II. *p=0.052, **p=0.04.
Figure 7B:
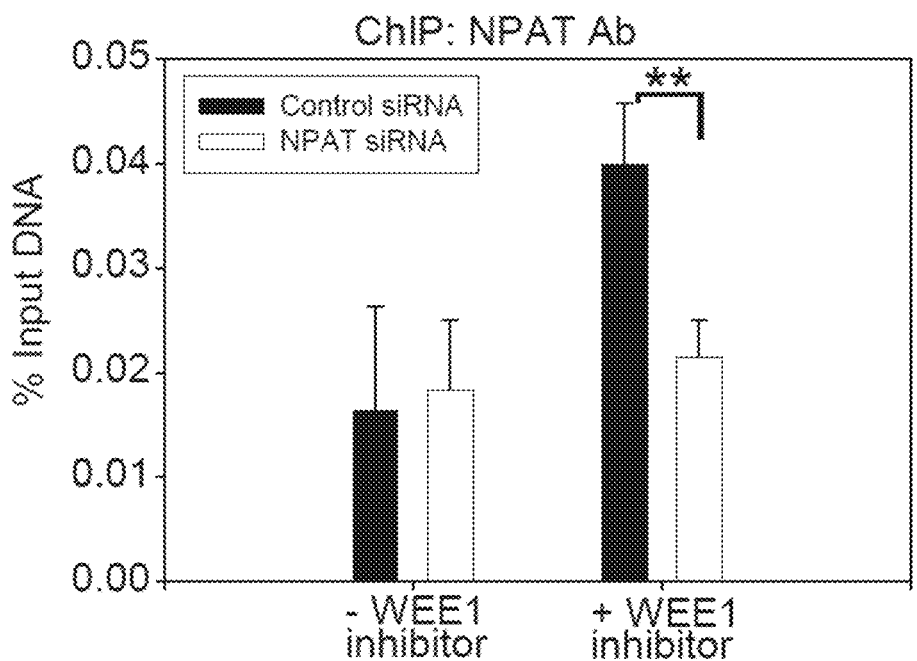

To understand the potential mechanism of repression of histone transcription the role of NPAT was assessed. NPAT has been shown to play an essential role in the transcriptional activation of histone genes by its recruitment along with RNA polymerase II at both Hist1 clusters (Miele, A. et al. (2005) Mol. and Cell. Biol., 25:6140-6153; Wei, Y. et al. (2003) Mol. and Cell. Biol., 23:3669-3680; Zhao, J. et al. (1998) Genes & Development, 12:456-461; Zhao, J. et al. (2000) Genes & Development, 14:2283-2297). Chromatin from synchronized MEFs at 6.30 hours post-release was immunoprecipitated with NPAT or RNA polymerase II antibodies, respectively, followed by qPCR. While recruitment of NPAT and RNA polymerase II was not observed when H2B Tyr37-phosphorylation was optimal, binding was detected when the phosphorylation was abrogated by treatment with WEE1 inhibitor (FIGS. 3G-3H). To confirm that RNA polymerase II presence at site II is dependent on NPAT, MEFs were transfected with control and NPAT siRNAs and chromatin was immunoprecipitated with RNA polymerase II antibodies followed by qPCR. RNA polymerase II presence at site II was significantly decreased upon depletion of NPAT (FIGS. 7A and 7B).

Figure 3L:
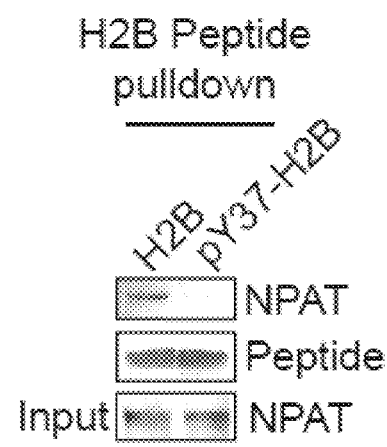
FIG. 3L is an immunoblot showing immobilized unmodified and Tyr37-phosphorylated H2B (25-49) peptides that were incubated with HEK293 cell lysates followed by immunoblotting with NPAT antibody (top panel) or staining with coommassie blue (middle panel).
Figure 20:
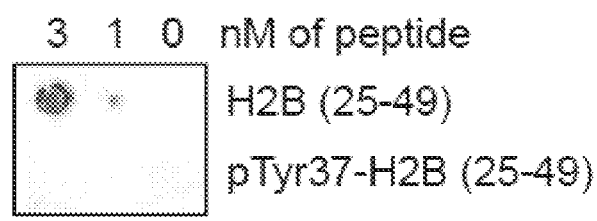
FIG. 20 is an immunoblot of 3 nM (column 1), 1 nM (column 2), or 0 nM (column 3) H2B(25-49) peptides (top row) or pY37-H2B(25-49) peptides (bottom row) spotted on nitrocellulose membrane, dried, blocked with BSA, and incubated overnight at 4° C. with HEK293 cell lysates, washed, and immunoblotted with NPAT antibodies.

To understand the mechanism underlying loss of NPAT binding to site II when H2B is Tyr37-phosphorylated, pull-down assay were performed with biotin-conjugated H2B peptides spanning amino acids 25-49. The unphosphorylated or H2B(25-49) and pY37-H2B(25-49) peptides were immobilized on streptavidin-Sepharose beads followed by incubation with HEK293 whole cell extract. Beads were washed and bound protein was analyzed by immunoblotting with NPAT antibodies. While NPAT specifically bound to unmodified H2B peptide, the binding was abolished when the peptide was phosphorylated at Tyr37 (FIG. 3L). The specificity of NPAT for unphosphorylated H2B was further confirmed by filter binding assay (FIG. 20). Taken together, these data indicate that H2B Tyr37-phosphorylation excluded the ability of NPAT to bind upstream of Hist1 cluster.

Collectively, these data unveil previously unknown mechanism wherein marking chromatin specifically upstream of major histone gene cluster Hist1 with H2B Tyr37-phosphorylation suppressed transcription of histone genes. This mechanism appears to be conserved, including in yeast where H2B-Tyr40-phosphorylation suppressed histone transcription. Further, it uncovers a new function of SWE1/WEE1, i.e. maintaining histone mRNA levels. Overall, whether in mammals or yeast, H2B-Tyr37-phosphorylation appears to be vital to cellular homeostasis as in combination with histone mRNA turnover, histone transcription repression could efficiently and rapidly lower the transcript levels, eliminating overload of core histones after DNA synthesis.

Example 2

Phosphorylation of Histone H3 at Tyrosine 99: Implications in Prostate Cancer

Despite androgen deprivation, prostate cancer progresses to castration resistant prostate cancer (CRPC) stage which no longer responds to androgen ablation therapy. The epigenetic modifications underlying CRPC growth are not clear. The non-receptor tyrosine kinase, Ack1, phosphorylates androgen receptor (AR) at Tyr267 and Tyr-363. ChIP-qPCR analysis revealed specific recruitment of pTyr284-Ack1/pTyr267-AR or pTyr363-AR to PSA, NKX3,1 and TMPRSS2 gene promoters in the absence of androgen, leading to growth of CRPC tumors. However, precise mechanistic details of transcriptional regulation are not clear.

The discovery was made that Ack1 phosphorylates histone H3 at tyrosine 99. To delineate functional consequences of H3 Ty99-phosphorylation, phospho-antibodies were raised. Treatment of cell lines with variety of ligands resulted in activation of cognate RTKs which in turn activated Ack1. Ack1 phosphorylated H3 at Tyr99, which was significantly compromised upon Ack1-specific small molecule inhibitor, AIM-100 treatment. Notably, AIM-100 suppressed recruitment of pTyr-AR to PSA, NKX3,1 and TMPRSS2 promoters and mitigated the growth of CRPC xenograft tumors. Further, AIM-100 treatment increased H3K9 and K27 dimethylation and trimethylation. H3 Y99F mutant also exhibited increased H3K27 dimethylation and trimethylation. Thus, marking of chromatin with H3-Tyr99-phosphorylation within AR-target gene promoters may suppress repressive dimethylation leading to transcriptional activation in androgen-deprived environment of CRPC tumors. This study uncovers a previously unknown mechanism of regulation of pTyr267-AR-target gene expression, which can be therapeutically reversed by suppression of Ack1/AR/pTyr99-H3 signaling by AIM-100.

Results

Figure 21:
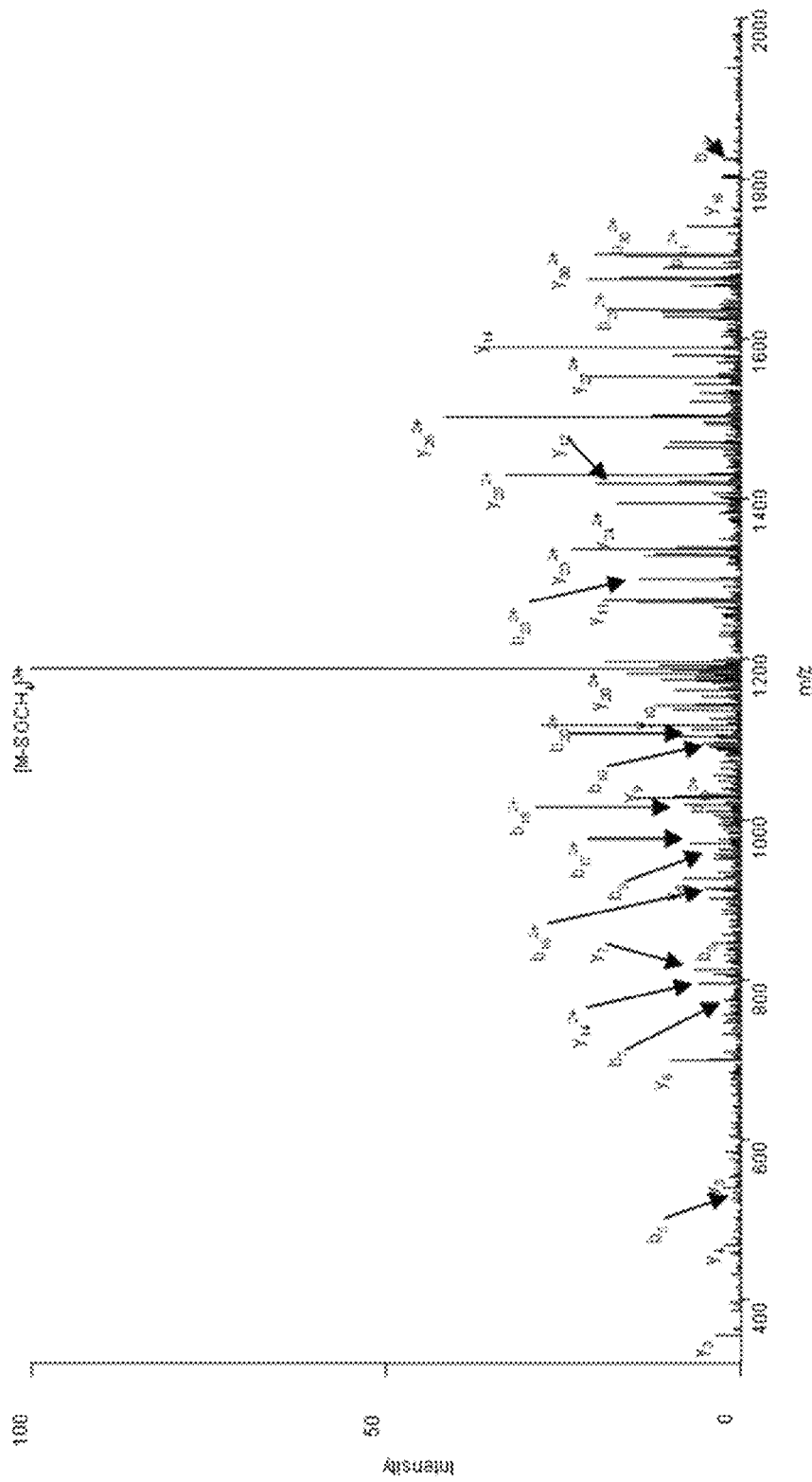
FIG. 21 is a histogram identifying the histone H3 Tyr99-phosphorylation site. The peptide was detected at 32.7 minutes in the total ion chromatogram with mass-to-charge ratio 1208.8928. The tandem mass spectrum matched the following sequence, FQSSAVMALQEACEAYL-VGLFEDTNLCAIHAK (SEQ ID NO:55) indicating that the tyrosine was phosphorylated; the detection of the y16 and y17 is consistent with this localization. The assignment was made with Mascot with a score of 92.
Figure 22:
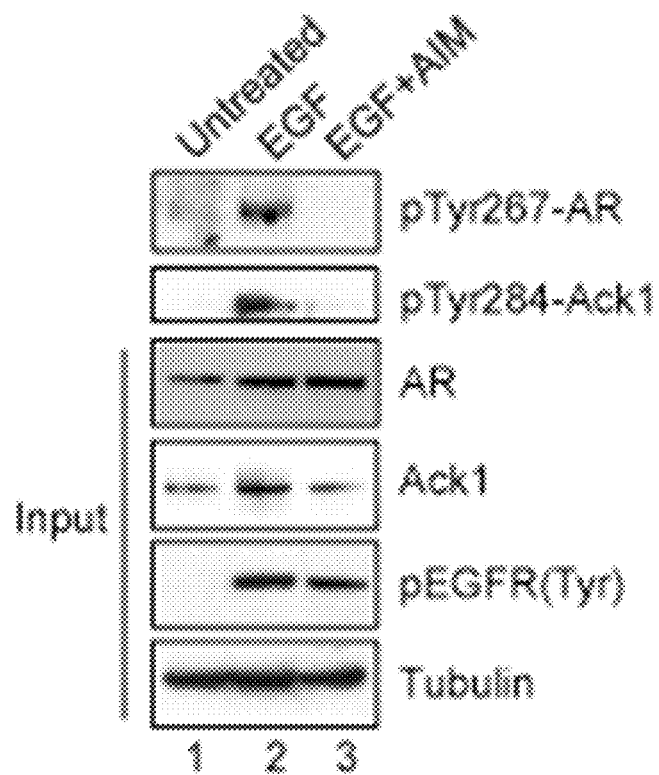
FIG. 22 is an immunoblot of lysates from LAPC4 cells that were untreated (column 1), treated with EGF (column 2), or treated with EGF and AIM-100 (0.8 uM, 16 hr) (column 3) that were immunoblotted with androgen receptor (AR) (row 3), Ack1 (row 4), pEGFR(Tyr) (row 5), Tubulin (row 6), pTyr267-AR (top row), or pTyr284-Ack1 (row 2) antibodies.

Tyrosine 99 is phosphorylated in Histone H3 (FIG. 21). The peptide was detected at 32.7 minutes in a total ion chromatogram with mass-to-charge ratio of 1208.8928. The tandem mass spectrum matched the following sequence, FQSSAVMALQEACEAYLVGLFEDTNLCAIHAK (SEQ ID NO:55) indicating that the tyrosine was phosphorylated; the detection of the y16 and y17 is consistent with this localization. The assignment was made with Mascot with a score of 92.

Figure 25:
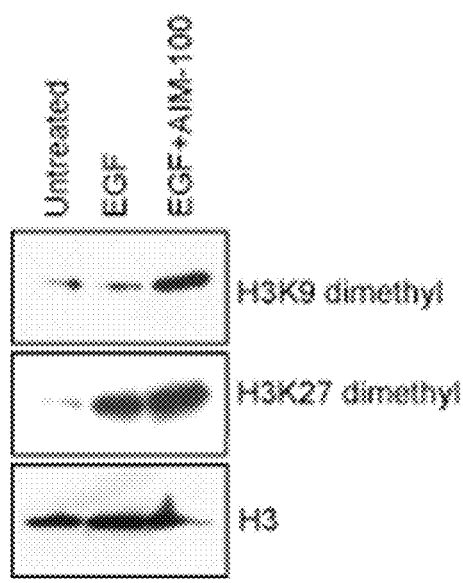
FIG. 25 is an immunoblot of lysates from LAPC4 cells that were untreated (column 1), treated with EGF (column 2), or treated with EGF and AIM-100 (column 3) that were immunoblotted with H3K9 dimethyl (top panel), H3K27 (middle panel), or H3 (bottom panel) antibodies.

LAPC4 cells were treated with EGF or EGF and AIM-100 and the lysates were immunoblotted with H3K9 dimethyl and H3K27 dimethyl antibodies. Thus, marking of chromatin with H3-Tyr99-phosphorylation within AR-target gene promoters may suppress repressive dimethylation leading to transcriptional activation in androgen-deprived environment of prostate tumors. Ack1 inhibition by AIM-100 treatment increased H3K9 and K27 dimethylation (FIG. 25).

Figure 8A:
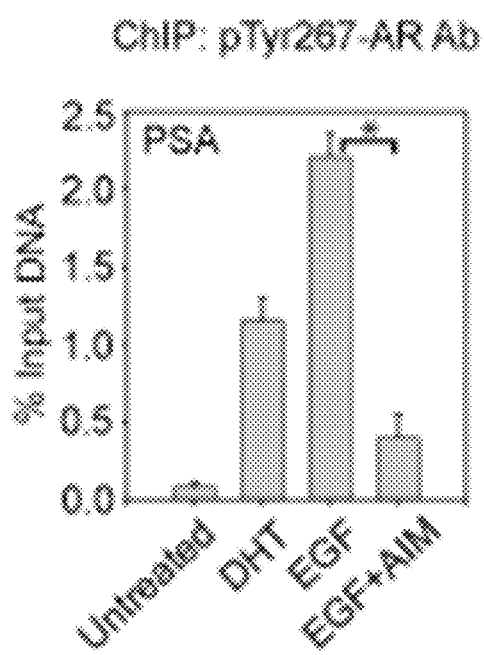
FIG. 8A-8C are bar graphs showing Ack1 inhibition by AIM-100 suppressed recruitment of pTyr-AR to PSA (FIG. 8A), NKX3.1 (FIG. 8B) and TMPRSS2 (FIG. 8C) promoters. LAPC4 cells were treated with DHT (5 nM, 16 hr) or EGF (10 ng/ml, 1 hr), and AIM-100 (0.8 µM, 16 hr) and ChIP analysis for pTyr267-AR binding to the PSA, NKX3.1 and TMPRSS2 AREs was performed followed by qPCR. *p=0.001; p=0.006; *p=0.014.
Figure 8B:
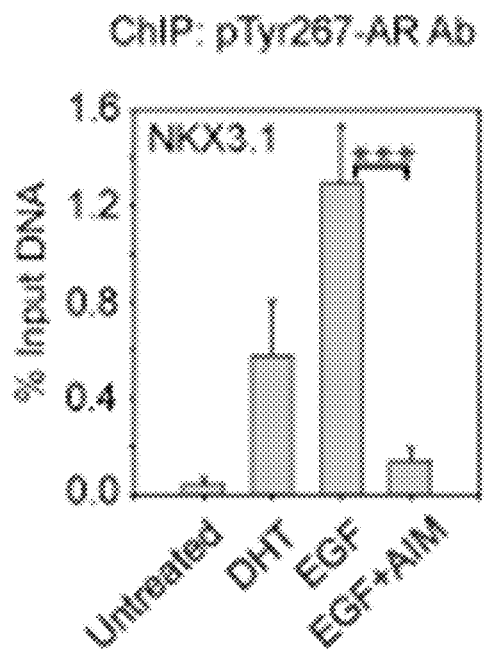
Figure 8C:
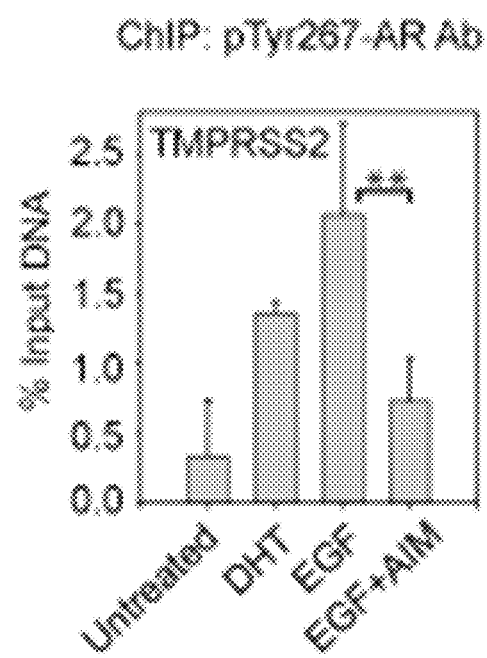

LAPC4 cells were treated with DHT (5 nM, 16 hr), EGF (10 ng/ml, 1 hr), or EGF and AIM-100 (0.8 µM, 16 hr) and ChIP analysis for pTyr267-AR binding to the PSA, NKX3.1 and TMPRSS2 AREs was performed followed by qPCR. Ack1 inhibition by AIM-100 suppressed recruitment of pTyr-AR to PSA, NKX3,1 and TMPRSS2 promoters (FIGS. 8A-8C).

Figure 23:
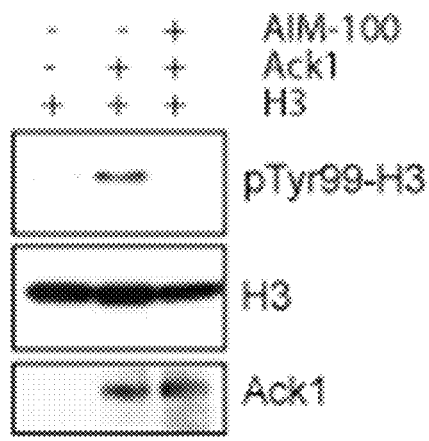
FIG. 23 is an immunoblot of purified histone H3 (all columns) and Ack1 (columns 2 and 3) incubated at 37° C. for 1 hour with AIM-100 (column 3) or without AIM-100 (columns 1 and 2) that were immunoblotted with pTyr99-H3 (top row), H3 (middle row) or Ack1 (bottom row) antibodies.

Purified histone H3 and Ack1 were incubated at 37° C. for 1 hour with or without AIM-100 followed by immunoblotting with indicated antibodies. Ack1 directly phosphorylates histone H3 at Tyr99 (FIG. 23).

Figure 24:
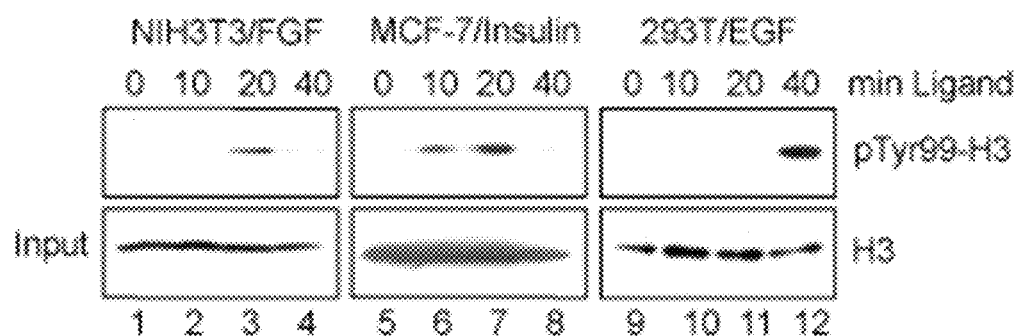
FIG. 24 is an immunoblot of cell lysates from NIH3T3 cells (columns 1-4) treated with FGF for 0 minutes (column 1), 10 minutes (column 2), 20 minutes (column 3), or 40 minutes (column 4), MCF-7 cells (columns 5-8) treated with insulin for 0 minutes (column 5), 10 minutes (column 6), 20 minutes (column 7), or 40 minutes (column 8), or 293T cells (columns 9-12) treated with EGF for 0 minutes (column 9), 10 minutes (column 10), 20 minutes (column 11), or 40 minutes (column 12) that were immunoprecipitated with pTyr99-H3 antibodies and immunoblotted with H3 pan-antibodies (top panel) or immunoblotted with H3 pan-antibodies without immunoprecipitation (bottom panel).

Ack1 phosphorylated H3 at Tyr99. The cell lines NIH3T3, MCF-7, 293T were treated with ligands (FGF, insulin, or EGF, respectively) and cell lysates were immunoprecipitated with pTyr99-H3 antibodies followed by immunoblotting with H3 pan-antibodies. Treatment of cancer derived cell lines with variety of ligands resulted in activation of cognate receptor tyrosine kinases which in turn activated Ack1 (FIG. 24).

LAPC4 cells were treated with EGF or EGF and AIM-100 and the lysates were immunoblotted with H3K9 and H3K27 antibodies. Thus, marking of chromatin with H3-Tyr99-phosphorylation within AR-target gene promoters may suppress repressive dimethylation leading to transcriptional activation in androgen-deprived environment of prostate tumors. Ack1 inhibition by AIM-100 treatment increased H3K9 and K27 dimethylation (FIG. 25).

293T cells were transfected with FLAG-tagged H3 or Y99F mutant. Lysates were immunoprecipitated with FLAG antibodies followed by immunoblotting with H3K27 pan-antibodies. H3 Y99F mutant exhibited increased H3K27 dimethylation (FIG. 12).

Figure 9:
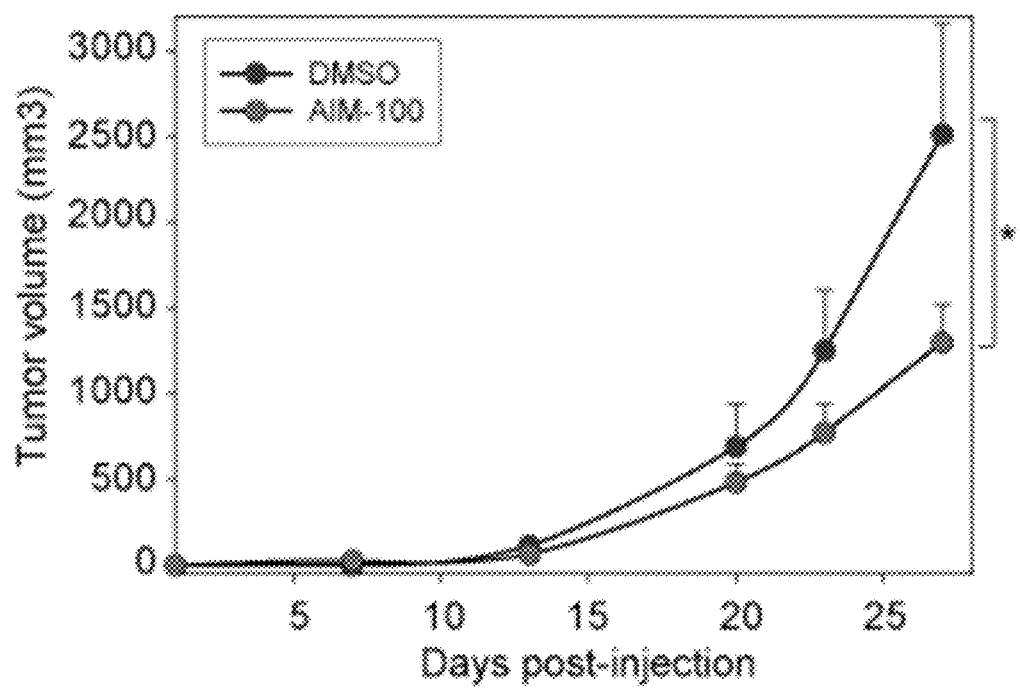
FIG. 9 is a line graph showing prostate xenograft tumor volume ($mm^3$) in castrated nude male mice treated with AIM-100 Ack1 inhibitor or DMSO control. Castrated nude male mice were injected with LNCaP-caAck expressing cells. Mice were injected with AIM-100 (4 mg/kg of body weight per injection) on five times (n=8) and tumor volumes were measured.

Castrated nude male mice were injected with LNCaP-caAck expressing cells. Mice were injected with AIM-100 (4 mg/kg of body weight per injection) on five times (n=8) and tumor volumes were measured. Ack1 inhibition by AIM-100 partially suppresses prostate xenograft tumor growth (FIG. 9).

Inhibition of Ack1 abrogates H3Y99 phosphorylation and increases dimethylation of Histone H3 at lysine 9 and 27, two epigenetic modifications that are linked to gene silencing. Ack1/pTyr-AR complex is likely to regulate gene expression by multiple epigenetic changes, e.g., H3 phosphorylation at Y99 and dimethylation and trimethylation at K9 and K27 at specific promoters that confer survival and castration resistance in prostate cancer. Ack1 phosphorylates histone H3 at Y99 in response to various growth factor stimulations.

Example 3

Histone H4 Tyrosine 51-Phosphorylation Regulates Embryo Development

Gastrulation involves of a series of coordinated cell movements to organize the germ layers and establish the major body axes of the embryo. One of the gastrulation movements which involves the thinning and spreading of a multilayered cell sheet is called epiboly. Epiboly plays a crucial role in all vertebrate gastrulation. Significant studies relevant to epiboly have been performed which revealed basic cellular properties and mechanisms of morphogenesis that are widely used in vertebrate development. Although significant progress has been made to understand cellular changes leading to epiboly, the epigenetic changes that are involved in driving this process are not clear.

The following example demonstrates that histone H4 phosphorylation at tyrosine 51 (Tyr51) is critical for epiboly. RNA isolation followed by Microarray analysis revealed that H4 Tyr51 phosphorylation regulates multiple genes involved in development. Ack1, a non-receptor tyrosine kinase, was identified to be the kinase that phosphorylates H4 at Tyr51. Knockdown or inhibition of Ack1 resulted in significant decrease in H4 Tyr51 phosphorylation. *Xenopus* embryos injected with antibodies raised against Tyr51-phosphorylated H4 or Ack1 inhibitor, AIM-100 exhibited epiboly block or involution failure in 51% of surviving embryos and a partial "reduced epiboly" phenotype appearing in an additional 14%. All the affected embryos were unable to close the blastopore, and the embryo did not progress further in gastrulation due to the developmental arrest. Taken together, these data unveil a previously unknown mechanism wherein marking chromatin with H4-Tyr51-phosphorylation is required for transcription of developmentally regulated genes that are critical for gastrulation.

Results

Figure 10A:
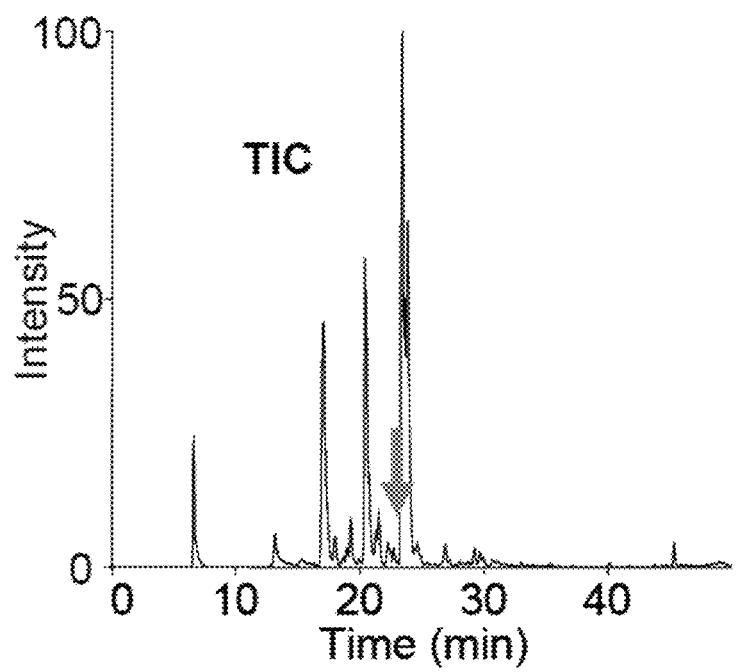
FIG. 10A-10C are histograms identifying the histone H4 Tyr51-phosphorylation site. The peptide was detected at 22.9 minutes in the total ion chromatogram (FIG. 10A) with mass-to-charge ratio 630.7919 (FIG. 10B). The tandem mass spectrum matched the following sequence, ISGLIYEETR (SEQ ID NO:56) indicating that the tyrosine was phosphorylated; the detection of the b5 and b6 is consistent with this localization (FIG. 10C). The assignment was made with Sequest with XCorr 3.26 and ΔCN: 0.31.
Figure 10B:
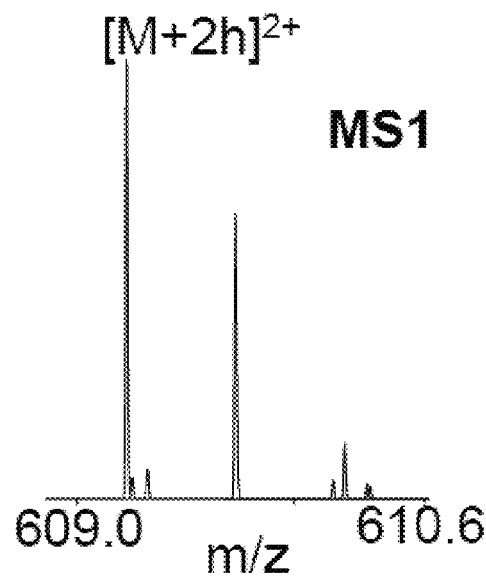
Figure 10C:
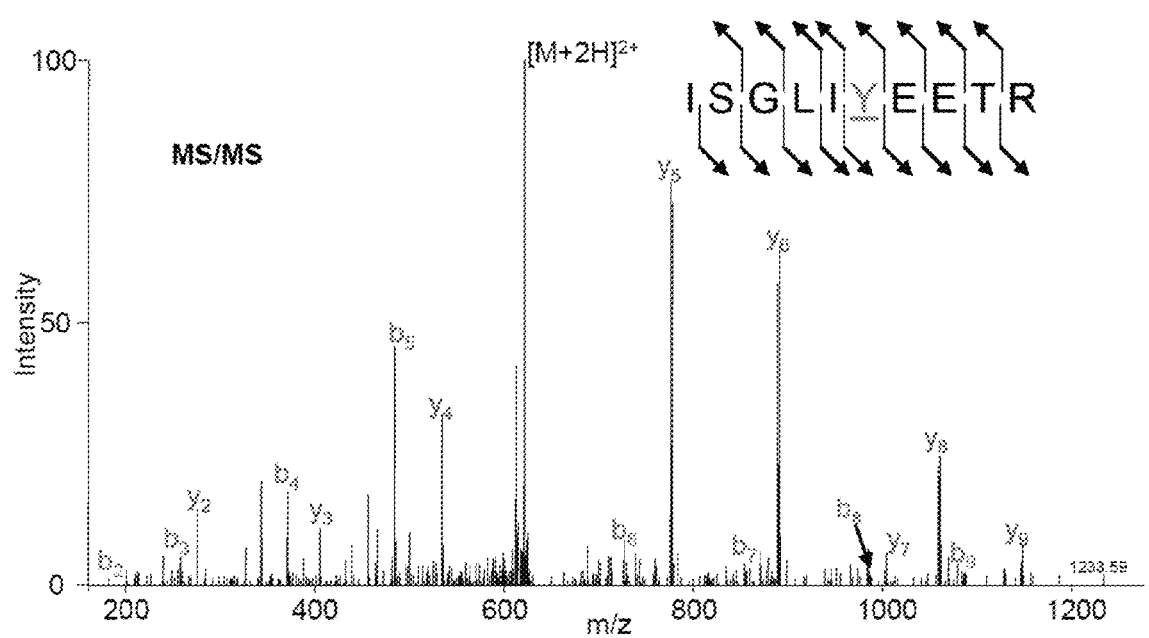

The histone octamers are wrapped around with 147 base pairs of DNA to form a nucleosome, which is subjected to at least eight distinct types of post-translational modifications including phosphorylation (Kouzarides, T. (2007) Cell, 128:693-705). A variety of histone modifications constitute a 'histone code' that can be recognized by different chromatin regulatory proteins, which in turn affect the chromatin structure and regulate the gene expression. The histone modifications are carefully regulated and can have major consequences when altered (Berger, S. L. (2007) Nature, 447:407-412). To understand functional consequences of histone tyrosine phosphorylation, histones were purified from human cell line HEK293 cells and histones were subjected to mass spectrometry based phosphorylation identification. A novel phosphorylation at tyrosine 51 in histone H4 was identified (FIG. 10). Tyr51 is evolutionarily conserved from humans to unicellular eukaryotes e.g. in *S. cerevisiae* (FIG. 11). Since the functional role of Tyr51-phosphorylated H4 (pTyr51-H4) is unknown, phosphospecific antibodies were raised against pTyr51-H4 (Methods section). pTyr51-H4 antibodies were validated in multiple cell lines.

Figure 27A:
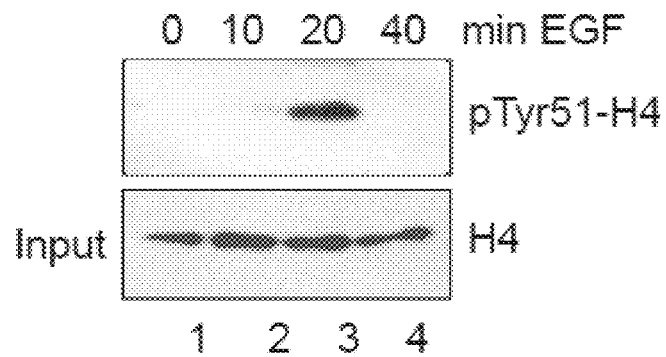
FIGS. 27A and 27B are immunoblots of cell lysates from serum starved HEK293T (FIG. 27A) and LNCaP (FIG. 27B) cells treated with EGF ligand for 0 minutes (column 1), 10 minutes (column 2), 20 minutes (column 3), or 40 minutes (column 4) that were either immunoprecipitated with pTyr51-H4 antibodies and immunoblotted with H4 antibody (top panel) or immunoblotted with H4 antibody without immunoprecipitation (bottom panel).
Figure 27B:
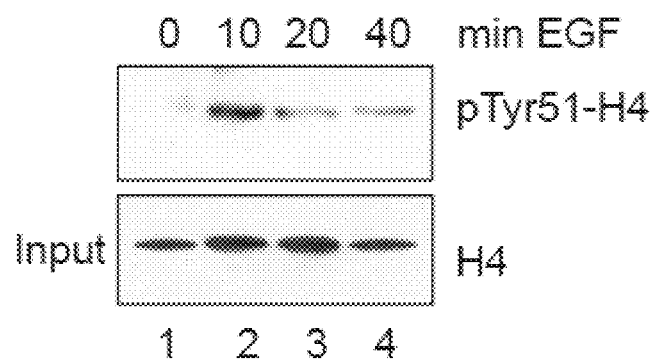
Figure 27C:
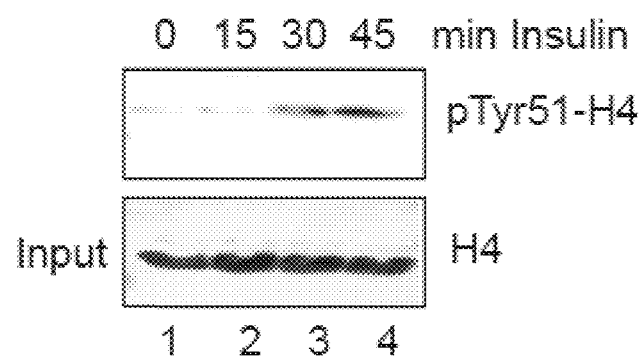
FIG. 27C is an immunoblots of cell lysates from serum starved MCF-7 cells treated with insulin ligand for 0 minutes (column 1), 15 minutes (column 2), 30 minutes (column 3), or 45 minutes (column 4) that were either immunoprecipitated with pTyr51-H4 antibodies and immunoblotted with H4 antibody (top panel) or immunoblotted with H4 antibody without immunoprecipitation (bottom panel).
Figure 27D:
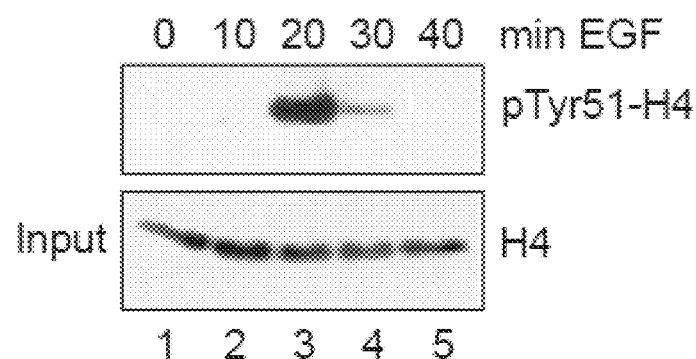
FIG. 27D is an immunoblot of cell lysates from HEK293T cells transfected with FLAG-tagged H4 and treated with EGF ligand for 0 minutes (column 1), 10 minutes (column 2), 20 minutes (column 3), 30 minutes (column 4), or 40 minutes (column 5) that were either immunoprecipitated with pTyr51-H4 antibodies and immunoblotted with FLAG antibody (top panel) or immunoblotted with FLAG antibody without immunoprecipitation (bottom panel).
Figure 27E:
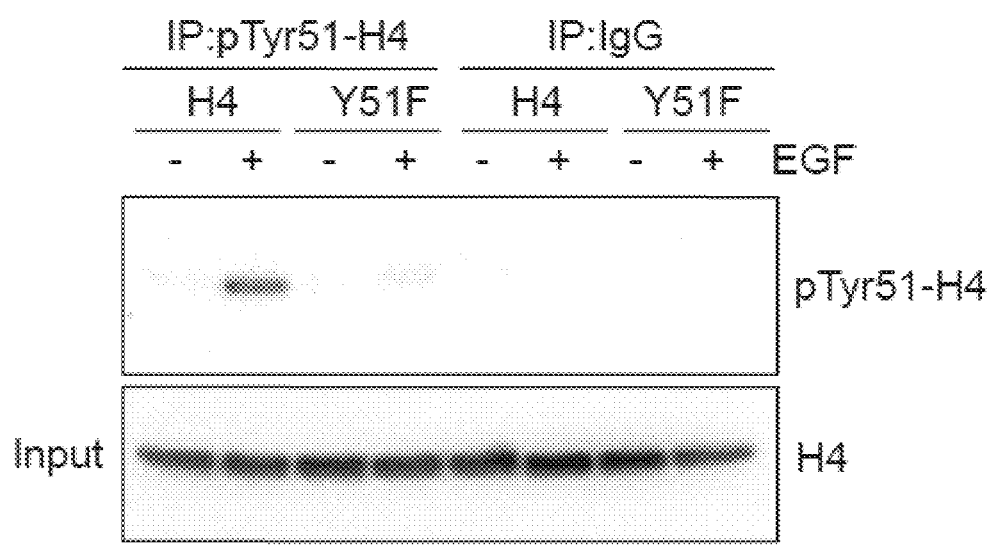
FIG. 27E is an immunoblot of cell lysates from HEK293T cells transfected with FLAG-tagged H4 (columns 1, 2, 5, and 6) or Y51F mutant (columns 3, 4, 7, and 8) and treated with EGF (columns 2, 4, 6, and 8) that were either immunoprecipitated with pTyr51-H4 antibodies and immunoblotted with FLAG antibody (top panel) or immunoblotted with FLAG antibody without immunoprecipitation (bottom panel).

Various human cell lines e.g. HEK293, LNCaP and MCF-7 cells were treated with EGF and insulin ligands and cell lysates were immunoprecipitated with pTyr51-H4 antibodies followed by immunoblotting with H4 antibodies. Specifically, serum starved HEK293T, LNCaP, and MCF-7 cells were treated with EGF or insulin ligand for indicated time and cells were harvested. Equal amounts of cell lysates were immunoprecipitated with pTyr51-H4 antibodies followed by immunoblotting with H4 antibody. Equal amounts of lysates were immunoblotted with H4 antibody. Tyr51-phosphorylated H4 was specifically identified upon 10 and 20 min of EGF treatment in LNCaP and HEK 293 cells, respectively (FIGS. 27A and 27B, top panels). Further, 30-45 min of insulin treatment of MCF-7 cells resulted in Tyr51-phosphorylation of H4 (FIG. 27C, top panel).

pTyr51-H4 antibodies were further validated by transfecting HEK293 cells with FLAG-tagged H4. Cells were treated with EGF ligand and cell lysates were immunoprecipitated with pTyr51-H4 antibodies followed by immunoblotting with FLAG antibodies. Specifically, HEK293T cells were transfected with FLAG-tagged H4, 48 hours later lysates were immunoprecipitated with pTyr51-H4 antibodies followed by immunoblotting with FLAG antibody. Tyr51-phosphorylated H4 was specifically identified upon 20 min of EGF treatment (FIG. 27D, top panel). Moreover, pTyr51-H4 antibodies were screened for its cross-reactivity against unphosphorylated H4 by transfecting HEK293 cells with FLAG-tagged H4 or Tyr51 to Phe (Y51F) point mutant of H4. Specifically, HEK293T cells were transfected with FLAG-tagged H4 or Y51F mutant. 48 hours later, cells were treated with EGF (or untreated) and lysates were immunoprecipitated with pTyr51-H4 antibodies followed by immunoblotting with FLAG antibody. EGF treatment and immunoprecipitation with pTyr51-H4 antibodies followed by immunoblotting with FLAG antibodies revealed H4 Tyr51-phosphorylation only in H4 transfected samples but not Y51F mutant H4 transfected samples. As a control immunoprecipitation with IgG was performed. Collectively, these data indicate that the antibodies are selective for pTyr51-phosphorylation on histone H4.

Figure 26A:
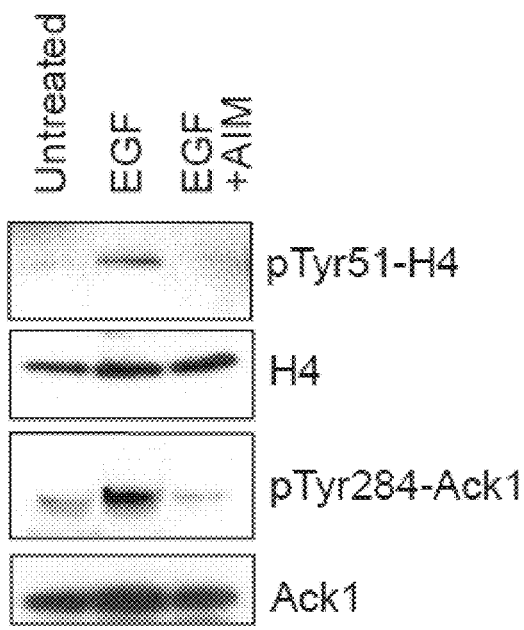
FIG. 26A is an immunoblot of cell lysates from serum starved HEK293T cells treated with EGF (column 2), EGF+AIM-100 (column 3), or untreated (column 1) that were either immunoprecipitated with pTyr51-H4 antibodies and immunoblotted with H4 antibody (top panel), immunoblotted with H4 antibody (2nd panel), immunoblotted with pTyr284-Ack1 antibody (3r Panel), or immunoblotted with Ack1 antibody (4th panel).

Ack1, a nonreceptor tyrosine kinase has emerged as a critical early transducer of variety of extracellular growth factor stimuli including heregulin, insulin, EGF and PDGF signaling (Manser, E. et al. (1993) Nature, 363:364-367; Mahajan, N. P. et al. (2005) Cancer Res., 65:10514-10523; Mahajan, N. P. et al. (2007) Proc. Natl. Acad. Sci. U.S.A., 104:8438-8443; Yokoyama, N. et al. (2003) J. Biol. Chem., 278:47713-47723; Galisteo, M. L. et al. (2006) Proc. Natl. Acad. Sci. U.S.A., 103:9796-9801). Ack1 is ubiquitously expressed and primarily phosphorylated at Tyr284 leading to its kinase activation (Mahajan, N. P. et al. (2005) Cancer Res., 65:10514-10523; Yokoyama, N. et al. (2003) J. Biol. Chem., 278:47713-47723). Applicants' earlier studies demonstrated that Ack1 interacts with nuclear hormone receptor, androgen receptor (AR), translocates to nucleus and interacts with chromatin regulating PSA and hK2 gene expression (Mahajan, N. P. et al. (2005) Cancer Res., 65:10514-10523; Mahajan, N. P. et al. (2007) Proc. Natl. Acad. Sci. U.S.A., 104:8438-8443; Mahajan, K. et al. (2010) Prostate, 70(12):1274-1285). Ack1 gene is also shown to be amplified in primary lung, ovarian and prostate tumors which correlated with poor prognosis (van der Horst, E. H. et al. (2005) Proc. Natl. Acad. Sci. U.S.A., 102:15901-15906). Further, a novel mechanism of Ack1 mediated AKT activation has been identified wherein phosphorylation of Tyrosine 176 in the AKT kinase domain resulted in its translocation to the plasma membrane and subsequent kinase activation. To examine whether H4 is a Ack1 kinase substrate, cells were treated with EGF or EGF+Ack1 inhibitor, AIM-100 (Mahajan, K. et al. (2010) Prostate, 70:1274-1285). Specifically, serum starved HEK293T were treated with EGF or EGF+AIM-100 and cells were harvested. Equal amounts of cell lysates were immunoprecipitated with pTyr51-H4 antibodies followed by immunoblotting with H4 antibody (top panel). Equal amounts of lysates were immunoblotted with H4 antibody or pTyr284-Ack1 antibody. Ack1 inhibitor treatment resulted in almost complete loss of H4 pTyr51-phosphorylation (FIG. 26A). A somatic autoactivating mutation in Ack1, E346K, has been identified (Mahajan, K. et al. (2010) PLoS One, 5:e9646). E346K mutation cause constitutive activation of Ack1 kinase activity. Using site-directed mutagenesis, HA-tagged E346K point mutant was generated and purified. As a control, HA-tagged Ack1 K154L mutation was generated, which has lost kinase activity.

Figure 26B:
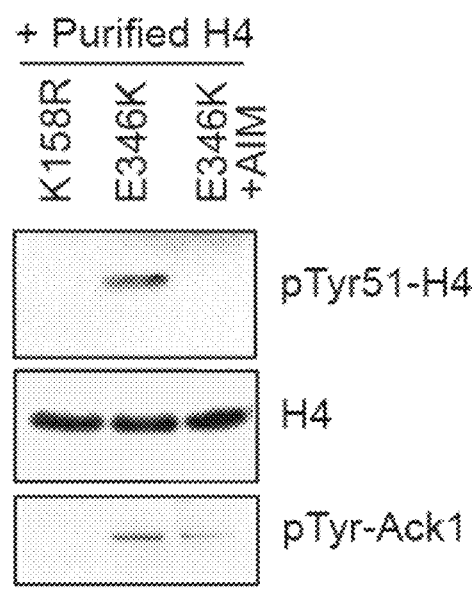
FIG. 26B is an immunoblot of equimolar amounts of purified constitutively active E346K-Ack1 (column 2) or kinase dead K158R-Ack1 (column 1) and H4 proteins were incubated in the presence (column 3) or absence (columns 1 and 2) of Ack11 inhibitor AIM-100 (5 μM for 1 hour at 30° C.) and immunoblotted with pTyr51-H4 (top panel), H4 (middle panel) and pTyr284-Ack1 (bottom panel) antibodies.
Figure 26C:
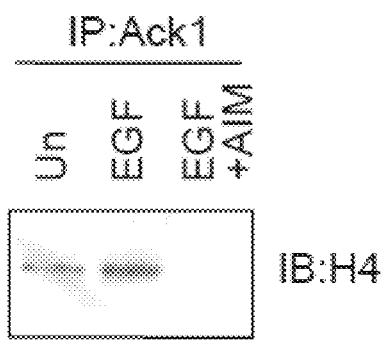
FIG. 26C is an immunoblot of cell lysates from HEK293 cells untreated, treated with EGF (column 2), or treated with EGF+AIM-100 (5 μM, 14 hour) (column 3) that were immunoprecipitated with Ack1 antibodies and immunoblotted with H4 antibodies.
Figure 26D:
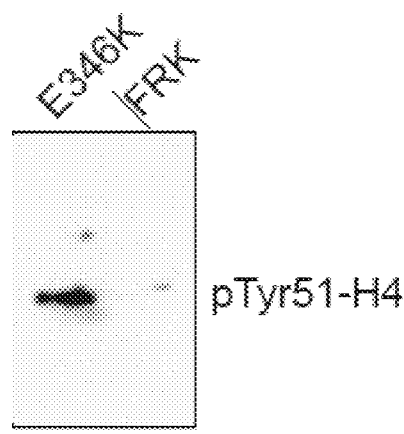
FIG. 26D is an immunoblot of cell lysates from serum-starved (24 h) HEK293 cells transfected with E346K-Ack1 (column 1) or FRK kinase (column 2) cells that were immunoprecipitated with pTyr51-H4 antibodies and immunoblotted with H4 antibodies.

To test whether Ack1 directly phosphorylates H4, in vitro kinase assay (Mahajan, K. et al. (2010) PLoS One, 5:e9646) was performed. Specifically, equimolar amounts of purified constitutively active E346K-Ack1 or kinase dead K158R-Ack1 and H4 proteins were incubated in the presence (or absence) of Ack11 inhibitor AIM-100, 5 uM for 1 hour at 30° C. and reaction mix was subjected to immunoblotting with pTyr51-H4, H4 and pTyr284-Ack1 antibodies. HEK293 cells were treated with EGF or EGF+AIM-100 (5 uM, 14 hour) and lysates were immunoprecipitated with Ack1 antibodies followed by immunoblotting with H4 antibodies. HEK293 cells were transfected with E346K-Ack1 or FRK kinase, cells were serum-starved (24 h) and lysates were immunoprecipitated with pTyr51-H4 antibodies followed by immunoblotting with H4 antibody. When purified E346K-Ack1 and H4 were incubated, H4 was Tyr51-phosphorylated, however, Ack1 inhibitor AIM-100 abrogated H4 pTyr51-phosphorylation (FIG. 26B). Co-immunoprecipitation experiment revealed that Ack1 binds to endogenous H4 (FIG. 26C). Moreover, Ack1-E346K when transfected in HEK293 cells, specifically phosphorylated H4 (FIG. 26D). Collectively these data indicates that Ack1 specifically phosphorylates H4 at Tyr51.

To identify regions in chromatin where H4 Tyr51-phosphorylation occurs and regulate gene expression, native ChIP-coupled DNA microarray analysis (ChIP-on-chip) was performed (Kim, T. H. et al. (2005) Nature, 436:876-880). The sheared chromatin from *Xenopus laevis* embryos injected with pTyr51-H4 antibodies or IgG was immunoprecipitated using a with pTyr51-H4 antibody followed by hybridization with *Xenopus* chip. It lead to the identification of ~550 potential sites/regions where pTyr51-H4 is present in *xenopus* genome. Many genes whose expression was upregulated multiple fold were developmentally regulated genes which indicated that H4 Tyr51-phosphorylation may have role to play in early development of embryos.

During gastrulation, cell movements result in a massive reorganization of the embryo from a simple spherical ball of cells, the blastula, into a multi-layered organism. During gastrulation, many of the cells at or near the surface of the embryo move to a new, more interior location. Epiboly is a cell movement that occurs in the early embryo, at the same time as gastrulation. It is one of many movements in the early embryo that allow for dramatic physical restructuring or morphogenesis. The movement is generally characterized as being a thinning and spreading of cell layers. Epibolic movements have been conserved in vertebrates and have been extensively studied in zebrafish and *Xenopus laevis*.

The onset of gastrulation in *Xenopus* is marked by the formation of a pigment line, which represents the formation of the dorsal blastopore lip and the beginning of specific morphogenetic movements (invagination and involution) of the mesoderm. This pigment line normally forms at the dorsal midline ~45° below the embryonic "equator"; as gastrulation progresses, it extends laterally and vegetally until the two ends join at the ventral midline to form a complete circle. The dorsal blastopore lip also moves steadily vegetalward, as a result of two other morphogenetic movements. The first of these is the spreading of the ectoderm in the animal cap region, referred to as epiboly. The second is a radial intercalation of internal mesoderm cells above the region of involution, which expands the surface area in the dorsal region below the "equator".

To understand physiological role of H4 pTyr51-phosphorylation, *Xenopus laevis* embryos were injected with pTyr51-H4 antibodies or AIM-100. In embryos injected with the pTyr51-H4 antibodies, epiboly was effectively blocked. The darkly pigmented animal cap cells remain in the animal region, instead of spreading vegetalward. As a result, the dorsal lip of the blastopore formed close to the equator, much higher than it normally does, and it did not move toward the vegetal pole. Although the blastopore lip eventually formed around the entire circumference, as it does normally, the mesoderm did not involute properly, and thus the embryo was unable to close the blastopore lip. Development was arrested at the early midgastrula stage. This phenotype appeared in 78% of surviving embryos injected with this antibody.

Embryos injected with Ack1 inhibitor AIM-100 too showed this epiboly block/involution failure in ~51% of surviving embryos, with a partial "reduced epiboly" phenotype appearing in an additional 14%. In the partial phenotype, the blastopore lip formed at a lower position, and the embryo progressed further in gastrulation before developmental arrest occurred. The affected embryos were unable to close the blastopore, however. The complete or partial inhibition of epiboly was not observed in any of the control-treated embryos.

While failure to close the blastopore is a common gastrulation defect that can arise from a wide range of causes, it is rare to see embryos in which epiboly is affected. Failure of involution is also rare, hence the disruption of epiboly as a reference for this phenotype was used summarized in Tables 3 and 4.

Effects of pTyr51-H4 antibodies or AIM-100 inhibitor on *Xenopus* Development, encompassing 9 independent experiments, are summarized in Table 3 and 4. The chief finding is that introduction of either the pTyr51-H4 antibodies or AIM-100 inhibitor resulted in a specific (and unusual) gastrulation defect. These treatments did not alter the timing or pattern of early cleavages. Embryos injected with either pTyr51-H4 (H4), pTyr37-H2B (H2B), or IgG show mortality rates of 22-25% by the onset of gastrulation (~20 hours after microinjection at the 2-cell stage, embryos maintained at 16° C.). Embryos injected with either AIM-100 or DMSO alone showed a mortality rate of 43-45% by this stage. Neither pTyr51-H4 nor AIM-100 lead to increased mortality at this stage; survival at subsequent stages is low because of the failure to complete gastrulation. Table 4 provides the phenotype distribution for surviving embryos (raw data are identical to those in Table 3).

In summary, these data demonstrate for the first time that Ack1 directly phosphorylates histone H4 at Tyr51 site which in turn regulates expression of multiple genes that are developmentally regulated. These genes plays a critical role in gastrulation especially epiboly formation, opening an exciting possibility that vertebrate embryo development is regulated by Tyr51-phosphorylated histone H4.

TABLE 3

Results of pTyr51-H4 antibodies and AIM-100 injections

| Sample | conc. | # | norm. | epib blk | epib red | abn/delay | dead | total |
|---|---|---|---|---|---|---|---|---|
| pTyr37-H2B | 200 ng/em | 3 | 49 (54%) | 0 | 0 | 19 (21%) | 23 (25%) | 91 |
| IgG | 200 ng/em | 3 | 44 (62%) | 0 | 0 | 10 (14%) | 17 (24%) | 71 |
| pTyr51-H4 | 200 ng/em | 5 | 15 (13%) | 73 (61%) | 0 | 4 (3.3%) | 26 (22%) | 119 |
| AIM-100 | 200 pM/em | 5 | 24 (11%) | 65 (29%) | 18 (8%) | 15 (6.7%) | 97 (43%) | 225 |
| DMSO | 20 nl/em | 5 | 48 (27%) | 0 | 0 | 48 (27%) | 80 (45%) | 176 |

"epib blk", epiboly block phenotype; "epib red", partial phenotype; "abn/delay", gastrulation is abnormal or delayed.

TABLE 4

Phenotypes of Surviving Embryos

| Sample | normal | epib blk | epib red | abn/delay | Tot survivors |
|---|---|---|---|---|---|
| pTyr37-H2B | 49 (72%) | 0 | 0 | 19 (28%) | 68 |
| IgG | 44 (81%) | 0 | 0 | 10 (18.5%) | 54 |
| pTyr51-H4 | 15 (16%) | 73 (78.5%) | 0 | 4 (4.3%) | 93 |
| AIM 100 | 24 (19%) | 65 (51%) | 18 (14%) | 15 (12%) | 128 |
| DMSO | 48 (50%) | 0 | 0 | 48 (50%) | 96 |

Example 4

Phosphorylation of Histone H2B at Tyrosine 37 Modulates microRNA Expression

With the experimental procedure as described in Example 1, this study identified a miRNA signature that is modulated specifically by WEE1 kinase, through phosphorylation of Y37-H2B. Such miRNAs include Mir26b, Mir149, Mir346, Mir350, Mir491, Mir599, Mir670, Mir708, Mir760, Mir879, Mir1192, Mir1965, Mir3058, and Mir5098, which are downregulated by pY37-H2B in cancer cells.

Example 5

Phosphorylation of Histone H4 at Tyrosine 88

HEK 293T cells were lysed in receptor lysis buffer (RLB) containing 25 mmol/L Tris (pH 7.5), 225 mmol/L NaCl, 1% Triton X-100, 1 mmol/L DTT, 10% glycerol, phosphatase inhibitors (10 mmol/L NaF, 1 mmol/L Na2VO4), and protease inhibitor mix (Roche). Following immunoprecipitation with pTyr-antibody beads (SantaCruz), beads were subjected to SDS PAGE electrophoresis and the gel was stained Coomassie Brilliant Blue-R250 (BioRad). A prominent band of ~11 kDa was excised, washed once with water and twice with 50 mM ammonium bicarbonate in 50% aqueous methanol. Proteins were reduced and alkylated with 2 mM Tris (2-carboxyethyl)phosphine hydrochloride (TCEP) (Sigma, St. Louis, Mo.) and 20 mM iodoacetamide (GE Healthcare, Pittsburgh, Pa.), respectively. Samples were digested overnight with modified sequencing grade trypsin (Promega, Madison, Wis.), Glu-C (Worthington, Lakewood, N.J.), or chymotrypsin (Roche, Switzerland). Peptides were extracted from the gel slices, phosphopeptides were enriched using IMAC spin columns (Pierce, Rockford, Ill.) or TiO2 Mono tip (GL Science, Japan). A nanoflow liquid chromatograph (Ultimate3000, LC Packings/Dionex, Sunnyvale, Calif.) coupled to an electrospray hybrid ion trap mass spectrometer (LTQ Orbitrap, Thermo, San Jose, Calif.) was used for tandem mass spectrometry peptide sequencing experiments. Peptides were separated with a C18 reverse phase column (LC Packings C18Pepmap) using a 40 min gradient from 5% B to 50% B (B: 90% acetonitrile/0.1% formic acid). The flow rate on the analytical column was 300 nl/min.

Figure 28:
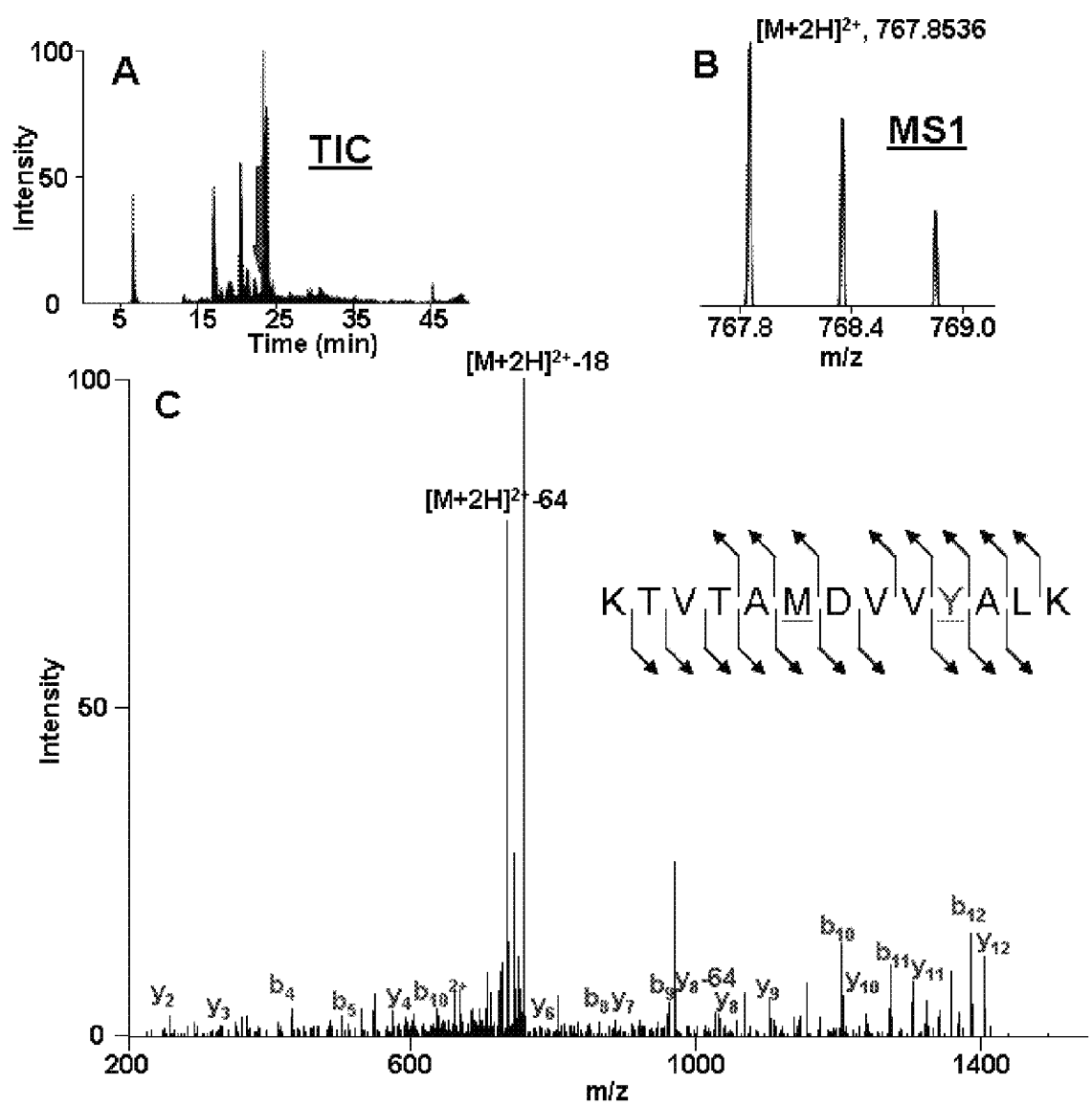
FIG. 28 shows that Tyrosine 88 residue is phosphorylated in histone H4. The peptide was detected at 23 minutes in the total ion chromatogram (FIG. 28A) with mass-to-charge ratio 767.8536 (FIG. 28B). The tandem mass spectrum matched the following sequence, (R)KTVTAMDVV YALK(R) (SEQ ID NO: 81; residues 2-14 literally disclosed in FIG. 28C) indicating that the C-terminal tyrosine was phosphorylated; the detection of the phosphotyrosine $b_{10}$ and $b_{11}$ is consistent with this localization (FIG. 28C). The assignment was made with Sequest XCorr 3.31 and ΔCN 0.25.

Five tandem mass spectra were acquired for each MS scan using 60 sec exclusion for previously sampled peptide peaks (Spray voltage 2.3 kV, 30% normalized collision energy, scanning m/z 450-1,600). FIG. 28 shows the mass spectrum of histone H4 Tyrosine 88-phosphorylated peptide. Sequences were assigned using Sequest (Thermo) and Mascot database searches against SwissProt protein entries of the appropriate species. Oxidized methionine, deamidation, carbamidomethyl cysteine, and phosphorylated serine, threonine and tyrosine were selected as variable modifications, and as many as 3 missed cleavages were allowed. The precursor mass tolerance was 1.08 Da and MS/MS mass tolerance was 0.8 Da. Assignments were manually verified by inspection of the tandem mass spectra and coalesced into Scaffold reports.

Generation and Purification of pY88-H4 Phospho-Antibody

Two histone H4 peptides were synthesized:

The phosphopeptide: TVTAMDVVpYALKRQGRT (SEQ ID NO: 65)

The non-phospho peptide: TVTAMDVVYALKRQGRT (SEQ ID NO: 64).

The monoclonal pY88-H4 antibody expressing hybridoma was custom generated by ProMab Biotechnologies, CA. In brief, mice were immunized twice with phosphopeptide, several weeks apart. The sera were affinity-purified. Antibodies recognizing the phospho-residue bound to the column which was eluted as phospho-specific antibodies.

Validation of pY88 Monoclonal Antibodies

To validate specificity of pY88 monoclonal antibodies, this example performed enzyme-linked immunosorbent assay or ELISA was performed. In brief, the Streptavidin coated 96-well plates (R&D systems) were incubated with biotinylated H4-derived unphosphorylated peptide TVTAMDVVYALKRQGRT (SEQ ID NO: 64, Y88 site is underlined) or biotinylated phosphorlated peptide TVTAMDVVpYALKRQGRT (SEQ ID NO: 65) for 1 hour.

The plates were washed with phosphate buffered saline containing 0.1% Tween 20 (PBST) and blocked in 3% BSA. The pY88-H4 antibodies (at 1:500 dilution) were added and incubated for 1 hour. Unbound antibodies were washed and HRP-conjugated anti-mouse secondary Antibodies (1:2000) were added. Magnitude of phosphorylation was detected using developer solution (OPD tablets, Sigma) and the plates were read at 450 nm. As a negative control, no peptide reactions were used. The pTyr antibodies were used as a positive control.

Figure 29:
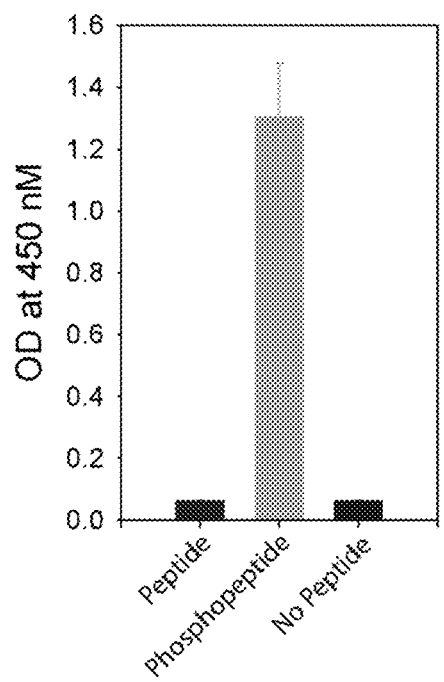
FIG. 29 shows the results of ELISA assay for antibody validation. Biotinylated unphosphorylated and Tyr88-phosphorylated H4 peptides were immobilized on streptavdin 96-well plates. Plates were incubated with pY88 monoclonal antibodies for 60 min at 37 C. ELISA was performed as described in text. Antibodies did not recognize unphosphorylated H4 peptide, however, Tyr88-phosphorylated peptide was recognized.

The pY88 monoclonal antibodies did not recognize unphosphorylated H4 peptide, however, Tyr88-phosphorylated peptide was recognized by monoclonal antibody (FIG. 29). These data validates the monoclonal antibody for its specificity towards histone H4 Tyr88-phosphorylation.

WEE1 and Ack1 Kinases Phosphorylate H4 at Tyr88

WEE1 and Ack1 are two non-receptor tyrosine kinases or NRTKs that have known nuclear functions. To determine whether WEE1 and Ack1 can directly target H4 for Tyr88-phosphorylation, this study performed in vitro kinase assay. In brief, the Streptavidin coated 96-well plates (R&D systems) were incubated with biotinylated H4-derived peptide TVTAMDVVYALKRQGRT (SEQ ID NO: 64) for 1 hour. The plates were washed and the purified WEE1 or Ack1 were added in kinase buffer (20 mM HEPES, 150 mM NaCl, 0.5% Triton X-100, 10% Glycerol, phosphatase and protease inhibitors) containing ATP and MgCl2. After 2 hours of incubation, plates were washed with phosphate buffered saline containing 0.1% Tween 20 (PBST) and blocked in 3% BSA. The pY88-H4 antibodies (at 1:500 dilution) were added and incubated for 1 hour. Unbound antibodies were washed and HRP-conjugated anti-mouse secondary Antibodies (1:2000) were added. Magnitude of phosphorylation was detected using developer solution (OPD tablets, Sigma) and the plates were read at 450 nm. As a negative control, no kinase and no peptide reactions were used. The biotinylated phosphopeptide TVTAMDVVpYALKRQGRT (SEQ ID NO: 65) was used as a positive control.

Figure 30:
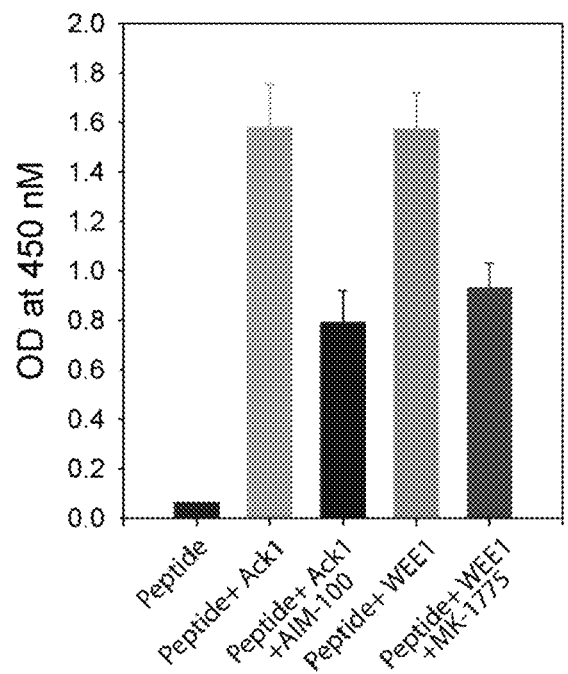
FIG. 30 shows that WEE1 and Ack1 kinases phosphorylate histone H4 at Tyr88. Biotinylated unphosphorylated and Tyr88-phosphorylated H4 peptides were immobilized on streptavdin 96-well plates. Purified WEE1 or Ack1 were added with or without WEE1 inhibitor MK-1775 or Ack1 inhibitor, AIM-100 for 60 min at 37 C. ELISA was performed as described in text. Antibodies recognized phosphorylated H4 peptide, however, when incubated with WEE1 or Ack1 inhibitors, H4 Tyr88-phosphorylaton was significantly reduced.

Incubation of H4 peptide with WEE1 and Ack1 protein resulted in robust H4 Tyr88-phosphorylation, which was detected by pY88 antibodies (FIG. 30). H4 Tyr88-phosphorylation was significantly decreased upon incubation of the reaction with WEE1 inhibitor, MK-1775 and Ack1 inhibitor AIM-100 (FIG. 30). Collectively, these data validates the monoclonal antibody for its specificity towards histone H4 Tyr88-phosphorylation and establishes rapid, accurate and relatively easy H4 Tyr88-phosphorylation detection method. Further, it indicates that WEE1 and Ack1 are the kinases that target histone H4 for Tyr88-phosphorylation. Moreover, small molecule inhibitors such as WEE1 inhibitor, MK-1775 or Ack1 inhibitor such as AIM-100 can suppress H4 Tyr88-phosphorylation.

Yeast Strain Lacking Tyrosine 88 Exhibits Lethal Phenotype

Histone residues within nucleosomes are evolutionarily conserved, e.g. the amino acid residues in histones H2A and H2B are more than 70% conserved from yeast to humans, and in histones H3 and H4 more than 90% are conserved. High evolutionary conservation can predict which amino acid is essential for cell survival by introducing mutations followed by assessing whether the mutation is lethal in yeast cells. Tyr88 mutations exhibited significant lethality in GRF167 background. Interestingly, a cluster of residues near the C terminus of histone H4 which include Tyr88, Leu90 and Tyr98, confer slow growth in more than one background. These residues form an important surface inside the nucleosome core. These residues could serve as a molecular spring that maintains tensile strength in the lower half of the nucleosome. Tyrosine 88 of H4 stacks on tyrosine 86 of H2B in the structure, forming a spring-like structure.

Example 6

Loss of Phosphorylation of Histone H3 at Tyrosine 99 Resulted in Loss of Weight

Figure 31:
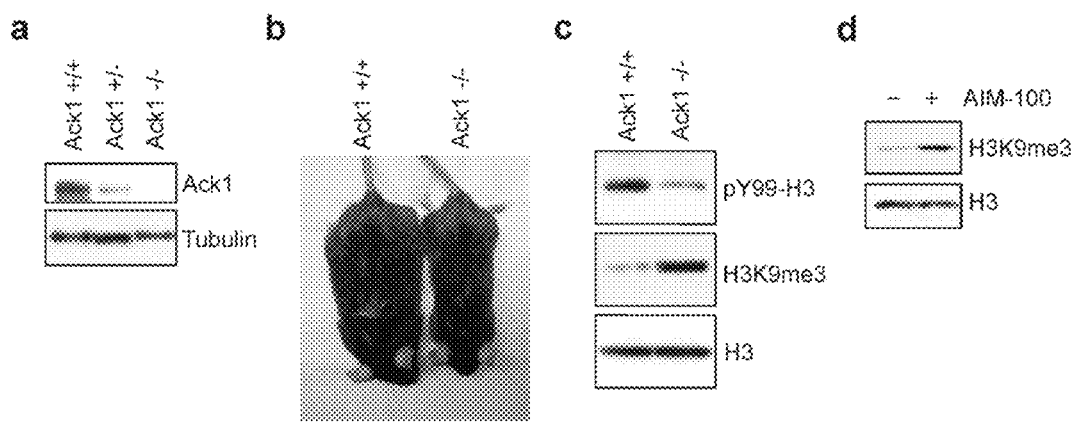
FIG. 31a shows the generation of Ack1 KO mice and activation. Wild type (+/+), heterozygous (+/−) and knock-out or KO (−/−) mice were euthanized and spleens were isolated. Immunoblotting of equal amount of spleen lysates was performed with Ack1 and tubulin antibodies. Wild type mice exhibit Ack1 expression which is significantly reduced in heterozygous mice (mice that has only one copy of the gene) and completely lost in knockout mice. The tubulin antibodies were used as a control to indicate equal amount of protein.
FIG. 31b shows that Ack1 KO mice are lean. Wild type (+/+) and knockout (−/−) mice are shown; the KO mice are significantly smaller and weigh lesser than their wild type counterpart.
FIG. 31c shows that Ack1 regulates histone H3 Tyr99-phosphorylation and negatively regulates H3 K9 trimethylation. The equal amount of testis lysates of Wild type (+/+) and knockout (−/−) mice were subjected to immunoblotting with H3-pTyr99 and H3K9me3 antibodies. Loss of Ack1 resulted in significant loss of H3 Tyr99-phosphorylation and increase in H3 K9 trimethylation. The histone H3 antibodies were used as a control to indicate equal amount of protein.
FIG. 31d shows that Ack1 inhibition upregulates H3 K9 trimethylation. The prostate cancer derived cells, LAPC4 were treated with AIM-100 (7 uM, 16 hours). The equal amount of cell lysates were subjected to immunoblotting with H3K9me3 and histone H3 antibodies. Loss of Ack1 activity by AIM-100 resulted in significant increase in H3 K9 trimethylation. The histone H3 antibodies were used as a control to indicate equal amount of protein.
Figure 32:
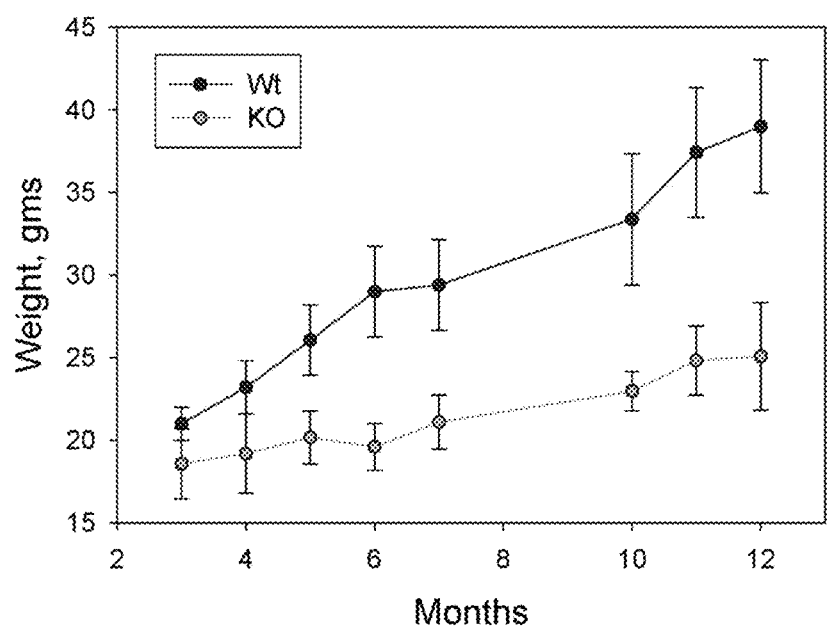
FIG. 32 shows that Ack1 KO mice were significantly lighter in weight than the wild-type counterparts.
Figure 33:
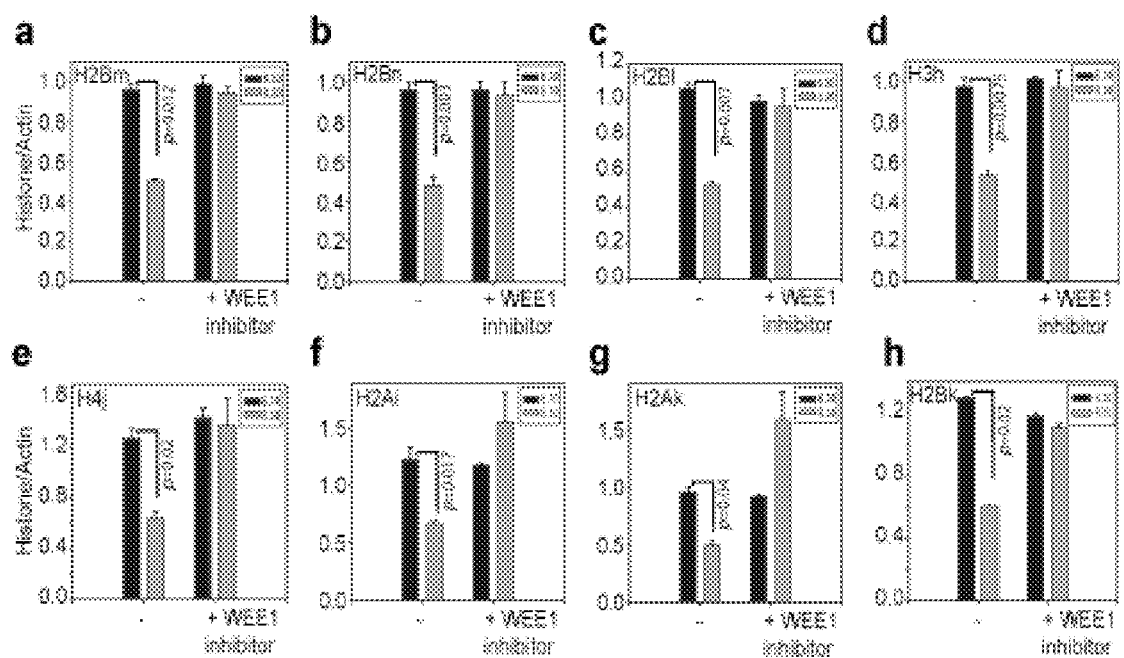
FIG. 33a-33h show a 8-histone gene signature. a-h, Synchronized cells treated with WEE1 inhibitor, MK1775 (0.6 uM, 14 hr) were harvested at indicated time points post-release. Total RNA was prepared followed by quantitative RT-PCR for 8 histone genes.

Ack1 kinase targets histone H3 for Tyr99-phosphorylation. To understand the role of Ack1/H3-pTyr99 signaling, this example generated knockout (KO) mice that lacked Ack1 genes (FIG. 31a). These Ack1 KO mice exhibited almost complete loss of H3 Tyr99-phosphorylation (FIG. 31c). Further, significant loss of weight, in some mice upto 50% weight loss was observed in these KO mice (FIG. 31b and FIG. 32). Significantly, apart from weight loss, Ack1 KO mice do not show any other problems or developmental defects.

Moreover, FIG. 31c shows that Ack1 regulates histone H3 Tyr99-phosphorylation and negatively regulates H3 K9 trimethylation. Additionally, upon inhibition of Ack1 with AIM-100, H3 K9 trimethylation was increased (FIG. 31d).

Example 7

Mechanistic and Clinical Studies of Phosphorylation of Histone H2B Tyrosine 37

WEE1 Mediated pTyr37-H2B Phosphorylation Suppresses Histone mRNA Synthesis

Modification of core histones has been demonstrated to regulate transcription, however, transcription of histone themselves were not known to be regulated by histone phosphorylation. To investigate whether pY37-H2B plays a direct role in regulating histone gene transcription, synchronized cells were treated (or untreated) with WEE1 inhibitor, MK-1775 and total RNA was isolated followed by qRT-PCR. Human cells have 55 distinct histone genes each encoding a fraction of core histones. This study determined histone levels using 20 of these genes. In untreated cells, rapid decrease in transcripts of all of these histone genes was observed when RNA levels of 6.30 hours post-release samples (late S phase) were compared with 8.30 hours post-release (G2/M phase) samples (FIGS. 33a-33h).

However, upon WEE1 inhibitor treatment, histone mRNA levels did not decrease in 8.30 hours post-release, indeed in some cases an increase was observed (FIGS. 33a-33h). Collectively, these data indicate that Y37-H2B phosphorylation represses transcription of the core histone genes located in Hist1 cluster. Based on extensive transcriptional profiling of 20 histone genes, this study identified 8 genes (H2Bm, H2bn, H2Bl, H3 h, H4j, H2Ai, H2Ak and H2Bk) as being representative of global histone transcriptional output, termed as the 8-histone gene signature.
Peptide Immunosandwich Assay (PIA)

Rapid and accurate detection of WEE1 activation and histone mRNA levels in GBM biopsies is an essential step towards developing a reliable companion diagnostic for WEE1 inhibitor MK-1775. Using the high specificity monoclonal antibodies, this study develped a Peptide Immunosandwich Assay that detects WEE1 epigenetic activity with high sensitivity even from small tumor resections.

In brief, Streptavidin coated 96-well plates (R&D systems) were incubated with biotinylated human histone H2B derived peptides KRSRKESYSVYVYKVL (SEQ ID NO: 62, Y37 site is underlined). H2B derived phospho-peptide KRSRKESpYSVYVYKVL (SEQ ID NO: 63) was used as positive control. Any unbound areas on the plate were blocked with 3% BSA. Next, purified WEE1 protein (100 ng) prepared in kinase buffer (20 mM HEPES, 225 mM NaCl, 1% Triton X-100, 10% glycerol, phosphatase and protease inhibitors) supplemented with 1 uM ATP and 1 uM $MgCl_2$. After 2 hours of incubation, plates were washed with phosphate buffered saline containing 0.1% Tween 20 (PBST) and reblocked in 3% BSA. The pY37-H2B or pTyr antibodies (at 1:1000 dilution) were added and incubated for 1 hour. Unbound antibodies were washed and HRP-conjugated anti-mouse secondary antibodies (1:5000) were added. The magnitude of phosphorylation was detected using developer solution (OPD tablets, Sigma) and after 20 minutes of incubation, the plates were read at 450 nm.

Figure 34:
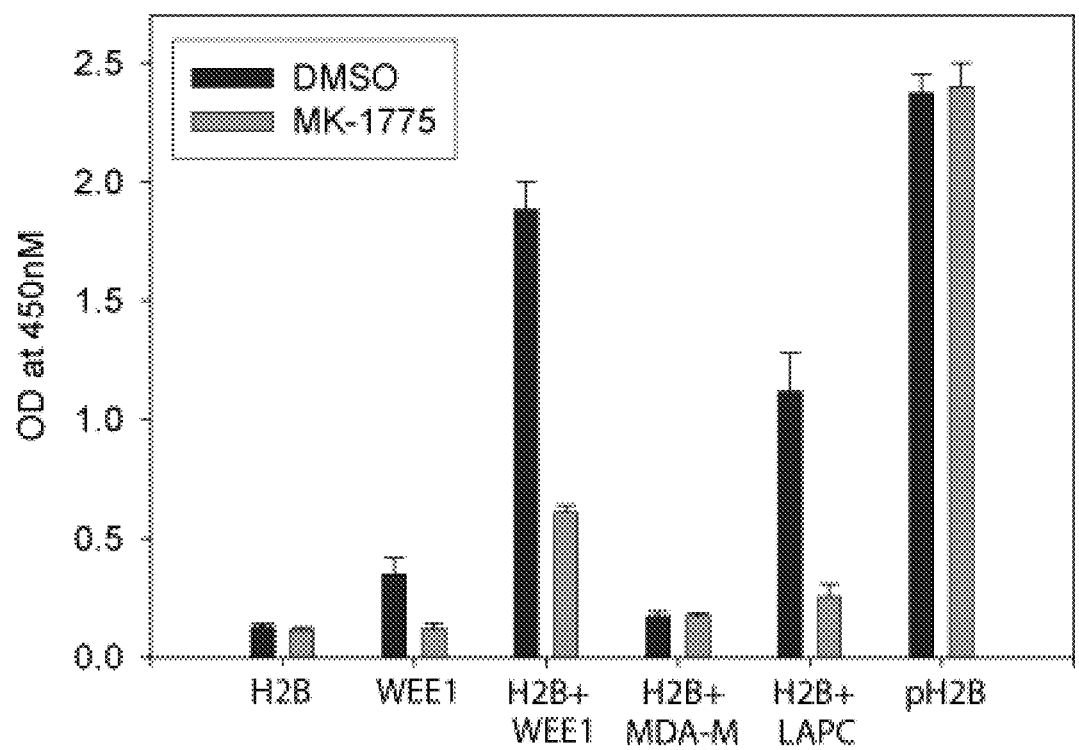
FIG. 34 shows the results of the Peptide Immuno sandwich Assay (PIA). Purified WEE1 or cell lysates were incubated with H2B peptide with or without WEE1 inhibitor MK-1775 for 2 hours at 37° C. H2B Tyr37-phosphorylation was determined as described in the text.

The Peptide Immunosandwich Assay was first validated using purified WEE1 protein (100 ng) and cancer derived cell lines (50 ug). Purified WEE1 exhibited robust H2B Tyr37-phosphorylation and a significant decrease in pY37-H2B levels was observed upon incubation with 5 uM of MK-1775 (FIG. 34). PIA was also validated using cancer derived cells lines MDA-MB231 (low WEE1 activity) and LAPC4 cells (high WEE1 activity). As expected, MDA-MB231 cell lysates exhibited significantly lower levels of H2B Tyr37-phosphorylation as compared LAPC4 (FIG. 34). As negative controls, H2B peptide alone or WEE1 enzyme alone were used. Tyr37-phosphorylated peptide was used as a positive control (FIG. 34). All the reactions were performed in triplicates and the data shown is from three distinct biological repeats. The Peptide Immunosandwich Assay assay was also validated by simultaneously performing it with HRP-conjugated pTyr antibodies (pY20-HRP Ab, Santacruz). Near identical results were obtained with pTyr antibodies.

Figure 35:
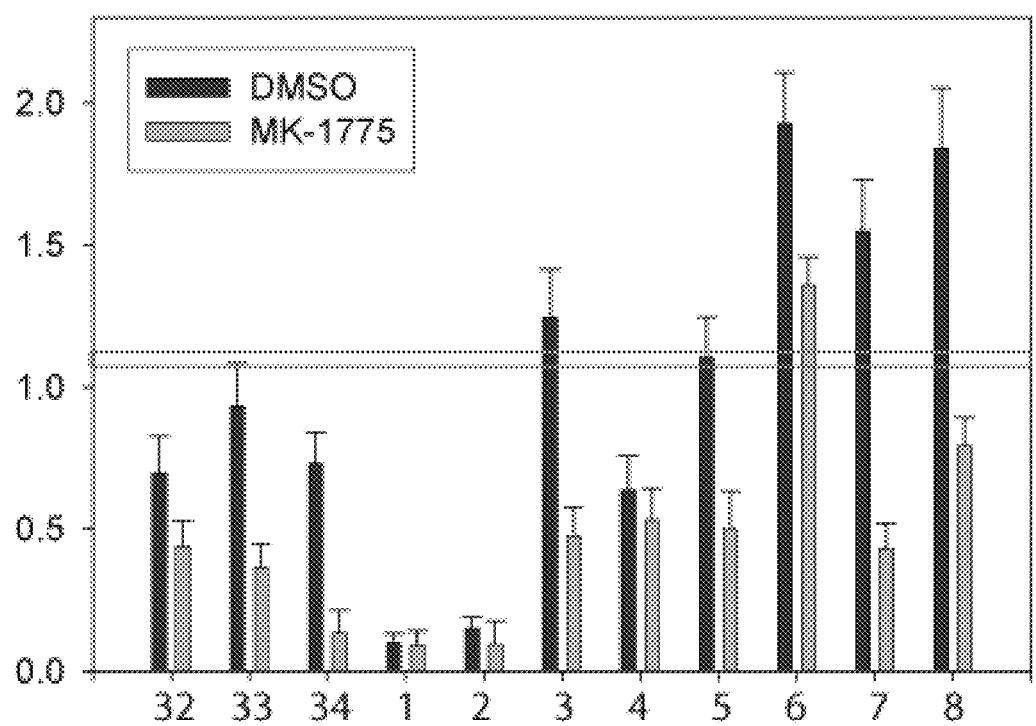
FIG. 35 presents the results from PIA performed using lysates prepared from Glioblastoma Multiforme (GBM) and normal brain samples treated with or without MK-1775. Threshold interval is shown.

To assess the WEE1 epigenetic activity in GBM patients, lysates were prepared from 8 GBM tumor biopsies and 3 normal brain samples as a control. The lysates were quantitated and 100 ug of lysates was used per reaction. Each reaction was performed in triplicates. GBM and normal brain lysates were incubated with either DMSO or MK-1775 (10 uM) for 30 minutes followed by Peptide Immunosandwich Assay as described above. A Student's t-test and Mantel-Haenszel $\chi 2$ test was performed to examine whether there is an increasing trend for WEE1/pTyr37-H2B expression with respect to normal versus GBM tumors. It led to determination of 'threshold-interval' of OD of 1.1, suggesting that those tumors that exhibit more than 1.1 OD in PIA assay possess high WEE1 epigenetic activity. It revealed that 4 out of 8 GBM samples (patient#3, 6, 7 and 8) exhibited significant increase in H2B Tyr37-phosphorylation as compared to normal brain samples (patient#32, 33 and 34). Further, WEE1 activity in GBM tumor lysates was significantly reduced upon MK-1775 treatment (FIG. 35). The increased WEE1 epigenetic activity in tumors of patient#3, 6, 7 and 8 was also confirmed by immunoblotting using pY37-H2B antibodies (data not shown).

Collectively, these data established rapid, accurate, sensitive and relatively easy detection method for WEE1 epigenetic activity in human brain tumor samples. Further, it indicates that loss of WEE1 activation by MK-1775 can also be efficiently monitored by assessing H2B Tyr37-phosphorylation levels post-treatment.
Quantitative Measurement of WEE1 Epigenetic Activity in GBM Using Peptide Immunosandwich Assay (PIA)

The data indicates that WEE1 directly phosphorylates H2B and regulates histone transcriptional activation. Although WEE1 inhibitor MK-1775 is FDA approved, it has not been widely used for GBM treatment. One of the reasons is that to date a molecular test that can accurately assess WEE1/pY37-H2B signaling in GBMs is not available. One of the objectives of this proposal is to develop a companion diagnostic test for detection of WEE1/pY37-H2B signaling in GBM samples which can facilitate MK-1775 therapeutic regimen. The PIA test developed is comparatively inexpensive, relatively easy to perform and can be rapidly performed by trained technicians in most laboratories and cancer centers. Successful completion of this project would lead to establishment of a reliable and relatively easy companion diagnostic kit that can accurately detect WEE1 epigenetic activation in GBM samples.

PIA test performed at smaller scale, using 11 human brain samples (preliminary results shown in FIG. 4) revealed that PIA can accurately detect increased WEE1 epigenetic activity in a subset of GBM patients. Deciphering of optimal 'threshold-interval' is critical for PIA to be used widely a companion diagnostic. This can only be accomplished by rigorous testing of PIA in a larger cohort of GBM and normal samples. The first specific aim of this proposal is geared towards achieving this goal. This study has acquired 50 GBM samples and 15 normal samples. 100 more tumor and normal biopsy samples will be made available upon first initial screening under the same protocol. The lysates will be prepared from 65 brain samples (50 GBM samples and 15 normal brain samples) followed by quantitation of WEE1 epigenetic activity by PIA as described above. Purified WEE1 and extracts of cell lines, MDA-MB231 and LAPC4 cells, will be used as controls. As a negative control, MK-1775 treated cell lysates or reaction will be used. A range of concentrations of purified WEE1 (0.1-10 uM) will also be used to obtain a standard curve. Each GBM or normal brain sample (100 and 200 ug of protein) will be assayed in triplicate. Comparison of the above reading with readings from standard curve will allow us to precisely quantitate activated WEE1 levels in tumors and normal samples. Using multiple GBM samples, a range of WEE1 activation level will be deciphered, defined as 'threshold-interval', that is indicative of activated status of WEE1 kinase in tumors.

For compilation and analysis of the quantitative data to determine whether the biopsy demonstrates activation of WEE1/H2B signaling pathway and responsive to WEE1 inhibitor regimen (Standard development) data from 50 GBM samples will be used. Initially the samples will be evaluated in a non-blinded manner to address the question of whether tumor samples possess significantly higher levels of WEE1 expression as compared to normal brain samples. Subsequently additional GBM and normal brain samples with unknown WEE1 status will be evaluated in a blinded manner.

Using a two-sided two-sample T-test, this study can achieve 100% power to detect the difference between groups with a stringent alpha level set at 0.01 (when adjusting for multiplicity). Further, the Mantel-Haenszel $\chi 2$ test will be performed to examine whether there is an increasing trend for WEE1/pTyr37-H2B expression with respect to normal/benign versus GBM tumors. Analysis of variance will be performed to examine whether the expression levels of WEE1 differ among normal/benign versus different stages of GBM tumors. Boxplots will be used to summarize the intensity distribution at each progression stage. The statistical analyses will be carried out using software SAS, R, and Matlab when appropriate.

WEE1 overexpression has also been observed in Triple Negative Breast Cancer (TNBC) tumors. TNBCs are those breast cancers that do not express the genes for estrogen receptor (ER), progesterone receptor (PR) or Her2/neu. These are known to be more aggressive with poor prognosis and often occur in younger women.

Quantitative Measurement of Histone mRNA Levels in GBM by qRT-PCR

It is important that activation of WEE1/pY37-H2B signaling in GBM biopsies is further confirmed by another independent method. Towards this goal, this study will assess corresponding decrease in global histone mRNA levels upon overexpression of WEE1 in GBM tumor samples. This study has standardized the quantitative RT-PCR strategy for 8 histone genes (shown in FIG. 33a-33h), which is representative of global histone transcription. In this specific aim, this study will assess this 8-histone gene signature in GBM samples.

For the construction of standard curves, serial dilutions of GBM or normal sample RNA will be used (50, 10, 2, 0.4, 0.08, and 0.016 ng) per reverse transcriptase reaction. One "no RNA" control and one "no Reverse Transcriptase" (No RT) controls will be included for the standard curve. Three reactions will be performed for each sample: 10 ng, 0.8 ng, and a No RT (10 ng) control. Real-time quantitative PCR analyses will be performed using the ABI PRISM 7900HT Sequence Detection System (Applied Biosystems). All samples will be tested in triplicate wells each for the 10 ng and 0.8 ng concentrations. PCR will be carried out with SYBR Green PCR Master Mix (Applied Biosystems) using 2 μl of cDNA and the primers in a 20-μl final reaction mixture. Dissociation curves will be generated for each plate to verify the integrity of the primers and RNA. Data will be analyzed using SDS software version 2.2.2 and exported into an Excel spreadsheet. The actin data will be used for normalizing the gene values; i.e., ng gene/ng actin per well.

The 65 samples used for PIA will also be used for RNA isolation followed by qRT-PCR. It is expected that those tumors that exhibit significant WEE1 expression would also have lower levels of histones. Correlation between WEE1 activation and histone downregulation will be explored using Spearman ranked correlation analysis. Statistical differences between the tumor and normal samples will be determined using log-rank test. The association of the WEE1-positive tumors exhibiting lower histone levels will also be assessed for survival by using the Kaplan-Meier method as described in Applicants' previous publications. This study has survival information of all the 65 individuals from whom the biopsies are taken, which overall would provide us correlation between WEE1 overexpression, downregulation of histone gene expression and disease progression.

To additionally confirm that modulation in 8-histone gene signature is dependent on WEE1 epigenetic activity, this study will utilize five primary GBM tumors. These cells will be treated with MK-1775 or DMSO, RNA will be isolated and upregulation in 8-histone gene signature in MK1775 treated cells will be validated.

Examining the Use of PIA & Histone Signature to Follow Response of GBMs to MK-1775 Treatment The purpose of this study is to determine whether WEE1-positive GBM tumors, identified by PIA and 8-histone gene signature display sensitivity to the potent WEE1 inhibitor, MK-1775. This would validate PIA and 8-histone gene signature as 'companion diagnostics' for MK-1775 therapy—a foundation for personalized medicine approach for brain cancer patients for the first time.

To accomplish this, this study established five distinct GBM cell lines, derived from brain cancer patients. Second, WEE1-positive nature of these cell lines was confirmed by immunoblotting for pY37-H2B marker, PIA and qRT-PCR of core histone mRNA. Two of these brain tumor derived cell lines are WEE1-positive and three are found to be negative. These cell lines will be utilized in this specific aim.

GBM Xenograft Studies

To determine the antitumor efficacy of MK-1775 on GBM progression in vivo, this study will first implant I million GBM cells subcutaneously (SC) into nude mice and the mice will be injected with various doses of MK-1775 (0, 20, 50 μM) 20 days after tumor cells implantation. 5 injections will be performed on alternate days and tumor growth (and its inhibition upon MK-1775 injection) will be monitored for 8 weeks. Tumors will be removed and analyzed for inhibition of WEE1-mediated pY37-H2B phosphorylation by PIA and Western blotting. Further, increased histone mRNA levels will be assessed by qRT-PCR.

In Vivo Analysis Using the U251 and E98 Orthotopic GBM Mouse Models

In addition to subcutaneous injection of GBM cells, one million human GBM cells will also be injected intracranially into nude mice. GBMs derived established cell lines, U251 MG and E98, which are transduced to express Fluc and mCherry will be used. U251-FM and E98-FM cells will be treated daily with MK-1775 or DMSO via an intraperitoneal (IP) injection starting at day 14 after injection of the GBM cells. Mice will be injected for 10 days at the dose of MK-1775 (0, 20, 50 μM) and tumor growth will be monitored for 8 weeks by using bioluminescence imaging (IACUC#4151R). It is expected that the mice treated with MK-1775 would exhibit a significant tumor regression after WEE1-inhibitor injections. MK-1775 induced G2 checkpoint arrest and cell death will also be determined by mitosis-specific staining of xenograft tumor sections using immunohistochemistry.

Assess the Epigenetic Landscape Orchestrated by Aberrant WEE1 Signaling in GBMs

Glioblastoma multiforme (GBM), a tumor of the glial cells, is the most common malignant brain cancer in adults, accounting for ~13,000 deaths per year in U.S. alone. Currently, GBM is treated by surgical removal of tumor, followed by radiation and chemotherapy. Regrettably, most patients die within a year from new secondary tumor foci forming within a centimeter of the resected area. The molecular basis of GBM is unknown, which has made research into understanding the biology of GBM and identification of therapeutic targets the areas of intense interest in the scientific community. Recently, gene expression profiling revealed that the WEE1 kinase is overexpressed in GBMs. Further, MK-1775, a potent WEE1-specific inhibitor has been shown to selectively induce apoptosis in WEE1 expressing cancer cell lines.

To understand molecular pathogenesis of WEE1 overexpression, this study first evaluated the genomic loci marked with H2B Tyr37-phosphorylation in normal eukaryotic cells. Native ChIP-sequencing was performed using synchronized mouse embryo fibroblasts (MEFs) in late S phase, i.e., 6.5 hrs post-thymidine release when cells exhibit peak H2B Tyr37-phosphorylation. As a control, MEFs were harvested from G1 phase that lack expression of H2B Tyr37-phosphorylation. ChIP with pY37-H2B antibodies in these cells lead to the identification of 3524 potential sites/regions where pY37-H2B marks are present; 1240 of which were present within genes while 351 sites were present upstream and 326 sites were downstream of genes. Interestingly, two classes of genes emerged to be specifically marked by pY37-H2B phosphorylation marks; these were DNA and histone modifying genes. Interestingly, a few genes involved in stemness were also identified. A partial list of these genes is shown in Table 5.

TABLE 5

Chromatin modifying and stemness genes marked by pY37-H2B epigenetic mark

| Gene | Functional role | Fold changes |
|---|---|---|
| IDH2 | In gliomas and melanomas, IDH2 increased histone methylation and decreased 5-hydroxylmethylcytosine | pY37-H2B down-regulates IDH2 levels by at least 5 fold in gliomas and metastatic melanomas |
| DNMT3B | DNA methyltransferase | pY37-H2B down-regulates DNMT3B levels by at least 3 fold in gliomas and metastatic melanomas |
| JARID2 | Transcriptional repressor interacts with the Polycomb repressive complex 2, regulates H3K27 trimethylation | pY37-H2B down-regulates JARID2 levels by at least 2 fold in gliomas and metastatic melanomas |
| EYA3 | Phosphatase, involved in DNA damage-induced dephosphorylation of Tyr-142 of H2A.X | pY37-H2B down-regulates EYA3 levels by at least 2 fold in gliomas and metastatic melanomas |
| JMJD2c | Histone demethylase, converting specific trimethylated histone residues to the dimethylated form | pY37-H2B down-regulates JMJD2c levels by at least 2 fold in gliomas and metastatic melanomas |
| JMJD1C | Histone demethylase | pY37-H2B down-regulates JMJD1c levels by at least 2 fold in gliomas and metastatic melanomas |
| CREBBP | Histone acetyl transferase and scaffolding protein | pY37-H2B down-regulates CREBBP levels by at least 2 fold in gliomas and metastatic melanomas |
| SOX 4 and 18 | Essential for glioma-initiating cells to retain their stemness | pY37-H2B down-regulates SOX4 and 18 levels by at least 2 fold in gliomas and metastatic melanomas |

This study used two methods (CHIP-seq and RNA-seq) that are complementary, and integration of these two data sets provided the comprehensive insight into pathways altered in invasive cancers such as GBM.

Figure 36:
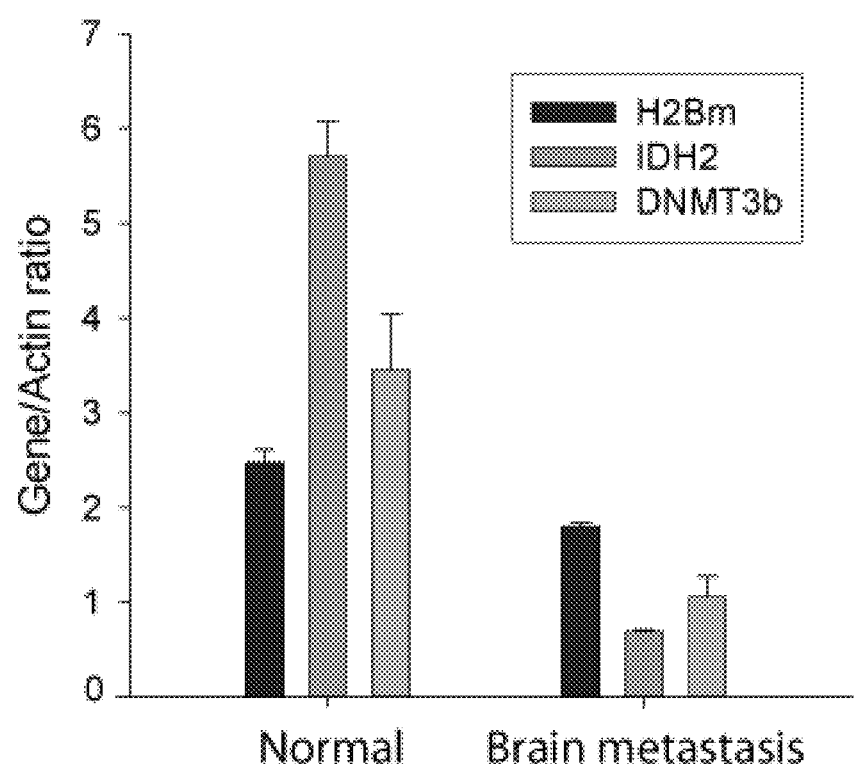
FIG. 36 shows the suppression of IDH2 and DNMT3b expression in GBM. Total RNA was prepared from normal and tumor samples followed by quantitative RT-PCR using primers corresponding H2Bm, IDH2 and DNMT3b.

This study used ChIP-sequencing and RNA sequencing techniques followed by integrative bioinformatics analysis to obtain the epigenetic signature of WEE1/pY37-H2B signaling in GBM tumors. Using 60 GBM tumors obtained from patients, the inventors have generated multiple 'GBM patient-derived cell lines' under neurosphere condition, also known as 'Brain tumor initiating cells' or BTIC. We have also developed a qRT-PCR based approach to accurately determine increased WEE1/pY37-H2B signaling in a given GBM tumor tissue. One such example is shown in FIG. 36 wherein RNA was isolated from a pair of normal and brain metastatic tumor samples followed by qRT-PCR for histone H2Bm, IDH2 and DNMT3b. As expected, increased WEE1/pY37-H2B signaling resulted in decrease in not only histone H2B mRNAs but also DNA modifying enzymes e.g. IDH2 and DNMT3b.

To identify WEE1 regulated epigenetic signature, two WEE1/pY37-H2B signaling positive GBM patient-derived cell lines will be treated with 0.6 µM of WEE1 inhibitor MK-1775 or DMSO and will be subjected to native ChIP-sequencing as described in Applicants' publication. In brief, GBM patient-derived cell lines will be lysed in RLB buffer and sonicated for 25 seconds to shear DNA to an average length of 300-500 bp. The soluble chromatin will be incubated overnight at 4° C. with pY37-H2B antibody or IgG antibodies (control) and protein-G magnetic beads (Active motif). The complexes will be washed, eluted and chromatin immunoprecipitated DNAs will be first analyzed for the presence of site II region of Hist1 cluster by PCR. The inventors have previously established site II as a recurring region at which pY37-H2B marks are deposited by WEE1. Once enrichment of Site II in GBM chromatin immunoprecipitates is confirmed, the samples will be subjected to sequencing on the Illumina Genome analyzer as described in Applicants' publication.

It is shown that WEE1 overexpression could result in constitutive suppression of histone synthesis, decrease in global histone levels, which could result in loss of heterochromatinization, activating a distinct transcription program. Therefore, deciphering the unique transcriptional program modulated by WEE1's epigenetic alteration of chromatin will provide significant understanding at molecular level for initiation and progression of disease. Towards this goal, this study will analyze global expression patterns of polyadenylated transcripts in the four WEE1/pY37-H2B signaling-positive GBM tumor samples and equal number of normal biopsies by RNA sequencing (RNA-Seq). In addition, RNA will also be prepared from GBM patient-derived cell lines treated with MK-1775 (0.6 µM for 24 hours) or DMSO. In brief, total RNA will be isolated from tumor or normal tissues using TRIzol Reagent. Sequencing libraries will be prepared according to Illumina RNA-Seq library kit. Paired-end RNA-Seq 36 base pair reads will be aligned and DESeq will be used to normalize raw read counts and analyze differential gene expression. USeq 7.0 will be used to generate gene-level read counts and estimate RPKM (reads per kilobase of exon per million reads mapped). Only genes with expression values >1 RPKM in at least one tumor will be considered for subsequent analysis. Expression will be normalized to the interquartile range across the time course; interquartile numbers will then be used for clustering using a cosine angle distance metric and the HOPACH clustering.

ChIP-Sequencing yield is expected to be ~40 million reads in each sample, of which ~27 million are expected to be mapped uniquely to the human genome. The 36-nt sequence reads (tags identified by using Illumina's Genome Analyzer 2) will be mapped to the genome using the ELAND algorithm. 'Peaks' will be calculated and compiled into BED files (Browser Extensible Data). A typical threshold setting is in the range of 10-20, but may be adjusted depending on the number of tags sequenced or based on the information on positive and negative test sites, independent estimates for the false discovery rate (FDR), and/or the intent to generate a stringent or relaxed analysis. Using the MEME program unique motifs in ChIP data will be identified. FIMO will be used to map motifs found in MEME onto the peaks revealing genes that could be potentially regulated by H2B Tyr37-phosphorylation. Moreover, MetaCore (from GeneGo Inc) enrichment analysis will be used to cluster genes, which are adjacent to ChIP-sequencing peaks. This enrichment analysis clusters the genes based on their functional role.

For RNA-sequencing, the data will be analyzed in similar manner as described above. It is expected that ~13,000 genes are expressed in tumor tissues. Genes will be clustered by expression pattern using HOPACH, yielding distinct clusters including groups of genes specifically expressed at each stage (e.g., Clusters A, L, N, and S). The stage-specific clusters will be enriched for expected Gene Ontology (GO) terms and tabulated as described in Applicants' publication.

One study will focus on the eight genes identified above, collectively referred to as 'candidate genes'. IDH2 and DNMT3B identified in earlier pY37-H2B ChIP-sequencing and six additional DNA and histone modifying genes chosen from ChIP-sequencing and RNA-sequencing of GBM tumors, described above. The rationale behind studying IDH2 and DNMT3B genes is described below:

IDH2 or Isocitrate Dehydrogenase 2

DNA methylation at the 5 position of cytosine (5-mC) is a key epigenetic mark that is critical for various biological and pathological processes. 5-mC is converted to 5-hydroxymethylcytosine (5-hmC) by the ten-eleven translocation (TET) family of DNA hydroxylases. IDH2 catalyzes the production of a-ketoglutarate, which is an essential cofactor in the reaction catalyzed by TET. The loss of 5-hmC has been identified to be the epigenetic hallmark in melanoma, and downregulation of isocitrate dehydrogenase 2 (IDH2) and TET family enzymes has emerged as a critical step underlying 5-hmC loss. Reintroduction of the 5-hmC by active TET2 or IDH2 suppressed tumor growth and increases tumor-free survival in animal models. It is contemplated that in GBMs tumor cells overexpressing WEE1, pY37-H2B may epigenetically suppress expression of IDH2 gene, to prevent formation 5-hmC facilitating tumor growth and proliferation.

DNMT3B

DNMT3B, a member of the DNA methyl transferase family, methylates cytosine at 5 position to epigenetically regulate gene expression. Often, cancer cells, including GBMs, are characterized by global DNA hypomethylation due to the aberrant activity of DNA methyl transferases. Hypomethylation at pericentric chromatin associated with chromosomal instability was observed in cells expressing DNMT3B splice variant. It is contemplated that by placing pY37-H2B marks in DNMT3B upstream regulatory sequences, GBMs may suppress DNMT3B levels imposing aberrant DNA methylation patterns within pericentric heterochromatin leading to genetic instability.

Directed ChIP-PCR to Validate Presence of WEE1 and pY37-H2B at the Promoter and Enhancer Regions of Candidate DNA and Histone Modifying Genes To validate the regulation of DNA and histone modifying genes by WEE1 mediated H2B Y37-phosphorylation, ChIP followed by real time PCR will be performed as described earlier in Applicants' publication. In brief, chromatin will be prepared from GBM patient-derived cell lines treated with 0.6 µM of WEE1 inhibitor, MK-1775 or DMSO. ChIP will be performed using pY37-H2B antibodies (IgG as a control) followed by gPCR of immunoprecipitated DNA with primers corresponding to upstream promoter, enhancer and intragenic regions of 8 candidate DNA and histone modifying genes. This experiment will validate whether specific inactivation of WEE1 kinase activity would lead to loss of pY37-H2B epigenetic marks upstream of (or within) candidate genes, unleashing their transcriptional activity.

Validation and Quantitative Analysis of Candidate Gene Expression in GBMs

To examine whether reorganization of chromatin landscape by WEE1 mediated H2B Y37-phosphorylation suppresses expression, qRT-PCR will be performed using candidate gene specific primers. In brief, total RNA prepared from 50 freshly frozen GBM tumors and 10 normal brain samples will be subjected to qRT-PCR. In addition, this study will also use 5 GBM patient-derived cell lines treated with 0.6 µM of WEE1 inhibitor, MK-1775 or DMSO. Real time RT-PCR is expected to reveal relative decrease in candidate gene transcription levels in tumor samples as compared to normal brain samples. Further, MK-1775 treated GBM cell lines are expected to exhibit significant increase in candidate gene transcription due to loss of WEE1/pY37-H2B signaling. In addition to qRT-PCR, modulation in expression of candidate genes will be assessed by immunoblotting with specific antibodies in GBM cell lines that were treated with MK-1775 or DMSO (as a control).

In terms of further validation, there is a "matched set" of 200 GBM samples has been generated at Moffitt on which gene expression arrays and targeted exome sequencing data for 1326 genes (including WEE1, IDH2, DNMT3B and Sox4 and 18) is available along with extensive clinical data e.g. survival, treatment etc. This highly informative and useful data set will also be utilized to assess aberrant expression (and mutational) status of the candidate genes and its association with survival and treatment responses.

TMA Staining of GBMs to Correlate WEE1/pY37-H2B Signaling to Correlate Expression with Severity of Disease To examine the role of WEE1/pY37-H2B signaling in GBM, this study will perform immunohistochemical (IHC) staining of TMA. The study has generated TMA comprised of clinically annotated GBM (n=325) tumor samples, which has been extensively validated by staining with multiple IHC-validated antibodies. This TMA has been constructed from a prospective Case-Control Cohort study that has extensive clinical follow up and quality control. This study will section the GBM TMA and perform IHC staining with WEE1, pY37-H2B, IDH2, DNMT3B, and 6 other candidate gene antibodies.

A significant increase in expression of WEE1 and pY37-H2B is expected in GBM cancers compared to normal controls. In contrast, a significant decrease in expression of IDH2, DNMTB3B and other 4 candidate genes is expected in GBM samples as compared to normal brain tissues. This study will perform ANOVA analysis to determine whether WEE1, pY37-H2B IDH2, DNMTB3B and other 6 candidate gene expressions differed significantly among different stages (p value less than 0.05 will be considered as significant) as described in earlier papers from Applicants' laboratory. This study will also perform Tukey-Kramer analysis to examine all pairwise differences between different stages; the expression levels WEE1 and pY37-H2B are expected to be significantly higher in GBM than those of normal or earlier tumor stages. This study will perform Kaplan-Meir analysis, which is expected to reveal whether patients with high expression of WEE1 and pY37-H2B are at a higher risk for cancer-related deaths. Furthermore, this study will determine whether expression of WEE1 is significantly correlated with pY37-H2B in situ by calculating Spearman rank correlation coefficient ($\rho=0.5$ or above will be considered significant).

Functional and Mechanistic Characterization of WEE1/pY37-H2B Targets

To further investigate and validate the molecular role of WEE1/pY37-H2B epigenetic signaling in GBM pathogenesis, this study will study the requirement of these genes in specific cellular processes. This will allow us to address whether specific alterations in epigenetic landscape contribute to the invasive phenotype of GBM. This study will specifically assess the following processes:

Effect of Depletion of Candidate Genes on GBM Cell Proliferation

The expression of individual candidate target genes will be downregulated in GBM patient-derived cell lines using specific small-interfering RNA (RNAi) and confirmed by immunoblotting with specific antibodies. To determine the effect of candidate target depletion on cell proliferation, the ability of cells to synthesize DNA will be assayed using the chemical method of incorporation of 5-ethynyl-2'-deoxyuridine (EdU) and its subsequent detection by a fluorescent azide through a Cu(I)-catalyzed [3+2] cycloaddition reaction. In brief, Edu will be added at a final concentration of 10 uM for 2 h, cells will be fixed with 4% paraformaldehyde and cells will be processed for measuring DNA synthesis as described in the Click-it—Edu Alexa Flour 488 Flow Cytometry Assay protocol (Invitrogen). Decrease in Edu incorporation in RNAi treated cells but not control cells will be suggestive of loss of proliferative capacity, and will indicate that the particular candidate gene is essential for glioblastoma cell growth.

Effect of Depletion of Candidate Genes on Cell Cycle Progression

GBM patient-derived cell lines transfected with control or target specific siRNA, will be harvested after 48 hours, and processed for flow cytometric analysis as described above. As an additional control, primary GBM cell lines will be treated with MK-1775 or DMSO (as control). Samples will be analyzed using the FACS Calibur flowcytometer, and cell cycle analysis was carried out using the Mod Fit program. If the cells are found to arrest at specific stages of the cell cycle in the control cells but not in the MK-1775 cells, then this study will conclude that this could be one potential mechanism by which WEE1 regulates glioblastoma progression.

WEE1/pY37-H2B Signaling in Maintaining Neurosphere Formation

Figure 37:
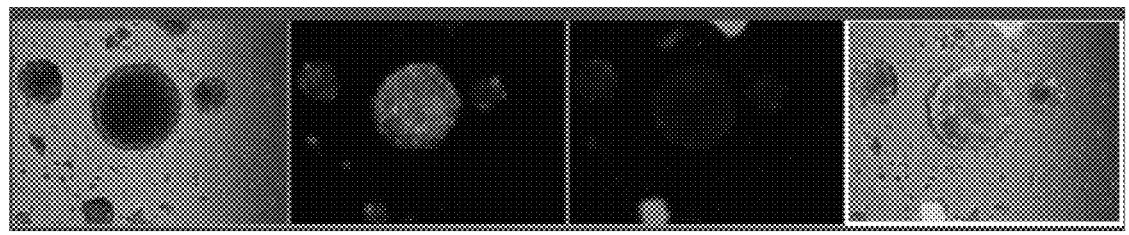
FIG. 37 shows images for monitoring neurosphere formation of patient derived GBM cell line BTIC5.

Neurospheres are free-floating clusters that contain neural stem cells. ChIP-sequencing revealed that genes such as Sox4 and Sox18 that are essential for glioma-initiating cells to retain their stemness are marked by pY37-H2B. Towards the goal of examining role of the WEE1-pY37-H2B signaling in maintaining stemness, neurosphere assay will be performed. This assay interrogates three fundamental characteristics of neural stem cells: proliferation, self-renewal, and multipotency. This study has developed 4 distinct GBM patient-derived cell lines that form neurospheres when cultured in specially reconstituted stem cell culture media (FIG. 37). It shows neurosphere formed by BTIC5 cell line transfected with pLVX-ZsGreen (panel 1 and 2). Panel 3 shows its low staining with Hoechst 33342, stem cell side population cells have the capability to exclude Hoechst 33342 by a multi-drug like transporter (FIG. 37).

To determine whether WEE1/pY37-H2B signaling is essential to maintain stemness of the GBM population, mRNA will be prepared from MK-1775 (0.6 µM) or DMSO treated neurospheres. This study will analyze expression markers characteristic of the stem cell phenotype and pluripotency, such as Sox4, Sox18, nanog homeobox (NANOG), POU class 5 homeobox 1 (POU5F1) or OCT4, and SRY-box 2 (SOX2) by qRT-PCR. Morever, this study will analyze whether MK-1775 either alone or in combination with temozolomide, an alkylating agent (specific aim 3) abolishes neurosphere formation and propagation. These data will reveal whether WEE1/pY37-H2B signaling is needed for maintaining GBM neurosphere formation potential.

Determine Whether WEE1/pY37-H2B Epigenetic Signaling Prevents Formation 5-mC and 5-hmC by Suppressing DNMT3B and IDH2 Expression To test the hypothesis whether increased WEE1/pY37-H2B signaling suppresses IDH2 and DNMT3B expression and thus formation 5-mC and 5-hmC, respectively, this study will assess global 5-mC and 5-hmC levels in GBM and normal brain samples using the EpiMark 5-hmC and 5-mC analysis Kit (New England Biolabs). This robust and highly reproducible PCR-based assay utilizes the differential methylation sensitivity of the isoschizomers Mspl and HpaII to quantitate the presence of 5-hmC and 5-mC. In brief, 5-hmC present in genomic DNA isolated from ~40 GBM tumor and 10 normal brain samples will be glucosylated (unmodified or 5-mC containing DNA will not be affected) followed by digestion. Mspl and HpaII recognize the same sequence (CCGG) but are sensitive to different methylation status. HpaII will cleave unmodified site while Mspl will recognize and cleave 5-mC and 5-hmC, but not 5-ghmC. PCR will be performed using primers corresponding to known locations e.g. pericentric heterochromatin and the CpG sites that contain 5-hmC. If the CpG site contains 5-hmC, amplification will occur after glucosylation and digestion, but not in the samples lacking 5-hmC. It is expected that real time PCR will reveal that GBM samples have significantly lower 5-mC and 5-hmC levels as compared to normal samples. In addition, 4 GBM patient-derived cell lines treated with 0.6 µM of WEE1 inhibitor MK-1775 or DMSO will also be used to determine5-mC and 5-hmC levels. Consequently, this study expects to see an increase in 5-hmC levels in Wee1 inhibitor treated samples.

Validation of Lowering 5-mC and 5-hmC Levels in GBM by Immunohistochemical Staining of TMA To examine the role of WEE1/pY37-H2B signaling in regulating 5-mC and 5-hmC levels and correlate it to GBM disease progression, this study will perform immunohistochemical (IHC) staining of brain cancer TMA as described in specific aim 1. IHC grade antibodies for 5-mC and 5-hmC are commercially available from LifeSpan BioSciences. A significant decrease in expression of 5-mC and 5-hmC is expected when GBM tumors are compared to normal samples. This study will perform ANOVA and Tukey-Kramer analysis to examine all differences. This study will also determine whether overexpression of WEE1 and pY37-H2B is significantly correlated with downregulation of 5-mC and 5-hmC in situ by calculating Spearman rank correlation coefficient (p=0.5 or above will be considered significant).

ChIP-PCR Analysis to Determine Increased Recruitment of Histone Transcriptional Suppressor HIRA at pY37-H2B Marked Sites in GBM This study discovered for the first time that a rapid cascade of events is initiated when WEE1 is recruited to the chromatin by the transcriptional co-activator NPAT upstream of Hist1 cluster. The pY37-H2B epigenetic marks acts as a docking site for the recruitment of histone repressor, HIRA, to down regulate expression of multiple histone genes of Hist1 cluster. In this specific aim this study will explore whether pY37-H2B epigenetic mark uses a similar mechanism to down regulate expression of IDH2, DNMT3B and other candidate genes. ChIP with HIRA antibody or IgG antibodies as control will be performed in primary GBM derived cell lines that are treated with WEE1 inhibitor MK-1775 (DMSO as control) followed by real time PCR of DNA using primers corresponding to IDH2, DNMT3B and other 6 candidate genes. The results from these studies will have a significant impact on the understanding of how candidate chromatin modifying genes such as IDH2 and DNMT3B are compromised in tumors. This acquires particular significance in those tumors that do not display loss of function mutations in these genes.

Figure 38:
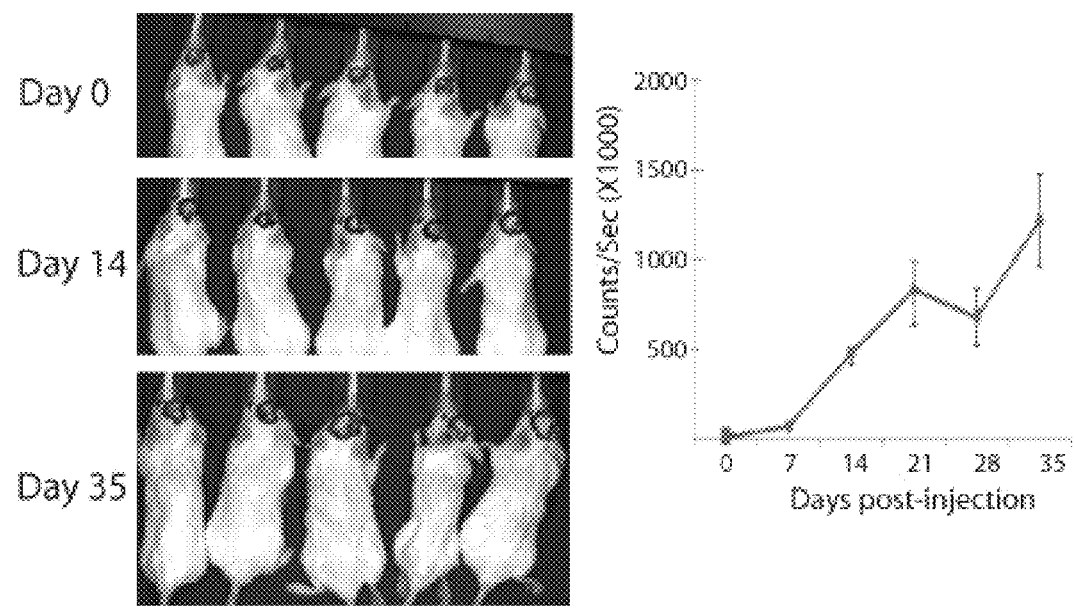
FIG. 38 shows the monitoring of xenograft growth of mice injected with brain cancer cells. Mice were injected with U52-luc cells and scanned every 7 days for the growth of the tumor.

Determine the Ability of WEE1 Inhibitor MK-1775 to Mitigate the Growth of Xenograft Tumors by Activating Expression of Chromatin Modifiers This study will use two different brain cancer cell lines, U51 and U251 N for xenograft studies. The inventors have generated stable U87 and U251 N cells that express luciferase and eGFP (FIG. 38). In brief, U51 and U251 N cell lines will be injected into the caudate nucleus of the right cerebral hemisphere of the brains of NOD/SCID mice. In addition to U51 and U251 N cell lines, this study will also perform this experiment using two GBM patient derived cell lines (BTICs), including BTIC5, shown in FIG. 37. With four different cell types (n=20 mice), total 80 mice will be used. For each mouse, $1 \times 10^5$ cells/0.002 ml will be injected and tumor growth will be characterized by weekly imaging using the IVIS 200 in vivo fluorescence imaging system. Of 20, 10 mice will be administered with MK-1775 after a period of latency to tumor formation (i.e. 14 days post-injection). A dose of 10 mg/kg/day of MK-1775 will be injected intraperitoneally (IP) every day for 10 days and suppression of tumor growth will be confirmed by non-invasive bio-imaging. The other half of the mice will be injected IP with 10% DMSO solution. The significance of this system is that the tumor cells can be identified ante mortem in mice. Further, responses to treatments can also be monitored in vivo ante mortem. After a period tumor growth, previously determined to be approximately 35 days, mice will be euthanatized. At this time, tumors will be resected and evaluated post mortem in the lab. It is expected that WEE1 kinase inhibition by MK-1775 will result in at least partial regression of xenograft tumor growth. To confirm the role of chromatin modifiers in tumor growth, total RNA will be isolated from resected xenograft tumors and qRT-PCR for histone mRNAs (for assessing decreased WEE1 activity) and candidate genes will be performed. It is expected that MK-1775 mediated inhibition of WEE1/pY37-H2B signaling will lead to increased level of DNA and histone modifiers genes, suppressing tumor growth.

Statistical analysis for xenograft studies: Ten animals are planned for each of the groups. Using a two-sided two-sample T-test, with 10 animals in each group, this study will achieve 100% power to detect the difference between groups with a stringent alpha level set at 0.01 (when adjusting for multiplicity).

Interrogate Mechanisms by which pY37-H2B Promotes DNA Repair and Resistance to DNA Alkylating Agents During S phase WEE1 appears to track not only completion of DNA replication and genetic integrity by pTyr15-phosphorylation of Cdc2 but also completion of histone synthesis by marking chromatin with H2B pTyr37-phosphorylation, before cells enter mitosis. Thus WEE1 behaves as a sensor of chromatin integrity and agents that can compromise this function can lead to mitotic infidelity, chromosome loss, and apoptosis. Not surprisingly, WEE1 inhibitor, MK-1775, is able to sensitize cancers and cancer cell lines cells to certain DNA damaging agents such as gemcitabine, 5-fluorouracil that activate intra-S phase checkpoint. This appears not to be solely limited to WEE1's role in regulating G2/M entry, but to additional functions in S phase. Moreover, cells treated with agents that can inhibit both DNA synthesis (hydroxyurea) and inhibit WEE1, were found to contain a marked increase in disorganized mitotic spindles and abnormal mitoses.

H2B Y40-Phosphorylation Function is Conserved in *S. cerevisiae*

Figure 39:
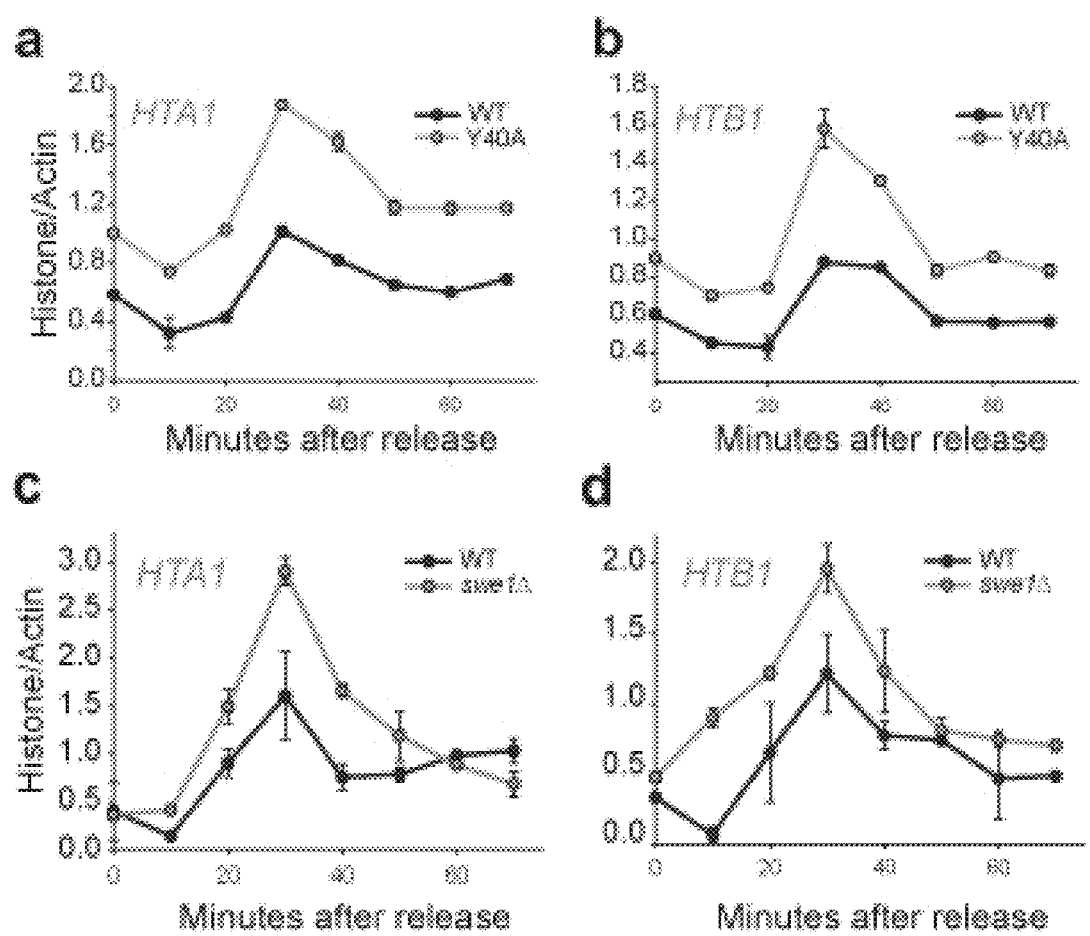
FIG. 39a-39d show that budding Yeast H2B Y40 phosphorylation suppresses transcription of histone genes. The WT and Y40A mutant yeast cells (FIGS. 39a and 39b) and the WT and swe1Δ mutant yeast cells (FIGS. 39c and 39d) were synchronized, RNA was prepared followed by qRT-PCR for histone transcripts.

Budding yeast, *Saccharomyces cerevisiae*, is a genetically tractable model organism to study the functional roles of variety of post-translational modifications in histones and histone transcriptional activation. It was observed that H2B Tyr37 site is evolutionarily conserved and is equivalent to Y40 in *S. cerevisiae*. To examine H2B Tyr40-phosphorylation regulates histone transcription, mRNAs were isolated from the WT and H2B-Y40A mutant yeast followed by qRT-PCR. The WT cells exhibited peak histone mRNA synthesis at 30 min post a-factor release followed by rapid decrease, however, H2B-Y40A mutant yeast exhibited significant increase in histone mRNA levels over the WT at 30 min post a-factor release (FIGS. 39a and 39b). Similarly, loss of SWE1 (WEE1 homolog is called SWE1 in *S. cerevisiae*) resulted in significant increase in all histone levels (FIGS. 39c and 39d). Taken together, these data indicate that the kinase, the substrate and the post-translational modification is evolutionarily conserved.

Yeast H2BY40A Mutants Display Marked Sensitivity to DNA Alkylating Agents

Figure 40:
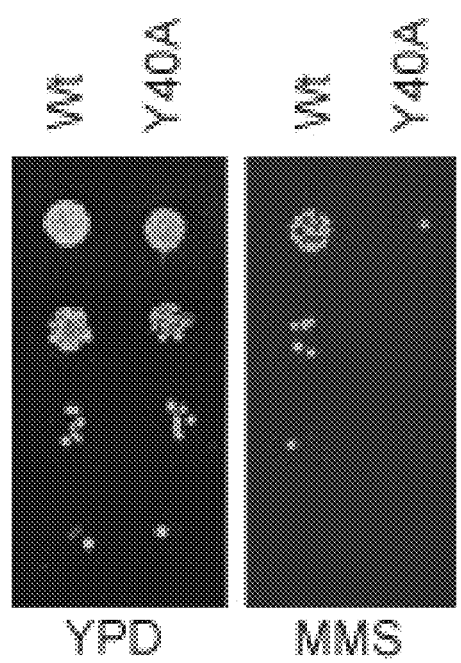
FIG. 40 shows that Yeast H2BY40A mutants display marked sensitivity to MMS. Wt and H2BY40A mutants were serially diluted and spotted on YPD plates in the absence or presence of MMS and growth was assessed 72 h post-plating.

To test whether excess of histones interfere with the ability of cells to repair DNA damage, *S. cerevisiae* wildtype (Wt) and H2BY40A mutants were exposed to DNA alkylating agent Methylmethane suplhonate (MMS). MMS inhibits DNA replication by methylating adenine or guanine in the DNA to cause base mispairing and stalling of replication forks, until the mutated/alkylated bases are excised out and replaced with the normal bases by the DNA alkyl transferases or the nucleotide repair machinery. In contrast to the wild type cells, H2BY40A mutants exhibited acute sensitivity to MMS similar to the checkpoint kinase mutant rad53 (FIG. 40). Rad53 is a functional homologue of human Chk1 and Chk2 in budding yeast. It not only senses DNA replication stress during S phase but also acts as a surveillance machinery to detect excess histones that are not packaged into chromatin and targets them for degradation.

Figure 41:
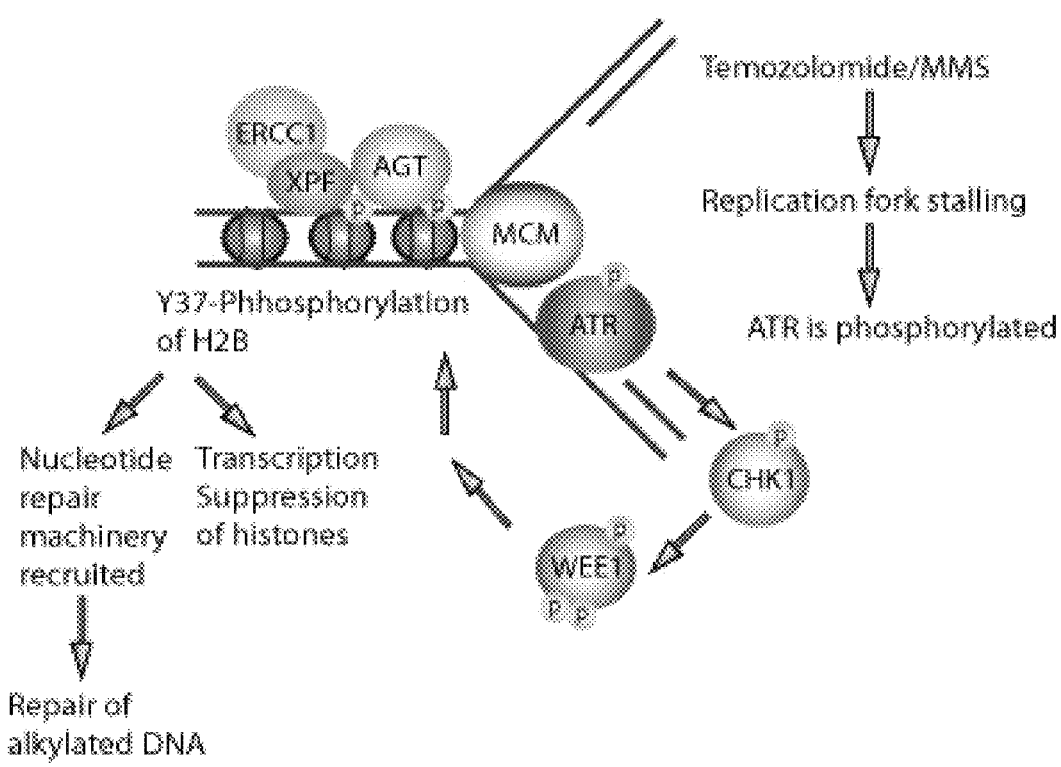
FIG. 41 presents a proposed model for epigenetic regulation of DNA alkylation repair. The DNA replication checkpoint kinase ATR is activated in response to replication stress such as stalled replication forks, which phosphorylates the checkpoint kinase Chk1 that arrest cells in intra-S phase. Chk1 in turn phosphorylates and activates WEE1 which marks damaged chromatin with pY37H2B. pY37-H2B recruits the DNA alkyl transferases (AGT or MGMT) or the nucleotide excision repair machinery (ERCC1/XPF) to the DNA damage caused by alkylating agents to promote repair.

The acute sensitivity of the yeast H2BY40A mutants to MMS suggests that H2B Tyr40-phosphorylation is critical to overcome DNA damage and sensitivity may be due to three non-mutually exclusive mechanisms; (1) By not recruiting factors facilitating base-excision repair or nucleotide excision repair; (2) by interfering with DNA repair by increasing nucleosomal density, and (3) by a failure to arrest cells in S phase with damaged DNA. This finding is particularly significant in GBM, as alkylating neoplastic agents such as temozolomide are routinely used to treat patients. Temozolomide methylates guanine at $0^6$ position in the DNA, interferes with replication of the DNA strand to arrest cells in S phase, and if the damaged is not repaired it leads to apoptosis. Interestingly, cancer cells upregulate expression of enzymes such as $0^6$ methyl guanine methyl transferase (MGMT), which confers resistance to DNA alkylating agents by removing the methyl groups efficiently. Moreover, expression of high levels of MGMT is inversely correlated with angiogenicity and invasiveness of GBM. Based on these data, it is contemplated that WEE1 mediated H2B Tyr37-phosphorylation acts as 'beacon' for recruitment of DNA repair machinery e.g. AGT, ERCC1 and XPF (FIG. 41) or it may relay the damage signal to the Chk1 S phase checkpoint kinase to arrest cells. In the absence of H2B Tyr37-phosphorylation, recruitment of AGT, ERCC1 and XPF and repair of alkylating DNA is impaired, eventually leading to apoptosis. These data indicate that combinatorial treatment with Temozolomide and MK-1775 could be a novel and highly relevant strategy for treatment of GBM patients. To test this hypothesis this study will pursue the following experiments.

Examine Whether Loss of Y37 Phosphorylation Sensitizes GBM Cells to DNA Alkylating Agents GBM cell lines U373 (MGMT negative), U138 (moderate expression of MGMT), LN18 and T98G (high expression of MGMT) obtained from ATCC (American Type Culture Collection), will be treated with different doses of the WEE1 inhibitor MK-1775 and Temozolomide. Cell viability will be assayed by WST-1 proliferation assay and cell cycle arrest will be assessed by flow cytometry as described in Applicants' publications. As shown in the schematic pY37-H2B is expected to have a protective effect due to its ability to recruit the repair or checkpoint machinery to the temozolomide-induced alkylated bases. In Wee1 inhibitor treated cells, in the absence of phosphorylation, the repair or checkpoint pathways are not active and have catastrophic consequences. It is believed that significant toxicity will be observed in GBM cells treated with MK-1775 and alkylating agents. This finding will be crucial to initiate a clinical trial on combining WEE1 inhibitors with DNA alkyating agents to treat GBM patients.

Investigate Whether pY37-H2B Recruits DNA Repair Enzymes or Relays Signals to Checkpoint Kinases in Cells Treated with Alkylating Agents To further investigate interaction of DNA repair proteins with pY37-H2B epigenetic mark, Phospho-peptide pull down assays will be performed as described in Applicants' paper. Primary GBM-derived cell line treated with a MK-1775, Temozolomide, MK-1775+Temozolomide or DMSO as control. Extracts will be incubated with biotinylated pY37-H2B or control peptides that are immobilized on streptavidin beads. Interaction of pY37-H2B with DNA repair proteins will be assessed by immunoblotting with specific antibodies (anti-ERCC, anti-XPF and anti-MGMT or anti-AGT antibodies or anti-Chk1 antibodies). Immunoprecipitation of MGMT or excision repair proteins will be an important proof of the mechanism by which pY37-H2B might epigenetically regulates DNA repair and promote resistance to alkylating agents. Alternatively, this study will perform mass-spectrometry analysis of the pY37-H2B phospho-peptide pull down in cells treated with DNA alkylating agents to identify proteins interacting with this modification. Non-phospho peptides will be used as control.

Determine Whether Excess Histones Increase Nucleosomal Density in GBM Cell Lines The increased MMS sensitivity of the yeast H2BY40A mutants could be due to increased heterochromatinization as a result of excess histone gene expression due to loss of WEE1 mediated regulation. To test this hypothesis this study will first determine nucleosomal density in GBM cell lines untreated and treated with WEE1 inhibitor. Briefly, nuclei will be isolated and the intact nuclei will be digested with micrococcal nuclease, followed by nucleosomal DNA purification using EZ Nucleosomal DNA Prep Kit (Zymoresearch). Non-nucleosomal DNA is specifically degraded using micrococcal nuclease, while nucleosomes bound DNA will be protected, and exhibit a periodic ladder like pattern of ~150 by or higher. The nucleosomal DNA will be further analyzed by agarose gel electrophoresis. Presence of high molecular weight or non-digested DNA in the WEE1 inhibitor treated will confirm Applicants' hypothesis that increased histones leads to increased nucleosomal density and heterochromatinzation phenotype. The results from these studies will suggest that excess histones interfere with access of DNA repair machinery to damaged bases in the DNA, leading to cell death. The results obtained from study with the GBM cell lines will be validated using the yeast H2BY40A mutant and wildtype as control. This kit works well for isolation of mammalian and yeast nucleosome-associated DNA.

Evaluate Sensitivity of GBM Orthotopic Tumors to Combination of MK1775 and Temozolomide To assess whether combinatorial targeting with DNA alkylating agent temozolomide and MK-1775 can efficiently overcome GBM tumor growth, U51 and U251 N cell lines, will be injected into the brains of NOD/SCID mice as described in Specific Aim 2 (n=30 mice, total 60 mice). 10 mice will be administered with temozolomide, or with MK-1775 and temozolomide or with DMSO, 14 days post-injection. Both, MK-1775 and temozolomide will be injected at a dose of 10 mg/kg/day intraperitoneally for 10 days and suppression of tumor growth will be confirmed by non-invasive imaging the mice. It is expected that combinatorial treatment of MK-1775 and Temozolomide will not only cause base alkylation, but also cause failure of the DNA damage repair machinery to be efficiently recruited due to the loss of WEE1/pY37-H2B signaling activity. Inability of repair of the alkylated DNA would result in cell cycle arrest, leading to cell death. Overall, it is expected that combination of these two inhibitors will markedly suppress GBM tumor growth.

Example 8

Histone H2B Phosphorylation at Tyrosine 37 by WEE1 Kinase and its Role in Glioblastoma Multiforme (GBM), Melanoma and Prostate Cancer The precise orchestration of epigenetic signaling networks ensures timely gene expression profiles that are critical to safeguard against catastrophic cellular events. Components of these epigenetic signaling pathways include writers, readers and erasers, each of which plays a critical role in regulated gene expression. Importantly, deregulation of epigenetic mechanisms is linked to cancer, hereditary and metabolic diseases (Probst, A. V. et al. (2009) Nat. Rev. Mol. Cell. Biol., 10(3):192-206; Schwartzentruber, J. et al. (2012) Nature, 482(7384):226-231; Wu, G. et al. (2012) Nature Genetics, 44(3):251-253; Sturm, D. et al. (2012) Cancer Cell, 22(4):425-437; Brower, V. (2011) Nature, 471(7339): S12-S13; Burgess, R. J. et al. (2013) Nat. Struct. Mol. Biol., 20(1):14-22). Applicants recently discovered the existence of a novel epigenetic signaling network wherein WEE1 kinase directly phosphorylates the histone H2B (pY37-H2B) to cause repression of global histone synthesis, precisely in the late S phase of the cell cycle (Mahajan, K. et al. (2012) Nat. Struct. Mol. Biol., 19(9):930-937). Mechanistically, it was observed that pY37-H2B epigenetic marks recruit the HIRA transcriptional repressor, exclude the transcriptional co-activator, NPAT, to temporally suppress mRNA synthesis, providing a key evidence of how cells use this epigenetic signaling pathway to precisely coordinate duplication of DNA and histones during each cell cycle (Mahajan, K. et al. (2012) Nat. Struct. Mol. Biol., 19(9):930-937; Mahajan, K. et al. (2013) Trends in Genetics: TIG, 29(7):394-402). Consonantly, it was observed that a WEE1-specific small molecule inhibitor, MK-1775 (now AZT-1775) not only inhibited WEE1 epigenetic activity but also robustly reversed histone transcriptional suppression, in both yeast and mammalian cells, indicating that WEE1/pY37-H2B epigenetic signaling has an universal applicability (Mahajan, K. et al. (2012) Nat. Struct. Mol. Biol., 19(9):930-937; Mahajan, K. et al. (2013) Trends in Genetics: TIG, 29(7): 394-402). Based on these data and without being bound by theory, Applicants suggest that WEE1/pY37-H2B epigenetic signaling plays a critical role in chromatin replication by silencing histone transcription that can be reversed by WEE1 inhibitor, MK-1775. Applicants also established the novel epigenetic reader function of HIRA and its role in suppression of global histone output. Further, it was demonstrate that the reversal of pY37-H2B epigenetic marks by MK-1775 could overcome loss of heterochromatinization' caused by abridged histone synthesis in WEE1 overexpressing cancer cells.

Serendipitously, Applicants discovered that the pY37-H2B marks are instantaneously erased after IR-induced DNA damage and are restored after about 2 hours when majority of the DSBs are repaired. The removal of these marks was found to be dependent on the activity of Ataxia telangiectasia mutated (ATM) kinase, a master regulator of the DNA damage signaling pathway. Thus, these data indicate that another regulatory layer is involved in the deposition of pY37-H2B epigenetic marks. Applicants investigated how these marks are erased in a timely manner by EYA and CDC14 tyrosine phosphatases.

Interestingly, in light of Applicants' recent discovery, the evolutionarily conserved WEE1 epigenetic function acquires a new dimension—WEE1 is aberrantly expressed in highly aggressive tumors such as glioblastoma multiforme (GBMs), malignant melanomas and triple-negative & luminal breast cancers (Mir, S. E. et al. (2010) Cancer Cell, 18(3):244-257; Wuchty, S. et al. (2011) PloS One, 6(2): e14681; Magnussen, G. I. et al. (2012) PloS One, 7(6): e38254; Aarts, M. et al. (2012) Cancer Discov., 2(6):524-539; Iorns, E. et al. (2009) PloS One, 4(4):e5120). To decipher its puzzling role in malignancy, Applicants mined the ChIP-sequencing data which revealed that in addition to HIST1, pY37-H2B marks are also deposited at a tumor suppressor gene—the isocitrate dehydrogenase 2 (IDH2). This gene encodes a key enzyme in the pathway catalyzing the conversion of methyl group at the 5' position of cytosine (5-mC) to 5-hydroxymethylcytosine (5-hmC) (Xu, W. et al. (2011) Cancer Cell, 19(1):17-30)—a metabolite significantly reduced in malignant cancers (Xu, W. et al. (2011) Cancer Cell, 19(1):17-30; Haffner, M. C. et al. (2011) Oncotarget, 2(8):627-37; Jin, S. G. et al. (2011) Cancer Res., 71(24):7360-7365; Orr, B. A. et al. (2012) PLoS One, 7(7):e41036; Lian, C. G. et al. (2012) Cell, 150(6):1135-1146). While IDH2 mRNA expression is down regulated in brain and skin cancers, the mechanistic basis of its transcriptional suppression was not known. Therefore, Applicants profiled 27 primary GBM biopsies and 6 normal brain samples and observed that a subset of the GBMs (about 26%) exhibited elevated WEE1 mRNA levels coupled with a striking downregulation of IDH2 mRNA transcription.

Therefore, Applicants demonstrated that by overexpressing WEE1, cancer cells suppress IDH2 gene expression—revealing a novel epigenetic pathway wherein histone Tyr-phosphorylation regulates DNA methylation, promoting GBM and melanoma malignancy. Overall, pY37-H2B modification was studied at two important genetic loci (HIST1 and IDH2) and assessed its role in histone transcription and gene regulation.

A Novel Function of WEE1 as a Regulator of Global Histone Output

The precise execution of epigenetic signaling events, which includes both addition and removal of epigenetic marks in a temporally regulated manner, is paramount to preserving the chromatin landscape and consequently governs the fate of the cell. Inappropriate inhibition or activation of epigenetic signaling events profoundly alters the epigenome and is linked to cancer and developmental diseases. At the heart of the epigenome are the histones. In higher eukaryotes histone synthesis is a complex affair- to keep up with the massive demand of wrapping newly duplicated DNA into chromatin, cells have evolved multiple copies of histone genes, each encoding a fraction of the total histone protein (Marzluff, W. F. et al. (2012) Genomics, 80(5):487-498). Strikingly, at the end of S-phase, histone transcription plummets to allow cells to maintain proper histone-DNA stoichiometry prior to mitotic entry (Osley, M. A. (1991) Annu Rev Biochem, 60:827-861; Hereford, L. M. et al. (1981) Cell, 24(2):367-375; Hereford, L. et al. (1982) Cell, 30(1):305-310). The process by which higher eukaryotic cells achieve this precipitous drop in histone transcript levels has remained elusive. Unexpectedly, Applicants identified a previously unknown epigenetic activity of the WEE1 tyrosine kinase—it directly modulates the histone gene transcription by phosphorylating the core histone H2B at Y37 and recruiting a transcriptional repressor to these loci. Mammalian cells deficient in WEE1 function abrogated H2B Y37-phosphorylation with a concurrent increase in histone transcription. Importantly, S. cerevisiae mutants, swe1, lacking the homolog of human WEE1, or the H2BY40A mutants, too were defective in H2B Y40-phosphorylation (equivalent to H2BY37 in mammals) and did not terminate histone transcription at the end of S phase, suggesting that the epigenetic transcriptional suppressive activity mediated by WEE1 is evolutionarily conserved and is critical to maintain chromatin homeostasis (Mahajan, K. et al. (2012) Nat. Struct. Mol. Biol., 19(9):930-937; Mahajan, K. et al. (2013) Trends in Genetics: TIG, 29(7):394-402). While it has been well established that averting overproduction of histones is necessary for chromatin homeostasis, how is it accomplished is far from clear. Applicants have made the first attempt to obtain comprehensive understanding of the regulatory roles of the various players that congregate at the pY37-H2B epigenetic mark to regulate global chromatin transaction.

HIRA, a Novel pY37-H2B Epigenetic Reader Involved in Global Histone Transcription Suppression Epigenetic readers are chromatin architectural proteins that recognize specific marks on histones (or nucleotides) and can either induce chromatin compaction or prevent the binding of proteins involved in transcription. Applicants discovered a role for HIRA, as a novel pY37-H2B epigenetic reader; it suppressed transcription of multiple histone genes of the HIST1 cluster (Mahajan, K. et al. (2012) Nat. Struct. Mol. Biol., 19(9):930-937; Mahajan, K. et al. (2013) Trends in Genetics: TIG, 29(7):394-402). HIRA (HIR histone cell cycle regulation defective homolog A) has been identified as a component of the chromatin remodeling complex of HIRA/Asf1/UBN1, which by its association with HP1 spreads across silenced domains to enforce transcriptional silencing (Yamane, K. et al. (2011) Molecular Cell, 41(1):56-66; Canzio, D. et al. (2013) Nature, 496 (7445):377-381; Canzio, D. et al. (2011) Molecular Cell, 41(1):67-81). HIRA also acts as a histone chaperone by depositing the variant histone H3.3 in a replication-independent manner into the nucleosome (Rai, T. S., et al. (2011) Mol. Cell. Biol., 31(19):4107-4118). Interestingly, Applicants observed that pY37-H2B epigenetic mark acts as a beacon for the recruitment of HIRA (mammals) and HIR (yeast), leading to the suppression of global histone gene transcription in different eukaryotic systems (Mahajan, K. et al. (2012) Nat. Struct. Mol. Biol., 19(9):930-937). These data support the idea that the mechanism of transcriptional suppression by pY37-H2B/HIRA complex is evolutionarily conserved. Although this recent work has uncovered a novel epigenetic reader function of HIRA, how HIRA recognizes the pY37-H2B epigenetic marks to enforce transcriptional shutdown is not known. Applicants have undertaken detailed characterization of HIRA/pY37-H2B interaction, especially focusing on assessing the C-terminal region of HIRA as a potential epigenetic reader domain. Further, Applicants examined the effect on transcription of the HIST1 locus and IDH2 upon inhibition of pY37-H2B and HIRA reader domain interaction.

a Timely Removal of pY37-H2B Marks on Chromatin: CDC14 and EYA Family of Tyrosine Phosphatases as pY37-H2B Erasers Cell cycle analysis indicated that cells rapidly exit S phase once histone transcription is terminated and the pY37-H2B marks are quickly erased (Mahajan, K. et al. (2012) Nat. Struct. Mol. Biol., 19(9):930-937; Mahajan, K. et al. (2013) Trends in Genetics: TIG, 29(7):394-402). The temporal and transient nature of H2B Y37-phosphorylation suggests that cells may actively recruit a phosphatase to dephosphorylate pY37-H2B before the cells enter G2/M phase. Identification of a novel pY37-H2B-specific phosphatase would be highly desirable to interrogate its role in preserving the chromatin landscape. Because a pY37-H2B-specific phosphatase has not yet been identified, we performed substrate specificity assessment of all the tyrosine phosphatase family members which led us to determine that the members of the CDC14 tyrosine phosphatase family could be a potential pY37-H2B-specific phosphatase. This family consists of four members (CDC14A, B, KAP and PTP9Q22) which are evolutionarily conserved tyrosine phosphatases (Hartwell, L. H. et al. (1974) Science, 183(4120):46-51; Gray, C. H. et al. (2003) The EMBO Journal, 22(14):3524-3535). Of these the CDC14A, was recently found to interact with Swe1, a WEE1 homolog in S. cerevisiae (Breitkreutz, A. et al. (2010) Science, 328(5981):1043-1046). Taken together, these data suggest to an additional role for WEE1 as a dynamic recruiter of the cognate phosphatase, CDC14A, to accomplish de-phosphorylation of the pY37-H2B epigenetic marks.

Applicants' pursuit of understanding the transient nature of pY37-H2B marks unveiled another surprise—the pY37-H2B epigenetic marks were rapidly erased following DNA double-strand breaks (DSBs) in ATM dependent manner. ATM is known to recruit the eyes absent (EYA) family of tyrosine phosphatases to dephosphorylate the variant histone H2AX (Cook, P. J. et al. (2009) Nature, 458(7238):591-

596). These data suggest that EYA could be a second potential epigenetic eraser of the pY37-H2B epigenetic marks, but specifically in response to damage induced by genotoxic agents such as IR. Thus, at least two distinct phosphatases may catalyze the removal of the pY37-H2B marks depending on the status of chromatin; (i) CDC14, which erases these epigenetic marks at the end of DNA replication in late S-phase of cell cycle, and, (ii) EYA, which erases pY37-H2B epigenetic marks specifically in response to DSBs. We have assessed the activity of both of these tyrosine phosphatases in greater detail, as potential pY37-H2B epigenetic erasers.

Epigenetic Mechanisms Underlying IDH2 Transcriptional Down Regulation in GBMs

Glioblastomas or GBMs are not only the most common brain cancers, but also present with the dismal prognosis (Wen, P. Y. et al. (2008) N. Engl. J. Med., 359(5):492-507). A median survival is about 15 months and only 3-5% of GBM patients survive longer than 36 months. These account for ~13,000 deaths per year in U.S. alone (Wen, P. Y. et al. (2008) N. Engl. J. Med., 359(5):492-507). The molecular basis of GBM pathogenesis is unknown, which has made research into understanding the biology and the identification of therapeutic targets an area of intense research interest.

Isocitrate dehydrogenases, IDH1 and IDH2, catalyze the oxidative decarboxylation of isocitrate to a-ketoglutarate (a-KG), a crucial regulator of cell metabolism (Xu, W. et al. (2011) Cancer Cell, 19(1):17-30; Reitman, Z. J. et al. (2010) J. Natl. Cancer Inst., 102(13):932-941). About 60 dioxygenases expressed in mammalian cells utilize a-KG as an essential cofactor in the oxidation reaction, including the recently discovered TET family of 5-methylcytosine (5mC) hydroxylases that convert 5-mC to 5-hmC (Iyer, L. M. et al. (2009) Cell Cycle, 8(11):1698-1710; Loenarz, C. et al. (2008) Nat. Chem. Biol., 4(3):152-156; Tsukada, Y. et al. (2006) Nature, 439(7078):811-816; Tahiliani, M. et al. (2009) Science, 324(5929):930-935). Although the levels of 5-hmC are tissue independent, the highest levels have been reported in brain (Kriaucionis, S. et al. (2009) Science, 324(5929):929-930). In recent years, the loss of 5-hmC has been identified to be a recurrent epigenetic hallmark in GBMs and melanomas (Orr, B. A. et al. (2012) PLoS One, 7(7):e41036; Lian, C. G. et al. (2012) Cell, 150(6):1135-1146; Krell, D. et al. (2011) PloS One, 6(5):e19868). While down regulation of IDH2 has emerged to be a key event in the loss of 5-hmC in cancer cells, how IDH2 downregulation is specifically achieved is not clear.

Figure 45A:
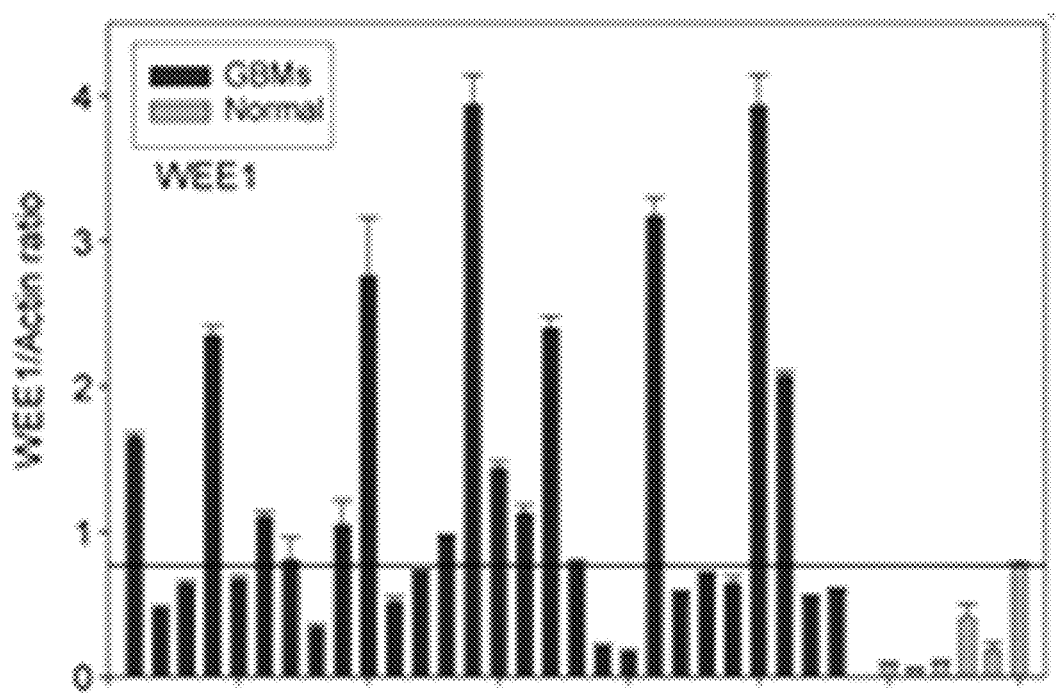
FIGS. 45A and 45B show upregulation of WEE1 and suppression of IDH2 expression in GBMs. qRT-PCR of normal brain and GBM tumor RNA (patient #1-27) in triplicates. Relative expression of WEE1 (FIG. 45A) and IDH2 (FIG. 45B) is shown.
Figure 45B:
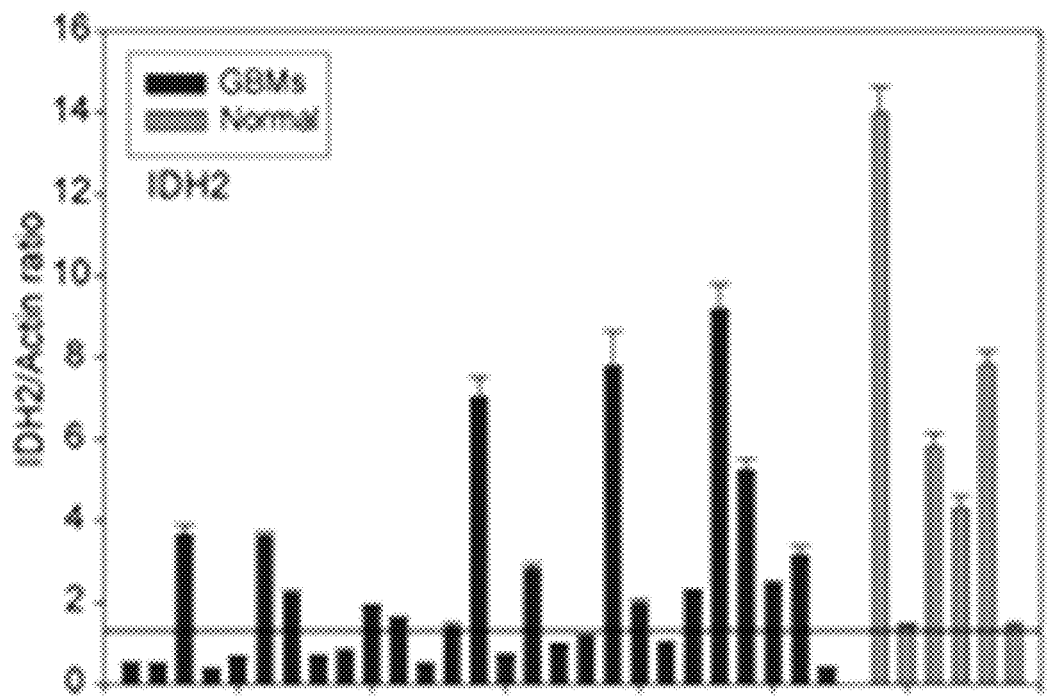
Figure 46A:
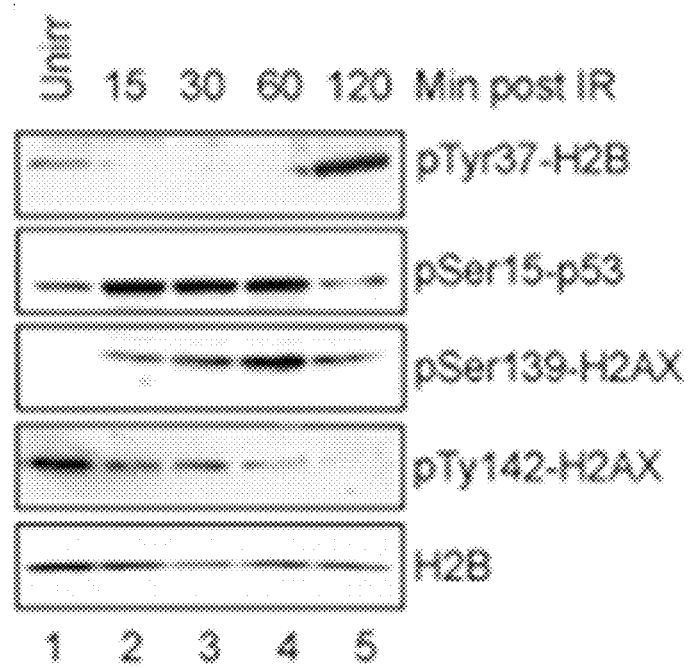
FIGS. 46A and 46B show that removal of pY37-H2B epigenetic marks following DNA DSBs.
Figure 46B:
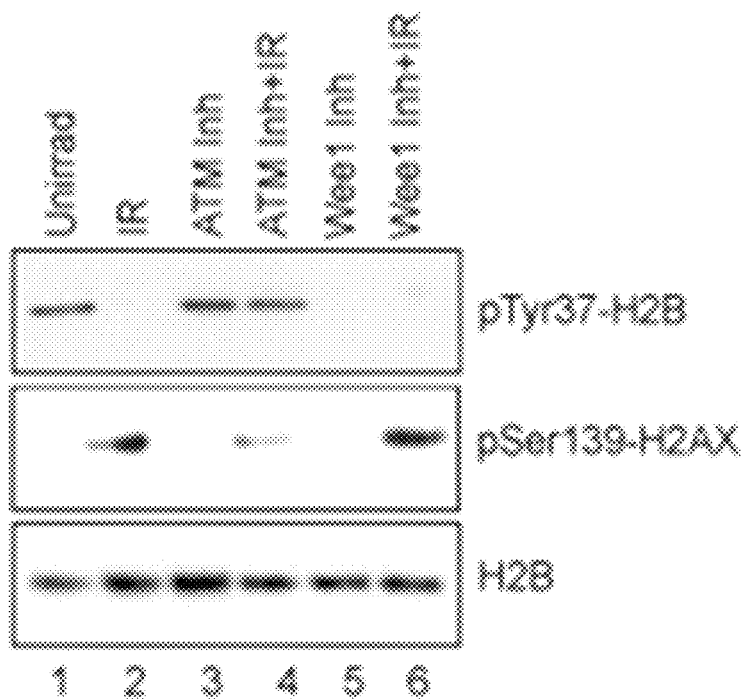
Figure 47:
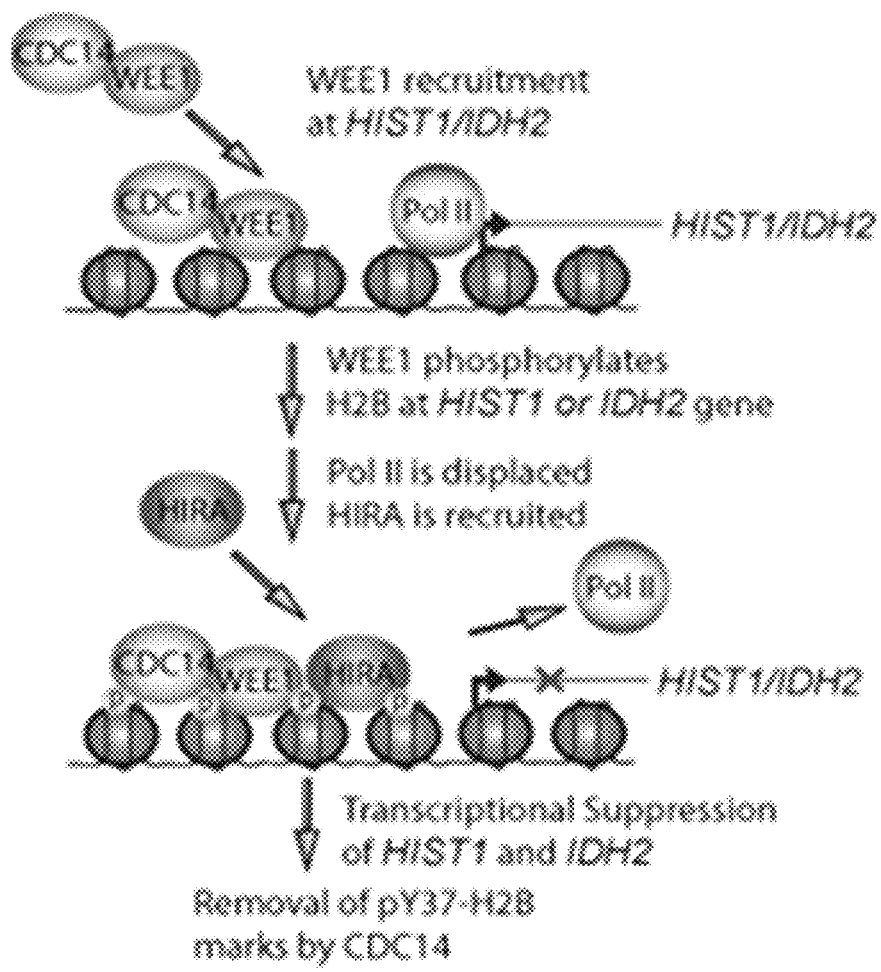
FIG. 47 shows proposed mechanism for HIST1 and IDH2 transcriptional suppression by WEE1 epigenetic activity.

A clue to IDH2 down regulation in GBMs emerged from Applicants' ChIP-Sequencing experiments. It revealed that WEE1 deposits pY37-H2B marks not only upstream of the HIST1 cluster but also within the IDH2 gene. It indicated, for the first time, that the epigenetic activity of WEE1 is not only crucial in regulating global histone synthesis, but may also have a role in regulating 'other' epigenetic modifications, such as DNA methylation. Without being bound by theory, it was reasoned that cancer cells could benefit enormously if they were to hijack WEE1/pY37-H2B epigenetic signaling to modify chromatin by altering methylation status. To address this supposition, the mRNA levels of WEE1 and IDH2 were examined in GBM tumors and observed that about 26% of GBM patients exhibit elevated WEE1 mRNA expression and significant down regulation of IDH2 transcription (FIG. 47). Conversely, inhibition of WEE1 by MK-1775 increased IDH2 transcript levels and restored 5-hmC levels (FIGS. 45 and 46). This is an important finding, as reversal of 5-hmC levels by WEE1 inhibitor (or any other inhibitor) has not been previously demonstrated.

MK-1775 (AZT-1775), a Novel Epigenetic Inhibitor

WEE1 tyrosine kinase plays a key role as a regulator of the G2/M checkpoint that precedes entry into mitosis. Hence after DNA damage, WEE1 inhibitor can be deployed to block phosphorylation of CDK1, thereby promoting inappropriate cell cycle progression, causing mitotic catastrophe. Based on this premise, MK-1775 combined with gemcitabine, cisplatin or carboplatin has entered phase I & II clinical trials (NCI Clinical Trial). However, this data uncovered an additional function of WEE1 kinase, an epigenetic modulator, overexpression of which in cancer cells could suppress global histone output as well as silence tumor suppressor, IDH2. Although, almost 13 clinical trials are active or approved for MK-1775, none take into account the WEE1 epigenetic function for selecting the patients for their potential response. In this study Applicants performed preclinical evaluation of MK-1775 as a novel epigenetic therapeutic agent. Specifically, this study has demonstrated that a quarter of GBM patients may exhibit robust activation of WEE1 epigenetic signaling nexus and suppression of both histone and IDH2 mRNA levels can be a companion diagnostic for screening of patients that are likely to respond to MK-1775, a desperate need for these patients.

Metastatic Melanomas Display Significant Decrease in IDH2 mRNA Expression

Not only is WEE1 overexpressed in melanomas, MK-1775, a potent WEE1-specific inhibitor selectively induces apoptosis in WEE1 expressing cancer cell lines (Hirai, H., et al. (2009) Mol. Cancer Ther., 8(11):2992-3000; Sarcar, B. et al. (2011) Mol. Cancer Ther., 10(12):2405-2414; De Witt Hamer, P. C. et al. (2011) Clin. Cancer Res., 17(13):4200-4207), suggesting that some of the melanomas may be addicted to the WEE1 signaling pathway for survival. Based on the prior finding that WEE1 epigenetically regulates the expression of chromatin modifying gene IDH2, Applicants envisaged that alterations in WEE1 regulatory control could significantly disrupt the epigenetic landscape of melanomas, to promote malignancy. To interrogate this hypothesis further, Applicants obtained 15 primary melanomas and 3 normal skin samples (total 18 samples) under SRC/IRB approved protocol, MCC#15375, IRB Study #106509 (PI: Sarnaik, Co-I: Mahajan). All the tumors were microdissected and pathologist validated each of the microdissected tissue samples prior to its usage. As a first step, total RNA was prepared followed by qRT-PCR using IDH2 and actin specific primers. Although, there was some inter individual variability, a significant decrease in IDH2 mRNA levels was apparent in melanomas as compared to normal skin samples.

Statistical Analysis:

Relative expression of IDH2 mRNAs was determined based on its ratio with actin. The log-transformation was taken so that the data were normally distributed. The differences in relative IDH2 mRNA levels between melanoma and normal human skin were statistically significant (p=0.048). The p-values are two-sided and computed by the two-sample t-test. To identify patients that exhibit significant downregulation of IDH2, the threshold for each variable was selected to maximize the sensitivity (ratio of positives to melanoma) when the specificity (ratio of negatives to normal samples) is set to 1. These indicated that the melanoma patients whose IDH2/Actin ratios are <1.67, are likely to have active/elevated WEE1/pY37-H2B signaling. There were 10 such patients (patient #2, 4, 5, 8-14) that fit in this category, indicating that about 70% (10 of 14) of the melanoma patients exhibit elevated WEE1/pY37-H2B signaling (90% CI: 0.128-0.432). In contrast, none of the normal skin samples exhibited <1.67 ratios for IDH2/Actin.

Deposition of pY37-H2B Epigenetic Mark by WEE1 Suppresses IDH2 and Histone Transcription.

To investigate whether WEE1/pY37-H2B signaling plays a direct role in regulating IDH2 gene transcription, three WEE1 expressing cancer cell lines, U87 (GBM), LNCaP (prostate) and WM1366 (melanoma) were treated (1 uM, 24 hours), or untreated, with WEE1-specific small molecule inhibitor MK-1775. Total RNA was isolated followed by qRT-PCR with IDH2 and actin specific primers. As control, U118 cell line was used which has low levels of WEE1 (unpublished data). A significant increase in transcript levels of the IDH2 gene was observed in WEE1 expressing U87, LNCaP & WM1366 cells upon treatment with MK-1775 (FIG. 42A-42C), in contrast, IDH2 mRNA was not increased in U118 cell line (FIG. 42D).

Figure 42:
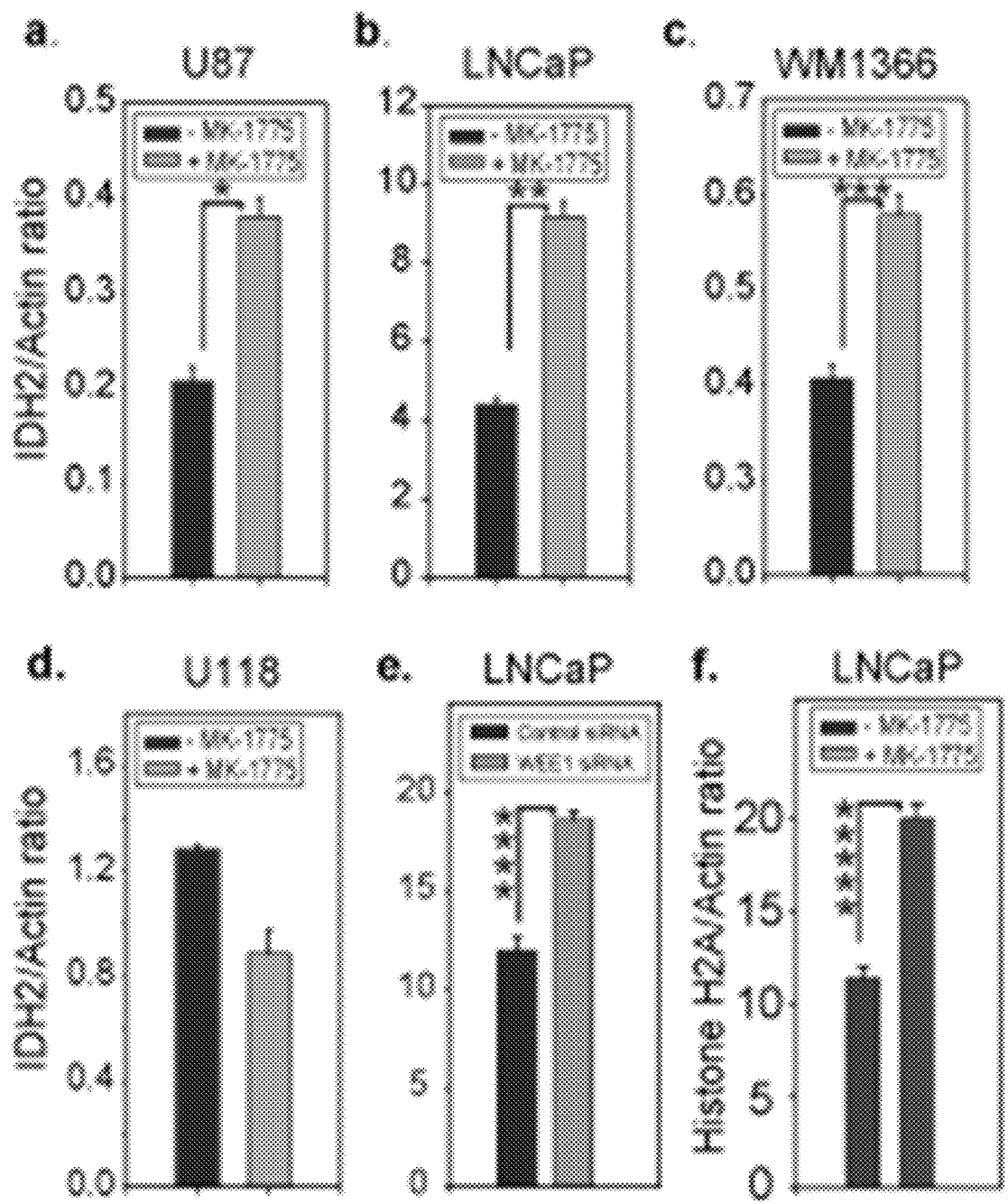
FIG. 42a-42f show that inhibition of WEE1 increases IDH2 gene transcription.

To examine if MK-1775 mediated IDH2 downregulation is not due to its 'off site effect', LNCaP cells were transfected with WEE1 or control siRNA, which indicates that WEE1 loss by siRNA too resulted in increased IDH2 levels (FIG. 42E).

Applicants also validated WEE1's ability to suppress histone transcription in LNCaP cells (FIG. 42F). Taken collectively, these data indicate that epigenetic writing by WEE1 has a repressive effect on transcription of the IDH2 and histones and it can be reversed by MK-1775.

Reversal of the Loss of the Epigenetic Mark 5-hmC by WEE1 Inhibitor

Figure 43:
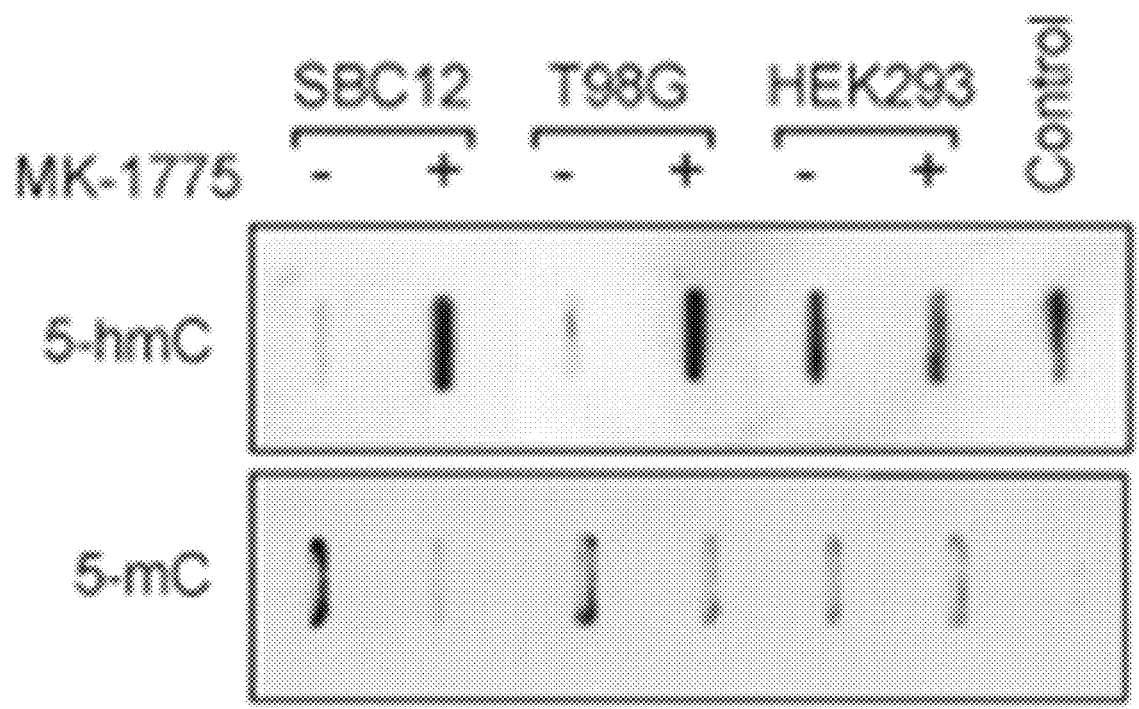
FIG. 43 shows that inhibition of WEE1 kinase increases 5-hmC levels. SBC12, T98G and HEK293 cells were treated with WEE1 inhibitor, MK1775 (0.6 μM, 24 hr). Blots were incubated with 5-hmC and 5-mC antibodies.

To determine whether WEE1 mediated IDH2 transcriptional suppression impacts 5-hmC levels in cells, a melanoma derived cell line SBC12 was treated with the WEE1 inhibitor, MK-1775. Genomic DNA was isolated, blotted by slot blot, followed by immunoblotting with 5-hmC and 5-mC antibodies. A GBM-derived T98G cells was used as positive control as it is known to possess low 5-hmC levels (Lian, C. G. et al. (2012) Cell, 150(6):1135-1146). Both of these cell lines exhibited significant upregulation in 5-hmC levels upon WEE1 inhibitor treatment (FIG. 43). HEK293 cells were used as control as they do not exhibit endogenous WEE1 overexpression (unpublished data). As expected, non cancerous HEK293 cell, exhibited high levels of 5-hmC levels which remained unchanged by WEE1 inhibition. 5-hmC containing plasmid DNA (Zymo research) was used as positive control. Immunoblotting with 5-mC antibodies revealed concomitant decrease (FIG. 43), which is consistent with the report of Kriaucionis and Heintz who demonstrated that an increase in the amount of 5-hmC is proportional to the decrease in 5-mC (Kriaucionis, S. et al. (2009) Science, 324(5929):929-930).

WEE1 Marks the IDH2 Locus by H2B Tyr37-Phosphorylation

Figure 44:
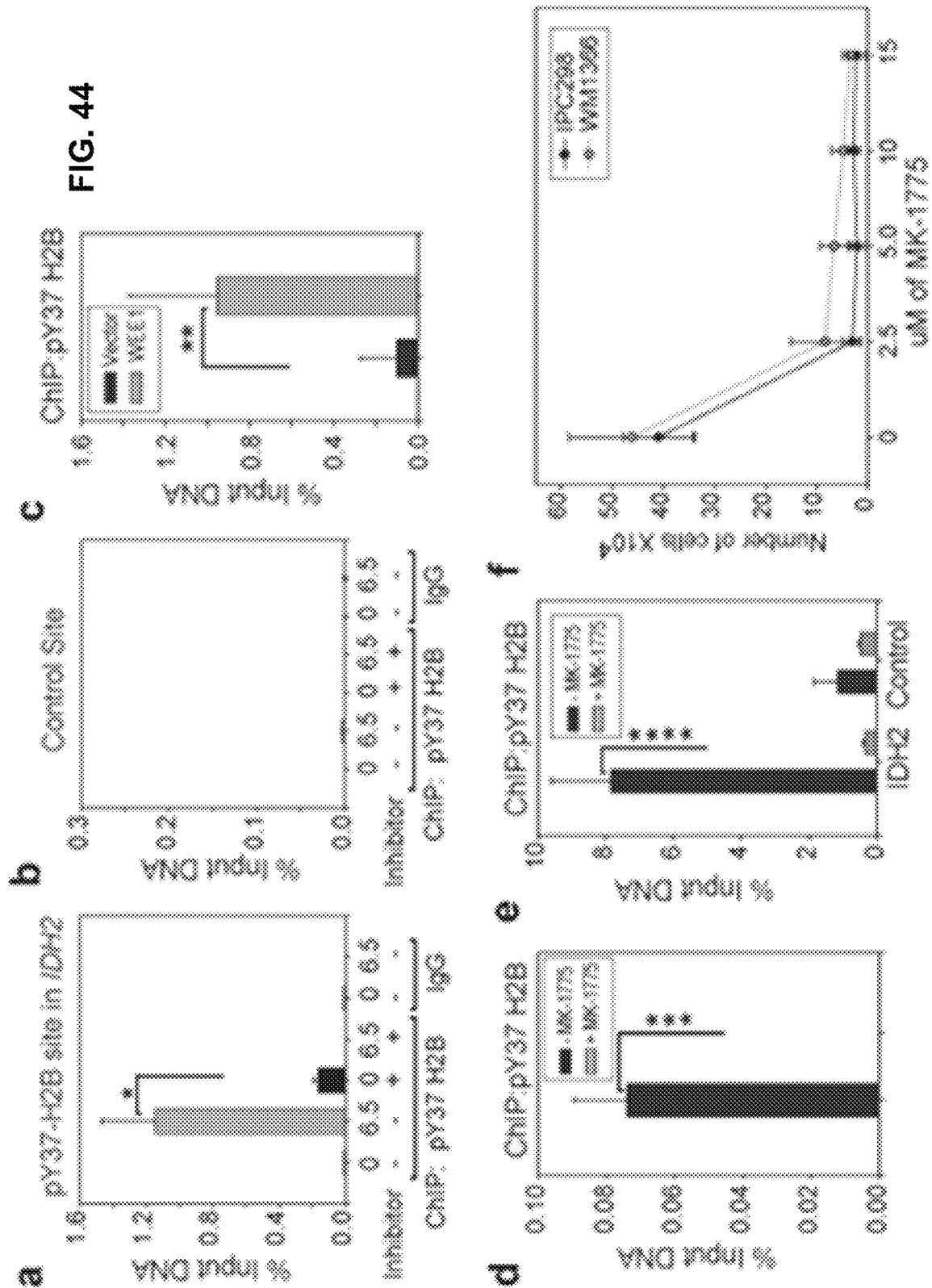
FIG. 44a-44f show H2B Tyr37-phosphorylation marks are deposited within IDH2. WEE1 epigenetic footprint (pY37-H2B) is observed in the body of the (FIG. 44a) IDH2 gene in but not at (FIG. 44b) the control site in (FIG. 44c) HEK293 overexpressing WEE1 but not vector alone and (FIG. 44d) In the GBM derived cell line U87, but not in cells treated with the WEE1 specific inhibitor MK-1775 erased pY88-H2B marks. *p=0.001; p=0.028. *p=0.002.

ChIP-sequencing also revealed the presence of H2B Y37-phosphorylation in the IDH2 coding region (87,259,086-87,259,752) which was confirmed by directed ChIP-PCR in synchronized MEFs (FIG. 44A). Treatment of cells with the WEE1 specific inhibitor, MK-1775, abolished the deposition of pY37-H2B epigenetic marks. As a control, Applicants used primers corresponding to the 'Gene desert' on chromosome 6, where pY37-H2B marks were not detected (control site, FIG. 44B). Based on the location, Applicants identified the corresponding pY37-H2B-binding site in human cells (15,241-15,400 nucleotide position). To validate the presence of pY37-H2B marks within the human IDH2 gene locus, sheared chromatin from HEK293 cells transfected with WEE1 kinase (or vector as a control) were immunoprecipitated using the pY37-H2B antibody followed by qPCR using primers corresponding to pY37-H2B-binding site in the IDH2 gene. WEE1 overexpression resulted in significant increase in pY37-H2B deposition in the IDH2 gene (FIG. 44C).

To validate the role of WEE1 in IDH2 marking, chromatin from GBM derived cell line U87 was immunoprecipitated using the pY37-H2B antibody followed by qPCR. It revealed that pY37-H2B marks within IDH2 were completely erased following treatment with the WEE1 inhibitor, MK-1775 (FIG. 44D). Similar data was obtained with another human GBM derived cell lines T98G (FIG. 44E).

To identify patients that exhibit significant elevation in WEE1/IDH2 signature and thus are potentially responders to WEE1-specific inhibitors such as MK-1775, the threshold for each variable was selected to maximize the sensitivity (ratio of positives to GBMs) when the specificity (ratio of negatives to normal samples) is set to 1. GBM patients whose WEE1/Actin and IDH2/Actin ratios are >0.774 and <1.27, respectively, are likely to have highly active/elevated WEE1/IDH2 signaling. There were 7 such patients (patient #1, 4, 9, 15, 17, 18 and 21) that fit in this category, indicating that about 26% (7 out of 27) of the GBM patients exhibit elevated WEE1/IDH2 signaling (90% CI: 0.128-0.432). In contrast, none of the normal brain samples exhibited >0.774 and <1.27 ratios for WEE1/Actin and IDH2/Actin. These results show that elevated WEE1 expression may be an important contributor in the loss of 5-hmC, reported in GBMs, via suppressing IDH2 expression.

TABLE 6

Descriptive Statistics- IDH2 and WEE1 expression profiles

| Variable | Sample | N | Mean | SD | Med. | Min. | Max |
|---|---|---|---|---|---|---|---|
| IDH2/Actin | GBMs | 27 | 2.4 | 2.39 | 1.61 | 0.37 | 9.3 |
| | Normals | 6 | 5.77 | 4.73 | 4.99 | 1.4 | 13.99 |
| WEE1/Actin | GBMs | 27 | 1.3 | 1.1 | 0.79 | 0.17 | 3.96 |
| | Normals | 6 | 0.28 | 0.27 | 0.17 | 0.06 | 0.76 |

Legend: Med. = median; Min. = minimum; Max = maximum.

the Epigenetic Erasers of pY37-H2B Marks

The quest to decode the transient nature of pY37-H2B epigenetic marks revealed that they are rapidly dephosphorylated upon the introduction of double strand breaks (DSBs) by ionizing radiation or IR (FIG. 47A). Recently, de-phosphorylation H2AX at pY142 by EYA tyrosine phosphatase has been reported to facilitate survival after DNA DSB repair (Cook, P. J. et al. (2009) Nature, 458(7238): 591-596). Strikingly, in contrast to the H2AX Y142-phosphorylation, the H2B Y37-phosphorylation is restored within 2 hours, a time which coincides with repair in most cell lines (FIG. 46A, lane 5).

To determine whether pY37-H2B de-phosphorylation is regulated by ATM recruited to the sites of DSBs by the MRN complex, Applicants treated the cells with the ATM inhibitor Ku55393. Addition of the ATM inhibitor prevented IR-induced de-phosphorylation of pY37-H2B (FIG. 46B, lane 4). Collectively, these data opened a possibility that the ATM kinase, one of the first responders to DSB sites, is likely to recruit a pY37-H2B phosphatase following DNA damage. Interestingly, EYA1 and 3 tyrosine phosphatase have been shown to be specifically recruited by ATM in response to IR (Cook, P. J. et al. (2009) Nature, 458(7238):591-596). EYA in turn interacted with H2AX executing a damage-signal-dependent dephosphorylation of Tyr142, that is constitutively phosphorylated in the absence of DNA damage (Cook, P. J. et al. (2009) Nature, 458(7238):591-596).

Based on these evidences, and without being bound by theory, Applicants reasoned that ATM could recruit the EYA phosphatase to erase the pY37-H2B marks. Overall, these data indicates that EYA is a potential epigenetic eraser of the pY37-H2B epigenetic marks in response to damage induced by genotoxic agents such as IR.

In addition, this data indicated that a second tyrosine phosphatase, CDC14, may be operational to erase pY37-H2B marks, specifically in late S-phase of cell cycle. This data indicates that WEE1-interacting CDC14 phosphatase erase pY37-H2B epigenetic marks prior to entry in G2/M phase.

Summary:

While signaling mechanisms and cytosolic effectors of most tyrosine kinases have been well-studied, the chromatin tyrosine phosphorylation field is still in its infancy. Applicants identified a previously undocumented histone phosphorylation event, pY37-H2B. But, how this epigenetic mark exerts its regulatory function was not understood. Applicants has delineated for the first time the precise mechanistic details of pY37-H2B recognition by a novel epigenetic reader, H IRA.

Every cell duplicates its chromatin precisely to prevent mitotic catastrophe, however, the players orchestrating chromatin replication with cell cycle progression are not well understood. Applicants uncovered the mechanistic details of pY37-H2B deposition at the end of S phase to co-ordinate termination of chromatin synthesis before mitosis.

This data indicates that just as the pY37-H2B deposition is precisely regulated, its removal too is strictly controlled.

Applicants discovered that the WEE1/pY37-H2B signaling epigenetically suppresses IDH2 transcription, preventing the formation of 5-hmC. Strikingly, WEE1 inhibition by MK-1775 or AZT-1775 leads to increased 5-hmC levels. To the best of Applicants' knowledge, this is the first report of a reversal of 'loss of 5-hmC' in cancer cells by WEE1 inhibitor.

Applicants have uncovered a novel epigenetic signaling axis, WEE1/pY37-H2B/IDH2/5-hmC that is operational in a subset of GBM patients (~26% of GBM patients). Significantly, it also revealed a telltale signature for WEE1 inhibitor sensitivity. However, screening of GBM patients for the activation of WEE1 epigenetic signaling to facilitate personalized treatment with WEE1 inhibitor is an unmet clinical need. The results from this study could lead to the development of first of its kind 'companion diagnostic test' for WEE1 inhibitor, MK-1775 (AstraZeneca), for GBM patients. Significantly, this test can also be used for melanoma patients, which exhibit significant upregulation of WEE1 activity.

While signaling mechanisms and cytosolic effectors of most tyrosine kinases have been well-studied, the chromatin tyrosine phosphorylation field is still in its infancy. Applicants have identified a previously undocumented histone phosphorylation event, pY37-H2B orchestrated by WEE1 tyrosine kinase (Mahajan, K. et al. (2012) Nat. Struct. Mol. Biol., 19(9):930-937; Mahajan, K. et al. (2013) Trends Genet., 29(7):394-402). Recent reports demonstrate recurrent aberrant expression of WEE1 in highly aggressive tumors such as melanomas and GBMs (Mir, S. E. et al. (2010) Cancer Cell, 18(3):244-257; Wuchty, S. et al. (2011) PloS One, 6(2):e14681; Magnussen, G. I. et al. (2012) PloS One, 7(6):e38254; Aarts, M. et al. (2012) Cancer Discov., 2(6):524-539; lorns, E. et al. (2009) PloS One, 4(4):e5120), highlighting its underappreciated role in cancer pathogenesis. Applicants have examined the ability of WEE1 to alter the epigenetic landscape. However, the molecular mechanism by which the nuclear WEE1/pY37-H2B epigenetic signaling alters the cancer epigenome to favor proliferation remains unexplored. This data established operational status of the WEE1/pY37-H2B/IDH2 signaling nexus in melanoma, GBMs and prostate cancer.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

The invention claimed is:

1. A personalized method for treating a subject with cancer, comprising
   (a) detecting overexpression of a WEE1 protein in a sample from the subject;
   (b) detecting underexpression of IDH2 protein in the sample; and
   (c) treating the subject with a composition comprising MK-1775.

2. The method of claim 1, wherein expression level of the WEE1 protein is determined by detecting the amount of mRNA encoding WEE1 protein in the sample.

3. The method of claim 1, wherein expression level of the WEE1 protein is determined using an antibody that specifically recognizes the WEE1 protein.

4. The method of claim 1, wherein expression level of the IDH2 protein is determined by detecting the amount of mRNA encoding IDH2 protein in the sample.

5. The method of claim 1, wherein expression level of the IDH2 protein is determined using an antibody that specifically recognizes the IDH2 protein.

6. The method of claim 1, wherein the cancer is a melanoma.

7. The method of claim 1, wherein the cancer is a glioblastoma multiforme (GBM).

8. The method of claim 1, wherein the cancer is a brain cancer or prostate cancer.

* * * * *

SEQUENCE LISTING

<160> NUMBER OF SEQ ID NOS: 81

<210> SEQ ID NO 1
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (3)..(3)
<223> OTHER INFORMATION: Phospho-Tyr

<400> SEQUENCE: 1

Glu Ser Tyr Ser Val Tyr Val Tyr Lys
1               5

<210> SEQ ID NO 2
<211> LENGTH: 16
<212> TYPE: PRT
<213> ORGANISM: Homo sapiens

<400> SEQUENCE: 2

Lys Arg Ser Arg Lys Glu Ser Tyr Ser Val Tyr Val Tyr Lys Val Leu
1               5                   10                  15

<210> SEQ ID NO 3
<211> LENGTH: 16
<212> TYPE: PRT
<213> ORGANISM: Bos taurus

<400> SEQUENCE: 3

Lys Arg Ser Arg Lys Glu Ser Tyr Ser Ile Tyr Val Tyr Lys Val Leu
1               5                   10                  15

<210> SEQ ID NO 4
<211> LENGTH: 16
<212> TYPE: PRT
<213> ORGANISM: Xenopus laevis

<400> SEQUENCE: 4

Arg Lys Ser Arg Lys Glu Ser Tyr Ala Ile Tyr Val Tyr Lys Val Leu
1               5                   10                  15

<210> SEQ ID NO 5
<211> LENGTH: 16
<212> TYPE: PRT
<213> ORGANISM: Danio rerio

<400> SEQUENCE: 5

Lys Arg Thr Arg Lys Glu Ser Tyr Ala Ile Tyr Val Tyr Lys Val Leu
1               5                   10                  15

<210> SEQ ID NO 6
<211> LENGTH: 16
<212> TYPE: PRT
<213> ORGANISM: Aedes aegypti

<400> SEQUENCE: 6

Lys Gln Arg Arg Lys Glu Ser Tyr Ala Ile Tyr Ile Tyr Lys Val Leu
1               5                   10                  15

<210> SEQ ID NO 7
<211> LENGTH: 16
<212> TYPE: PRT
<213> ORGANISM: Drosophila melanogaster

<400> SEQUENCE: 7
```

```
Lys Arg Lys Arg Lys Glu Ser Tyr Ala Ile Tyr Ile Tyr Lys Val Leu
1               5                   10                  15

<210> SEQ ID NO 8
<211> LENGTH: 16
<212> TYPE: PRT
<213> ORGANISM: Bombyx mori

<400> SEQUENCE: 8

Lys His Lys Arg Lys Glu Ser Tyr Ala Ile Tyr Ile Tyr Lys Val Leu
1               5                   10                  15

<210> SEQ ID NO 9
<211> LENGTH: 16
<212> TYPE: PRT
<213> ORGANISM: Caenorhabditis elegans

<400> SEQUENCE: 9

Lys His Ala Arg Lys Glu Ser Tyr Ser Val Tyr Ile Tyr Arg Val Leu
1               5                   10                  15

<210> SEQ ID NO 10
<211> LENGTH: 16
<212> TYPE: PRT
<213> ORGANISM: Saccharomyces cerevisiae

<400> SEQUENCE: 10

Ser Lys Val Arg Lys Glu Thr Tyr Ser Ser Tyr Ile Tyr Lys Val Leu
1               5                   10                  15

<210> SEQ ID NO 11
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: source
<223> OTHER INFORMATION: /note="N-term acetylated"
<220> FEATURE:
<221> NAME/KEY: MOD_RES
<222> LOCATION: (8)..(8)
<223> OTHER INFORMATION: Phospho-Tyr
<220> FEATURE:
<221> NAME/KEY: MOD_RES
<222> LOCATION: (17)..(17)
<223> OTHER INFORMATION: Ahx
<220> FEATURE:
<221> NAME/KEY: source
<223> OTHER INFORMATION: /note="C-term amidated"

<400> SEQUENCE: 11

Lys Arg Ser Arg Lys Glu Ser Tyr Ser Val Tyr Val Tyr Lys Val Leu
1               5                   10                  15

Xaa Cys

<210> SEQ ID NO 12
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
```

```
<221> NAME/KEY: source
<223> OTHER INFORMATION: /note="N-term acetylated"
<220> FEATURE:
<221> NAME/KEY: MOD_RES
<222> LOCATION: (17)..(17)
<223> OTHER INFORMATION: Ahx
<220> FEATURE:
<221> NAME/KEY: source
<223> OTHER INFORMATION: /note="C-term amidated"

<400> SEQUENCE: 12

Lys Arg Ser Arg Lys Glu Ser Tyr Ser Val Tyr Val Tyr Lys Val Leu
1               5                   10                  15

Xaa Cys

<210> SEQ ID NO 13
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 13
atcccctcta ttaatcacat ggaacctgat                                    30

<210> SEQ ID NO 14
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 14
cactggcaaa agagcttctt gtacataaag                                    30

<210> SEQ ID NO 15
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 15
caaagccagg acttgaccct atgggacaca                                    30

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 16
tagtgttaga aagagttgag catcctatcc                                    30

<210> SEQ ID NO 17
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 17
ctgggtgact ttctttaaaa gagcactctt                                          30

<210> SEQ ID NO 18
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 18
gcaacgtaaa aacagaattc taggccttta                                          30

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 19
cattgctgac aggatgcaga agg                                                 23

<210> SEQ ID NO 20
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 20
tgctggaagg tggacagtga gg                                                  22

<210> SEQ ID NO 21
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 21
gcgacaacaa gaagacgcgc at                                                  22

<210> SEQ ID NO 22
<211> LENGTH: 21
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic
      primer"

<400> SEQUENCE: 22
ctggatgttg ggcaggacgc c                                        21

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 23
aagaaggacg gcaagaagcg ca                                       22

<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 24
cgctcgaaga tgtcgttcac ga                                       22

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 25
ctgatccgca agctgccgtt c                                        21

<210> SEQ ID NO 26
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 26
gttggtgtcc tcaaacagac cc                                       22

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

```
<400> SEQUENCE: 27
gaaggatggc aagaagcgca ag                                              22

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 28
cgctcgaaga tgtcgttcac ga                                              22

<210> SEQ ID NO 29
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 29
aacatccagg gcatcaccaa gc                                              22

<210> SEQ ID NO 30
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 30
gttctccagg aacaccttca gc                                              22

<210> SEQ ID NO 31
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 31
aagaaggacg gcaagaagcg ca                                              22

<210> SEQ ID NO 32
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 32
cgctcgaaga tgtcgttcac ga                                              22
```

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic
primer"

<400> SEQUENCE: 33
gaaaagatct ggcatcatac cttc                                    24

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic
primer"

<400> SEQUENCE: 34
aaaacggctt ggatggaaac                                         20

<210> SEQ ID NO 35
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic
primer"

<400> SEQUENCE: 35
ggtaagaaga gaagcaaggc tagaa                                   25

<210> SEQ ID NO 36
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic
primer"

<400> SEQUENCE: 36
gacttcttgt tatacgcagc ca                                      22

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic
primer"

<400> SEQUENCE: 37
tgtcttggaa tatttggccg                                         20

<210> SEQ ID NO 38
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 38
tggatgtttg gcaaaacacc                                                  20

<210> SEQ ID NO 39
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 39
gtcgatggta agaagagatc taagg                                            25

<210> SEQ ID NO 40
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 40
gtggatttct tgttataagc ggc                                              23

<210> SEQ ID NO 41
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 41
gctgtcttag aatatttggc tgc                                              23

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 42
ggcaacaagt tttggtgaat g                                                21

<210> SEQ ID NO 43
<211> LENGTH: 25
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic
      primer"

<400> SEQUENCE: 43
gctttgagag aaatcagaag attcc                                            25

<210> SEQ ID NO 44
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 44
gcagccaagt tggtatcttc aa                                               22

<210> SEQ ID NO 45
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 45
ctgttgcctt gagagaaatt agaag                                            25

<210> SEQ ID NO 46
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 46
gcagccagat tagtgtcttc aaac                                             24

<210> SEQ ID NO 47
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 47
taaaggtcta ggaaaaggtg gtgc                                             24

<210> SEQ ID NO 48
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"
```

-continued

```
<400> SEQUENCE: 48
taacagagtc cctgatgacg gatt                                          24

<210> SEQ ID NO 49
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 49

Asp Gly Lys Lys Arg Lys Arg Ser Arg Lys Glu Ser Tyr Ser Val Tyr
1               5                   10                  15

Val Tyr Lys Val Leu Lys Gln Val His
            20                  25

<210> SEQ ID NO 50
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (13)..(13)
<223> OTHER INFORMATION: Phospho-Tyr

<400> SEQUENCE: 50

Asp Gly Lys Lys Arg Lys Arg Ser Arg Lys Glu Ser Tyr Ser Val Tyr
1               5                   10                  15

Val Tyr Lys Val Leu Lys Gln Val His
            20                  25

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 51

Lys Glu Ser Tyr Ser Val Tyr Val Tyr Lys Val
1               5                   10

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 52

Arg Lys Glu Ser Tyr Ser Val Tyr Val Tyr Lys Val
1               5                   10
```

```
<210> SEQ ID NO 53
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 53

Arg Lys Glu Ser Tyr Ser Val Tyr Val Tyr Lys Val
1               5                   10

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (4)..(4)
<223> OTHER INFORMATION: Phospho-Tyr

<400> SEQUENCE: 54

Lys Glu Ser Tyr Ser Val Tyr Val Tyr Lys Val
1               5                   10

<210> SEQ ID NO 55
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      polypeptide"
<220> FEATURE:
<221> NAME/KEY: misc_feature
<222> LOCATION: (16)..(16)
<223> OTHER INFORMATION: May be phosphorylated

<400> SEQUENCE: 55

Phe Gln Ser Ser Ala Val Met Ala Leu Gln Glu Ala Cys Glu Ala Tyr
1               5                   10                  15

Leu Val Gly Leu Phe Glu Asp Thr Asn Leu Cys Ala Ile His Ala Lys
                20                  25                  30

<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: misc_feature
<222> LOCATION: (6)..(6)
<223> OTHER INFORMATION: May be phosphorylated

<400> SEQUENCE: 56

Ile Ser Gly Leu Ile Tyr Glu Glu Thr Arg
1               5                   10
```

```
<210> SEQ ID NO 57
<211> LENGTH: 16
<212> TYPE: PRT
<213> ORGANISM: Homo sapiens

<400> SEQUENCE: 57

Lys Arg Ile Ser Gly Leu Ile Tyr Glu Glu Thr Arg Gly Val Leu Lys
1               5                   10                  15

<210> SEQ ID NO 58
<211> LENGTH: 16
<212> TYPE: PRT
<213> ORGANISM: Saccharomyces cerevisiae

<400> SEQUENCE: 58

Lys Arg Ile Ser Gly Leu Ile Tyr Glu Glu Val Arg Ala Val Leu Lys
1               5                   10                  15

<210> SEQ ID NO 59
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 59

Ser Arg Lys Glu Ser Tyr Ser Val Tyr Val Tyr Lys
1               5                   10

<210> SEQ ID NO 60
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (6)..(6)
<223> OTHER INFORMATION: Phospho-Tyr

<400> SEQUENCE: 60

Ser Arg Lys Glu Ser Tyr Ser Val Tyr Val Tyr Lys
1               5                   10

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 61

Ser Arg Lys Glu Ser Phe Ser Val Tyr Val Tyr Lys
1               5                   10

<210> SEQ ID NO 62
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic
      peptide"

<400> SEQUENCE: 62

Lys Arg Ser Arg Lys Glu Ser Tyr Ser Val Tyr Val Tyr Lys Val Leu
1               5                   10                  15

<210> SEQ ID NO 63
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (8)..(8)
<223> OTHER INFORMATION: Phospho-Tyr

<400> SEQUENCE: 63

Lys Arg Ser Arg Lys Glu Ser Tyr Ser Val Tyr Val Tyr Lys Val Leu
1               5                   10                  15

<210> SEQ ID NO 64
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 64

Thr Val Thr Ala Met Asp Val Val Tyr Ala Leu Lys Arg Gln Gly Arg
1               5                   10                  15

Thr

<210> SEQ ID NO 65
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (9)..(9)
<223> OTHER INFORMATION: Phospho-Tyr

<400> SEQUENCE: 65

Thr Val Thr Ala Met Asp Val Val Tyr Ala Leu Lys Arg Gln Gly Arg
1               5                   10                  15

Thr

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
``` peptide"

<400> SEQUENCE: 66

Lys Arg Ile Ser Gly Leu Ile Tyr Glu Glu Thr Arg Gly Val Leu
1               5                   10                  15

<210> SEQ ID NO 67
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (8)..(8)
<223> OTHER INFORMATION: Phospho-Tyr

<400> SEQUENCE: 67

Lys Arg Ile Ser Gly Leu Ile Tyr Glu Glu Thr Arg Gly Val Leu
1               5                   10                  15

<210> SEQ ID NO 68
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 68

Ala Leu Gln Glu Ala Cys Glu Ala Tyr Leu Val Gly Leu Phe Glu Asp
1               5                   10                  15

<210> SEQ ID NO 69
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: MOD_RES
<222> LOCATION: (9)..(9)
<223> OTHER INFORMATION: Phospho-Tyr

<400> SEQUENCE: 69

Ala Leu Gln Glu Ala Cys Glu Ala Tyr Leu Val Gly Leu Phe Glu Asp
1               5                   10                  15

<210> SEQ ID NO 70
<211> LENGTH: 16
<212> TYPE: PRT
<213> ORGANISM: Mus musculus

<400> SEQUENCE: 70

Lys Arg Ser Arg Lys Glu Ser Tyr Ser Ile Tyr Val Tyr Lys Val Leu
1               5                   10                  15

<210> SEQ ID NO 71
<211> LENGTH: 16
<212> TYPE: PRT
<213> ORGANISM: Rattus norvegicus

<400> SEQUENCE: 71

Lys Arg Ser Arg Lys Glu Ser Tyr Ser Val Tyr Val Tyr Lys Val Leu
1               5                   10                  15

<210> SEQ ID NO 72
<211> LENGTH: 16
<212> TYPE: PRT
<213> ORGANISM: Bos taurus

<400> SEQUENCE: 72

Lys Arg Ile Ser Gly Leu Ile Tyr Glu Glu Thr Arg Gly Val Leu Lys
1               5                   10                  15

<210> SEQ ID NO 73
<211> LENGTH: 16
<212> TYPE: PRT
<213> ORGANISM: Mus musculus

<400> SEQUENCE: 73

Lys Arg Ile Ser Gly Leu Ile Tyr Glu Glu Thr Arg Gly Val Leu Lys
1               5                   10                  15

<210> SEQ ID NO 74
<211> LENGTH: 16
<212> TYPE: PRT
<213> ORGANISM: Rattus norvegicus

<400> SEQUENCE: 74

Lys Arg Ile Ser Gly Leu Ile Tyr Glu Glu Thr Arg Gly Val Leu Lys
1               5                   10                  15

<210> SEQ ID NO 75
<211> LENGTH: 16
<212> TYPE: PRT
<213> ORGANISM: Xenopus laevis

<400> SEQUENCE: 75

Lys Arg Ile Ser Gly Leu Ile Tyr Glu Glu Thr Arg Gly Val Leu Lys
1               5                   10                  15

<210> SEQ ID NO 76
<211> LENGTH: 16
<212> TYPE: PRT
<213> ORGANISM: Danio rerio

<400> SEQUENCE: 76

Lys Arg Ile Ser Gly Leu Ile Tyr Glu Glu Thr Arg Gly Val Leu Lys
1               5                   10                  15

<210> SEQ ID NO 77
<211> LENGTH: 16
<212> TYPE: PRT
<213> ORGANISM: Aedes aegypti

<400> SEQUENCE: 77

Lys Arg Ile Ser Gly Leu Ile Tyr Glu Glu Thr Arg Gly Val Leu Lys
1               5                   10                  15

<210> SEQ ID NO 78
<211> LENGTH: 16
<212> TYPE: PRT
<213> ORGANISM: Drosophila melanogaster

<400> SEQUENCE: 78

```
Lys Arg Ile Ser Gly Leu Ile Tyr Glu Glu Thr Arg Gly Val Leu Lys
1               5                   10                  15

<210> SEQ ID NO 79
<211> LENGTH: 16
<212> TYPE: PRT
<213> ORGANISM: Bombyx mori

<400> SEQUENCE: 79

Lys Arg Ile Ser Gly Leu Ile Tyr Glu Glu Thr Arg Gly Val Leu Lys
1               5                   10                  15

<210> SEQ ID NO 80
<211> LENGTH: 16
<212> TYPE: PRT
<213> ORGANISM: Caenorhabditis elegans

<400> SEQUENCE: 80

Lys Arg Ile Ser Gly Leu Ile Tyr Glu Glu Thr Arg Gly Val Leu Lys
1               5                   10                  15

<210> SEQ ID NO 81
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"
<220> FEATURE:
<221> NAME/KEY: misc_feature
<222> LOCATION: (11)..(11)
<223> OTHER INFORMATION: May be phosphorylated

<400> SEQUENCE: 81

Arg Lys Thr Val Thr Ala Met Asp Val Val Tyr Ala Leu Lys Arg
1               5                   10                  15
```